United States Patent [19]
Durette et al.

[11] Patent Number: 5,719,158
[45] Date of Patent: Feb. 17, 1998

[54] 16-SUBSTITUTED-4-AZA-ANDROSTANE 5-ALPHA-REDUCTASE ISOZYME 1 INHIBITORS

[75] Inventors: Philippe L. Durette, New Providence; William K. Hagmann, Westfield; Thomas J. Lanza, Jr., Edison; Soumya P. Sahoo, Old Bridge; Gary H. Rasmusson, Watchung; Richard L. Tolman, Warren; Derek von Langen, Fanwood, all of N.J.

[73] Assignee: Merck & Co., Inc., Rahway, N.J.

[21] Appl. No.: 463,544

[22] Filed: Jun. 5, 1995

Related U.S. Application Data

[63] Continuation of PCT/US94/12071, Oct. 21, 1994, which is a continuation-in-part of Ser. No. 141,153, Oct. 21, 1993, abandoned.

[51] Int. Cl.$^6$ .................................................. A61K 31/47
[52] U.S. Cl. ........................... 514/284; 546/77; 546/78; 546/14; 544/318; 544/408
[58] Field of Search .................... 546/77, 78; 514/284

[56] References Cited

U.S. PATENT DOCUMENTS

| | | | |
|---|---|---|---|
| 4,220,775 | 9/1980 | Rasmusson et al. | 546/77 |
| 4,377,584 | 3/1983 | Rasmusson et al. | 546/77 |
| 4,760,071 | 7/1988 | Rasmusson et al. | 546/77 |
| 4,859,681 | 8/1989 | Rasmusson et al. | 546/77 |
| 5,049,562 | 9/1991 | Rasmusson et al. | 546/77 |
| 5,084,574 | 1/1992 | Bhattacharya et al. | 546/77 |
| 5,116,983 | 5/1992 | Bhattacharya et al. | 546/77 |
| 5,120,742 | 6/1992 | Rasmusson et al. | 546/77 |
| 5,138,063 | 8/1992 | Rasmusson et al. | 546/77 |
| 5,151,429 | 9/1992 | Rasmusson et al. | 546/77 |
| 5,215,894 | 6/1993 | Arison et al. | 425/53 |
| 5,278,159 | 1/1994 | Bakshi et al. | 546/77 |
| 5,512,555 | 4/1996 | Waldstreicher | 514/284 |
| 5,543,417 | 8/1996 | Waldstreicher | 514/284 |

FOREIGN PATENT DOCUMENTS

| | | |
|---|---|---|
| 0 004 949 | 10/1979 | European Pat. Off. . |
| 0 155 096 | 9/1985 | European Pat. Off. . |
| 0 285 383 | 10/1988 | European Pat. Off. . |
| 0 547 690 | 6/1993 | European Pat. Off. . |
| 0 285 382 | 3/1994 | European Pat. Off. . |
| 2264494 | 9/1993 | United Kingdom . |
| 2275050 | 8/1994 | United Kingdom . |
| WO 93 23039 | 11/1993 | WIPO . |
| WO 93 23419 | 11/1993 | WIPO . |
| WO 94 20104 | 9/1994 | WIPO . |

OTHER PUBLICATIONS

Helliker, Wall Street Journal, Jun. 7, 1991, at A1, A7, "Alopecia Sufferers Seek to Suffer Less and Not in Silence".
Burger, Medicinal Chemistry, 2nd ed., (1960), p. 42, "Relation of Chemical Structure and Biological Activity".
Stinson, Chem. & Eng. News, pp. 7–8, Jun. 29, 1992, "Prostate Drug Proscar Cleared for Marketing".
Diani et al., J. Clin. Endocrin. & Metab., vol. 74, No. 2, pp. 345–350 (1990), "Hair Growth Effects of Oral Administration of Finasteride, a Steroid 5alpha–Reductase Inhibitor, Alone and in Combination with Topical Minoxidil in the Balding Stumptail Macaque".
Rasmusson et al., J. Med. Chem., vol. 29, pp. 2298–2315 (1986), "Azasteroids: Structure Activity Relationship of Inhibiting 5alpha–Reductase and of Androgen Receptor Binding".
The Daily (Tuesday, May 7, 1996), "New Data on Proscar, Abbott's Hytrin Show Conflicting Results".
Wall Street Journal (Tuesday, May 7, 1996), "Study Finds Abbott's Prostate Drug is Much More Effective than Merck's", p. B4.
US News & World Report, May 20, 1996, "Zapping a problem prostate".
Boyle et al., Urology, "Prostate Volume Predicts Outcome of Treatment of Benign Prostatic Hyperplasia with Finasteride: Meta–Analysis of Randomized Clinical Trials", vol. 48, No. 3, Sep. 1996, pp. 398–405.

*Primary Examiner*—Donald G. Daus
*Attorney, Agent, or Firm*—Catherine D. Fitch; Melvin Winokur

[57] ABSTRACT

Compounds of the Formula I

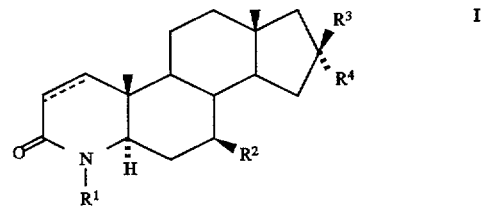

are inhibitors of the 5α-reductase 1 isozyme, and are useful alone, or in combination with a 5α-reductase 2 inhibitor, for the treatment of androgenic sensitive disorders such as acne vulgaris, seborrhea, female hirsutism, male pattern baldness, and benign prostatic hyperplasia.

23 Claims, No Drawings

16-SUBSTITUTED-4-AZA-ANDROSTANE 5-ALPHA-REDUCTASE ISOZYME 1 INHIBITORS

CROSS REFERENCE TO RELATED APPLICATIONS

The present application is a continuation of PCT/US94/12071 filed Oct. 21 1994, which, in turn, is a continuation-in-part of U.S. Ser. No. 08/141,153 filed Oct. 21, 1993, now abandoned.

FIELD OF THE INVENTION

The present invention provides novel compounds, novel compositions, methods of their use and methods of their manufacture, where such compounds are generally pharmacologically useful as agents in therapies whose mechanism of action rely on the selective inhibition of the isozyme 5α-reductase 1.

BACKGROUND OF THE INVENTION

Certain undesirable physiological manifestations, such as acne vulgaris, seborrhea, female hirsutism, androgenetic alopecia which includes female and male pattern baldness, and benign prostatic hyperplasia, are the result of hyperandrogenic stimulation caused by an excessive accumulation of testosterone ("T") or similar androgenic hormones in the metabolic system. Early attempts to provide a chemotherapeutic agent to counter the undesirable results of hyperandrogenicity resulted in the discovery of several steroidal antiandrogens having undesirable hormonal activities of their own. The estrogens, for example, not only counteract the effect of the androgens but have a feminizing effect as well. Non-steroidal antiandrogens have also been developed, for example, 4'-nitro-3'-trifluoromethylisobutyranilide. See Neri, et al., *Endocrinol.* 1972, 91 (2). However, these products, though devoid of hormonal effects, compete with all natural androgens for receptor sites, and hence have a tendency to feminize a male host or the male fetus of a female host and/or initiate feed-back effects which would cause hyperstimulation of the testes.

The principal mediator of androgenic activity in some target organs, e.g., the prostate, is 5α-dihydrotestosterone ("DHT"), formed locally in the target organ by the action of testosterone-5α-reductase (or simply 5α-reductase). Inhibitors of 5α-reductase will serve to prevent or lessen symptoms of hyperandrogenic stimulation in these organs. See especially U.S. Pat. No. 4,377,584, issued Mar. 22, 1983, and U.S. Pat. No. 4,760,071, issued Jul. 26, 1988, both assigned to Merck & Co., Inc. It is now known that a second 5α-reductase isozyme exists, which interacts with skin tissues, especially in scalp tissues. See, e.g., G. Harris, et al., *Proc. Natl. Acad. Sci. USA*, Vol. 89, pp. 10787–10791 (November 1992). The isozyme that principally interacts in skin tissues is conventionally designated as 5α-reductase 1 (or 5α-reductase type 1), while the isozyme that principally interacts within the prostatic tissues is designated as 5α-reductase 2 (or 5α-reductase type 2).

In the treatment of androgenic sensitive disease conditions, e.g., benign prostatic hyperplasia (BPH) and treatment of prostatic cancer, it would be desirable to have one drug entity which is active against both isozymes in the prostate to significantly inhibit all dihydrotestosterone production. It would also be desirable to have another drug entity which is highly selective for inhibiting the isozyme 5α-reductase 1 associated with the scalp, for use in treating conditions of the skin and scalp, e.g., acne vulgaris, male pattern baldness and hirsutism in females. Additionally, a selective 5α-reductase 1 inhibitor could be used in combination with a 5α-reductase 2 inhibitor such as, e.g., finasteride (PROSCAR®), for therapy in the treatment of hyperandrogenic conditions such as BPH and treatment of prostatic cancer, and for the treatment of skin and scalp-related disorders such as acne vulgaris, seborrhea, female hirsutism, and androgenic alopecia. Still further, the 5α-reductase 1 inhibitors of this invention could be used in combination with a potassium channel opener such as minoxidil for the treatment of these skin and scalp-related disorders. Therefore it is an object of this invention to provide compounds that have sufficient activity in the inhibition of 5α-reductase isozyme 1.

SUMMARY OF THE INVENTION

The novel compounds of this invention have the formula

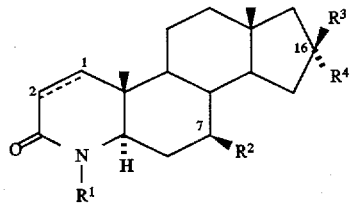

and are selective 5α-reductase 1 inhibitors. It is an object of this invention to provide compounds that alone or in combination with inhibitors of 5α-reductase 2 are useful in the treatment of benign prostatic hyperplasia, prostatitis, and treatment of prostatic cancer. It is an additional object of this invention to provide compounds that alone or in combination with inhibitors of 5α-reductase 2 are useful in the treatment of acne vulgaris, female hirsutism, androgenic alopecia (also known as andregenetic alopecia and human pattern baldness), and insufficient plasma levels of high density lipoproteins. The compounds of the invention have utility in one or more of the aforementioned areas.

DETAILED DESCRIPTION OF THE INVENTION

The novel compounds of the present invention have the general structural Formula I:

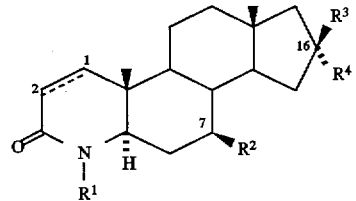

or a pharmaceutically acceptable salt or ester thereof wherein:

the C1–C2 carbon-carbon bond may be a single bond, or a double bond as indicated by the dashed line;

$R^1$ is selected from the group consisting of hydrogen and $C_{1-10}$ alkyl;

$R^2$ is selected from the group consisting of hydrogen and $C_{1-10}$ alkyl; one of $R^3$ and $R^4$ is selected from the group consisting of hydrogen and methyl, and the other is selected from the group consisting of:

(a) amino;

(b) cyano;
(c) fluoro;
(d) methyl;
(e) OH;
(f) —C(O)NR$_b$R$_c$, where R$_b$ and R$_c$ are independently H, C$_{1-6}$ alkyl, aryl, or arylC$_{1-6}$alkyl; wherein the alkyl moiety can be substituted with 1–3 of: halo; C$_{1-4}$alkoxy; or trifluoromethyl; and the aryl moiety can be substituted with 1–3 of: halo; C$_{1-4}$alkyl; C$_{1-4}$ alkoxy; or trifluoromethyl;
(g) C$_{1-10}$ alkyl-X—;
(h) C$_{2-10}$ alkenyl-X—; wherein the C$_{1-10}$ alkyl in (g) and C$_{2-10}$ alkenyl in (h) can be unsubstituted or substituted with one to three of:

i) halo; hydroxy; cyano; nitro; mono-, di- or trihalomethyl; oxo; hydroxysulfonyl; carboxy;

ii) hydroxyC$_{1-6}$alkyl; C$_{1-6}$alkyloxy; C$_{1-6}$ alkylthio; C$_{1-6}$alkylsulfonyl; C$_{1-6}$ alkyloxycarbonyl; in which the C$_{1-6}$ alkyl moiety can be further substituted with 1–3 of: halo; C$_{1-4}$ alkoxy; or trifluoromethyl;

iii) arylthio; aryl; aryloxy; arylsulfonyl; aryloxycarbonyl; in which the aryl moiety can be further substituted with 1–3 of: halo; C$_{1-4}$ alkyl; C$_{1-4}$ alkoxy; or trifluoromethyl;

iv) —C(O)NR$_b$R$_c$; —N(R$_b$)—C(O)—R$_c$; —NR$_b$R$_c$; where R$_b$ and R$_c$ are defined above;

(i) aryl-X—;
(j) heteroaryl-X—, wherein heteroaryl is a 5, 6 or 7 membered heteroaromatic ring containing at least one member selected from the group consisting of: one ring oxygen atom, one ring sulfur atom, 1–4 ring nitrogen atoms, or combinations thereof; in which the heteroaromatic ring can also be fused with one benzo or heteroaromatic ring; wherein the aryl in (i) and heteroaryl in (j) can be unsubstituted or substituted with one to three of:

v) halo; hydroxy; cyano; nitro; mono-, di- or trihalomethyl; mono-, di- or trihalomethoxy; C$_{2-6}$ alkenyl; C$_{3-6}$ cycloalkyl; formyl; hydrosulfonyl; carboxy; ureido;

vi) C$_{1-6}$ alkyl; hydroxy C$_{1-6}$ alkyl; C$_{1-6}$ alkyloxy; C$_{1-6}$ alkyloxy C$_{1-6}$alkyl; C$_{1-6}$ alkylcarbonyl; C$_{1-6}$ alkylsulfonyl; C$_{1-6}$ alkylthio; C$_{1-6}$ alkylsulfinyl; C$_{1-6}$ alkylsulfonamido; C$_{1-6}$ alkylarylsulfonamido; C$_{1-6}$ alkyloxy-carbonyl; C$_{1-6}$ alkyloxycarbonyl C$_{1-6}$alkyl; R$_b$R$_c$N—C(O)—C$_{1-6}$alkyl; C$_{1-6}$ alkanoylamino C$_{1-6}$ alkyl; arylamino C$_{1-6}$ alkyl; wherein the C$_{1-6}$ alkyl moiety can be substituted with 1–3 of: halo; C$_{1-4}$alkoxy; or trifluoromethyl;

vii) aryl; aryloxy; arylcarbonyl; arylthio; arylsulfonyl; arylsulfinyl; arylsulfonamido; aryloxycarbonyl; wherein the aryl moiety can be substituted with 1–3 of: halo; C$_{1-4}$alkyl; C$_{1-4}$alkoxy; or trifluoromethyl;

viii) —C(O)NR$_b$R$_c$; —O—C(O)—NR$_b$R$_c$; —N(R$_b$)—C(O)—R$_c$; —NR$_b$R$_c$; R$_b$—C(O)—N(R$_c$)—; where R$_b$ and R$_c$ are defined in (f) above; and —N(R$_b$)—C(O)—OR$_g$, wherein R$_g$ is C$_{1-6}$alkyl or aryl, in which the alkyl moiety can be substituted with 1–3 of: halo; C$_{1-4}$alkoxy; or trifluoromethyl, and the aryl moiety can be substituted with 1–3 of: halo; C$_{1-4}$alkyl; C$_{1-4}$ alkoxy, or trifluoromethyl; —N(R$_b$)—C(O)NR$_c$R$_d$, wherein R$_d$ is selected from H, C$_{1-6}$ alkyl, and aryl; in which said C$_{1-6}$alkyl and aryl can be substituted as described above in (f) for R$_b$ and R$_c$;

ix) a heterocyclic group, which is a 5, 6 or 7 membered ring, containing at least one member selected from the group consisting of: one ring oxygen atom, one ring sulfur atom, 1–4 ring nitrogen atoms, or combinations thereof; in which the heterocyclic ring can be aromatic, unsaturated, or saturated, wherein the heterocyclic ring can be fused with a benzo ring, and wherein said heterocyclic ring can be substituted with one to three substituents, as defined above for v), vi), vii) and viii), excluding ix) a heterocyclic group; and (k) R$^3$ and R$^4$ taken together can be carbonyl oxygen;
(l) R$^3$ and R$^4$ taken together can be =CH—R$_g$, wherein R$_g$ is defined in viii); and wherein:

X is selected from the group consisting of:
—O—; —S(O)$_n$—; —C(O)—; —CH(R$_e$)—; —C(O)—O—*; —C(O)—N(R$_e$)—*; —N(R$_e$)—C(O)—O—*; —O—C(O)—N(R$_e$)—*; —N(R$_e$)C(O)—N(R$_e$)—; —O—CH(R$_e$)—*; —N(Re)—; wherein R$_e$ is H, C$_{1-3}$ alkyl, aryl, aryl-C$_{1-3}$ alkyl, or unsubstituted or substituted heteroaryl, as defined above in (j); wherein the asterisk (*) denotes the bond which is attached to the 16-position in Structure I; and n is zero, 1 or 2.

Combinations of substituents and/or variables are permissible only if such combinations result in stable compounds.

In one embodiment of the instant invention are compounds of Formula I wherein R$^1$ is hydrogen or methyl and R$^2$ is hydrogen or methyl.

A further embodiment of the instant invention are compounds of Formula I wherein:

one of R$^3$ and R$^4$ is selected from the group consisting of hydrogen and methyl, and the other is selected from the group consisting of:

(b) cyano;
(c) fluoro;
(e) OH;
(g) C$_{1-10}$ alkyl-X—; or C$_{1-10}$ alkyl-X—, where alkyl can be substituted with aryl, and wherein aryl in turn can be substituted with 1–2 of halo or C$_{1-6}$alkyl;
(h) C$_{2-10}$ alkenyl-X—;
(i) aryl-X—;
(j) heteroaryl-X—, wherein heteroaryl is a 5 or 6 membered heteroaromatic ring containing 1–2 ring nitrogen atoms; wherein the aryl in (i) and heteroaryl in (j) can be unsubstituted or substituted with one to two of:

x) halo; cyano; nitro; trihalomethyl; trihalomethoxy; C$_{1-6}$ alkyl; aryl; C$_{1-6}$ alkylsulfonyl; C$_{1-6}$ alkylarylsulfonamino;

xi) —NR$_b$R$_c$; R$_b$—C(O)—N(R$_c$)—; wherein R$_b$ and R$_c$ are independently H, C$_{1-6}$ alkyl, aryl, or arylC$_{1-6}$alkyl; wherein the alkyl moiety can be substituted with 1–3 of: halo; C$_{1-4}$alkoxy; or trifluoromethyl; and the aryl moiety can be substituted with 1–3 of: halo; C$_{1-4}$alkyl; C$_{1-4}$ alkoxy; or trifluoromethyl;

xii) a heterocyclic group, which is a 5 membered aromatic ring, containing one ring nitrogen atom, or one ring oxygen and one ring nitrogen atom; and (k) wherein R$^3$ and R$^4$ taken together can be carbonyl oxygen; and wherein:

X is selected from the group consisting of:
—O—; —S(O)$_n$—; —CH(R$_e$)—; —C(O)—N(R$_e$)—*; —C(O)—N(R$_e$)—*;

wherein R$_e$ is H, C$_{1-3}$ alkyl, aryl, aryl C$_{1-3}$ alkyl;
wherein the asterisk (*) denotes the bond which is attached to the 16-position in Structure I; and n is zero or 2.

Novel compounds of the present invention exemplified by this embodiment include but are not limited to the following compounds:

3-aza-4,7β-dimethyl-5α-androstane-3,16-dione;
4-aza-4-methyl-5α-androstan-3,16-dione;
3-oxo-4-aza-4-methyl-16β-hydroxy-5α-androstane;
3-oxo-4-aza-4-methyl-16β-(benzylaminocarbonyloxy)-5α-androstane;
3-oxo-4-aza-4-methyl-16β-benzoylamino-5α-androstane;
3-oxo-4-aza-4-methyl-16β-methoxy-5α-androstane;
3-oxo-4-aza-4-methyl-16β-allyloxy-5α-androstane;
3-oxo-4-aza-4-methyl-16β-(n-propyloxy)-5α-androstane;
3-oxo-4-aza-4-methyl-16β-hydroxy-5α-androstane;
3-oxo-4-aza-4-methyl-16β-(phenoxy)-5α-androstane;
3-oxo-4-aza-7β-methyl-16β-(phenoxy)-5α-androst-1-ene;
3-oxo-4-aza-4-methyl-16β-methoxy-5α-androstane;
3-oxo-4-aza-4-methyl-16β-(4-chlorophenoxy)-5α-androstane;
3-oxo-4-aza-7β-methyl-16β-(4-chlorophenoxy)-5α-androst-1-ene;
3-oxo-4-aza-7β-methyl-16β-(4-chlorophenoxy)-5α-androstane;
3-oxo-4-aza-7β-methyl-16β-(3-chloro-4-methylphenoxy)-5α-androstane;
3-oxo-4-aza-7β-methyl-16β-(4-methylphenoxy)-5α-androstane;
3-oxo-4-aza-7β-methyl-16β-(4-methylphenoxy)-5α-androst-1-ene;
3-oxo-4-aza-7β-methyl-16β-[4-(1-pyrrolyl)phenoxy]-5α-androst-1-ene;
3-oxo-4-aza-4,7β-dimethyl-16β-hydroxy-5α-androstane;
3-oxo-4-aza-4,7β-dimethyl-16β-methoxy-5α-androstane;
3-oxo-4-aza-4,7β-dimethyl-16β-allyloxy-5α-androstane;
3-oxo-4-aza-4,7β-dimethyl-16β-(3,3-dimethylallyloxy)-5α-androstane;
3-oxo-4-aza-4,7β-dimethyl-16β-(n-propyloxy)-5α-androstane;
3-oxo-4-aza-4,7β-dimethyl-16β-(iso-pentoxy)-5α-androstane;
3-oxo-4-aza-4,16α-dimethyl-16β-hydroxy-5α-androstane;
3-oxo-4-aza-4,7β-dimethyl-16β-ethyloxy-5α-androstane;
3-oxo-4-aza-4,7β-dimethyl-16β-benzyloxy-5α-androstane;
3-oxo-4-aza-4,7β-dimethyl-16α-hydroxy-5α-androstane;
3-oxo-4-aza-4,7β-dimethyl-16β-methylthio-5α-androstane;
3-oxo-4-aza-4,7β-dimethyl-16β-(n-propylthio)-5α-androstane;
3-oxo-4-aza-4,7β-dimethyl-16β-fluoro-5α-androstane;
3-oxo-4-aza-4,7β-dimethyl-16β-cyano-5α-androstane;
3-oxo-4-aza-4-methyl-16β-(1-hexyl)-5α-androstane;
3-oxo-4-aza-4,7β-dimethyl-16β-(n-propyl)-5α-androstane;
3-oxo-4-aza-4,7β-dimethyl-16β-benzyl-5α-androstane;
3-oxo-4-aza-4,7β-dimethyl-16β-(4-chlorobenzyl)-5α-androstane;
3-oxo-4-aza-4,16α-dimethyl-16β-methoxy-5α-androstane;
3-oxo-4-aza-4,7β-dimethyl-16β-(4-cyanophenoxy)-5α-androstane;
3-oxo-4-aza-4,7β-dimethyl-16β-(3-cyanophenoxy)-5α-androstane;
3-oxo-4-aza-4,7β-dimethyl-16β-(4-nitrophenoxy)-5α-androstane;
3-oxo-4-aza-4,7β-dimethyl-16β-(1-naphthyloxy)-5α-androstane;
3-oxo-4-aza-4,7β-dimethyl-16β-(3-chloro-4-methylphenoxy)-5α-androstane;
3-oxo-4-aza-4,7β-dimethyl-16β-(4-methylphenoxy)-5α-androstane;
3-oxo-4-aza-4,7β-dimethyl-16β-(tert-butyloxy)-5α-androstane;
3-oxo-4-aza-4,7β-dimethyl-16β-(3-methyl-1-butyloxy)-5α-androstane;
3-oxo-4-aza-4,7β-dimethyl-16β-(n-propyloxy)-5α-androstane;
3-oxo-4-aza-4,7β-dimethyl-16β-(4-trifluoromethylphenoxy)-5α-androstane;
3-oxo-4-aza-4,7β-dimethyl-16β-(4-trifluoromethoxyphenoxy)-5α-androstane;
3-oxo-4-aza-4,7β-dimethyl-16β-ethylthio-5α-androstane;
3-oxo-4-aza-4,7β-dimethyl-16β-ethylsulfonyl-5α-androstane;
3-oxo-4-aza-4,7β-dimethyl-16β-(4-methylsulfonylphenoxy)-5α-androstane;
3-oxo-4-aza-4,7β-dimethyl-16β-[4-(4-tolylsulfonylamino)phenoxy]-5α-androstane;
3-oxo-4-aza-4,7β-dimethyl-16β-(3-pyridyloxy)-5α-androstane;
3-oxo-4-aza-4,7β-dimethyl-16β-[(4-phenyl)phenoxy]-5α-androstane;
3-oxo-4-aza-4,7β-dimethyl-16β-(4-fluorophenoxy)-5α-androstane;
3-oxo-4-aza-4,7β-dimethyl-16β-(2-pyrazinyloxy)-5α-androstane;
3-oxo-4-aza-4,7β-dimethyl-16β-[4-(5-oxazolyl)phenoxy]-5α-androstane;
3-oxo-4-aza-4,7β-dimethyl-16β-(2-pyrimidinyloxy)-5α-androstane;
3-oxo-4-aza-4,7β-dimethyl-16β-[4-(1-pyrryl)phenoxy]-5α-androstane;
3-oxo-4-aza-4,7β-dimethyl-16β-(4-aminophenoxy)-5α-androstane;
3-oxo-4-aza-4,7β-dimethyl-16β-(4-acetylaminophenoxy)-5α-androstane;
3-oxo-4-aza-4,7β-dimethyl-16β-(4-benzoylaminophenoxy)-5α-androstane;
3-oxo-4-aza-4,7β-dimethyl-16β-(4-chlorophenoxy)-5α-androstane;
3-oxo-4-aza-4,7β-dimethyl-16β-(phenoxy)-5α-androstane;
3-oxo-4-aza-4,7β-dimethyl-16β-(2-chlorophenoxy)-5α-androstane;
3-oxo-4-aza-4,7β-dimethyl-16β-(3-chlorophenoxy)-5α-androstane;
3-oxo-4-aza-4,7β-dimethyl-16β-(4-chlorophenoxy)-5α-androst-1-ene;
3-oxo-4-aza-4,7β-dimethyl-16-(4-chlorobenzylidene)-5α-androstane;
3-oxo-4-aza-4,7β-dimethyl-16-benzylidene-5α-androstane;
3-oxo-4-aza-4,7β-dimethyl-16-(4-methylbenzylidene)-5α-androstane;
3-oxo-4-aza-4,7β-dimethyl-16-(4-chlorobenzyl)-5α-androstane;
3-oxo-4-aza-4,7β-dimethyl-16-(4-methylbenzyl)-5α-androstane;
3-oxo-4-aza-4,7β-dimethyl-16-(3-pyridylmethyl)-5α-androstane;
3-oxo-4-aza-4,7β-dimethyl-16α-methanesulfonyl-5α-androstane;
3-oxo-4-aza-4,7β-dimethyl-16β-thiophenoxy-5α-androstane;
3-oxo-4-aza-4,7β-dimethyl-16β-(4-chlorothiophenoxy)-5α-androstane;
3-oxo-4-aza-4,7β-dimethyl-16β-(4-fluorothiophenoxy)-5α-androstane;
3-oxo-4-aza-4,7β-dimethyl-16β-(4-methylthiophenoxy)-5α-androstane;

3-oxo-4-aza-4,7β-dimethyl-16β-(4-methoxythiophenoxy)-5α-androstane;

3-oxo-4-aza-4,7β-dimethyl-16β-phenylsulfinyl-5α-androstane;

3-oxo-4-aza-4,7β-dimethyl-16β-phenylsulfonyl-5α-androstane;

3-oxo-4-aza-4,7β,16α-trimethyl-16β-(4-trifluoromethylphenoxy)-5α-androstane.

3-oxo-4-aza-4,7β,16α-trimethyl-16β-hydroxy-5α-androstane;

3-oxo-4-aza-4,7β,16α-trimethyl-16β-methoxy-5α-androstane;

pharmaceutically acceptable salts thereof, and analogs of the above-described compounds wherein the C1-C2 carbon-carbon bond is a double bond, and/or $R^1$ is —H, and/or $R^2$ is —H or methyl, where appropriate.

In another embodiment of this invention are compounds of Formula I further limited to those wherein the $C_1$-$C_2$ carbon-carbon bond is a single bond, $R^1$ is methyl, $R^2$ is methyl, $R^3$ is selected from unsubstituted or substituted aryloxy, and $R^4$ is hydrogen.

Some non-limiting examples of compounds within this embodiment are:

3-oxo-4-aza-4,7β-dimethyl-16β-(4-cyanophenoxy)-5α-androstane;

3-oxo-4-aza-4,7β-dimethyl-16β-(3-cyanophenoxy)-5α-androstane;

3-oxo-4-aza-4,7β-dimethyl-16β-(4-nitrophenoxy)-5α-androstane;

3-oxo-4-aza-4,7β-dimethyl-16β-(1-naphthyloxy)-5α-androstane;

3-oxo-4-aza-4,7β-dimethyl-16β-(3-chloro-4-methylphenoxy)-5α-androstane;

3-oxo-4-aza-4,7β-dimethyl-16β-(4-methylphenoxy)-5α-androstane;

3-oxo-4-aza-4,7β-dimethyl-16β-(4-trifluoromethylphenoxy)-5α-androstane;

3-oxo-4-aza-4,7β-dimethyl-16β-(4-trifluoromethoxyphenoxy)-5α-androstane;

3-oxo-4-aza-4,7β-dimethyl-16β-(4-methylsulfonylphenoxy)-5α-androstane;

3-oxo-4-aza-4,7β-dimethyl-16β-[4-(4-tolylsulfonylamino)phenoxy]-5α-androstane;

3-oxo-4-aza-4,7β-dimethyl-16β-[(4-phenyl)phenoxy)-5α-androstane;

3-oxo-4-aza-4,7β-dimethyl-16β-(4-fluorophenoxy)-5α-androstane;

3-oxo-4-aza-4,7β-dimethyl-16β-[4-(5-oxazolyl)phenoxy]-5α-androstane;

3-oxo-4-aza-4,7β-dimethyl-16β-[4-(1-pyrryl)phenoxy]-5α-androstane;

3-oxo-4-aza-4,7β-dimethyl-16β-(4-aminophenoxy)-5α-androstane;

3-oxo-4-aza-4,7β-dimethyl-16β-(4-acetylaminophenoxy)-5α-androstane;

3-oxo-4-aza-4,7β-dimethyl-16β-(4-benzoylaminophenoxy)-5α-androstane;

3-oxo-4-aza-4,7β-dimethyl-16β-(4-chlorophenoxy)-5α-androstane;

3-oxo-4-aza-4,7β-dimethyl-16β-(phenoxy)-5α-androstane;

3-oxo-4-aza-4,7β-dimethyl-16β-(2-chlorophenoxy)-5α-androstane;

3-oxo-4-aza-4,7β-dimethyl-16β-(3-chlorophenoxy)-5α-androstane;

and the pharmaceutically acceptable salts thereof.

A useful compound of the present invention is 3-oxo-4-aza-4,7β-dimethyl-16β-(4-chlorophenoxy)-5α-androstane, or a pharmaceutically acceptable salt thereof.

As used herein "alkyl" is intended to include both branched- and straight-chain saturated aliphatic hydrocarbon groups having the specified number of carbon atoms, e.g., methyl (Me), ethyl (Et), propyl, butyl, pentyl, hexyl, heptyl, octyl, nonyl, decyl, iso-propyl (i-Pr), iso-butyl (i-Bu), tert-butyl (t-Bu), sec-butyl (s-Bu), iso-pentyl, and the like. "Alkyloxy" (or "alkoxy") represents an alkyl group having the indicated number of carbon atoms attached through an oxygen bridge, e.g., methoxy, ethoxy, propyloxy, and the like. "Alkenyl" is intended to include hydrocarbon groups of either a straight or branched configuration with one or more carbon-carbon double bonds which may occur in any stable point along the chain, such as ethenyl, propenyl or allyl, butenyl, pentenyl, and the like. Included in this invention are all E, Z diastereomers.

The alkyl and alkenyl groups can be unsubstituted or substituted with one or more, and preferably 1–3, of:

i) halo; hydroxy; cyano; nitro; mono-, di- or trihalomethyl; oxo; hydroxysulfonyl; carboxy;

ii) hydroxy$C_{1-6}$alkyl; $C_{1-6}$alkyloxy; $C_{1-6}$ alkylthio; $C_{1-6}$alkylsulfonyl; $C_{1-6}$ alkyloxycarbonyl; in which the $C_{1-6}$ alkyl moiety can be further substituted with 1–3 of: halo; $C_{1-4}$ alkoxy; or trifluoromethyl;

iii) arylthio; aryl; aryloxy; arylsulfonyl; aryloxycarbonyl; in which the aryl moiety can be further substituted with 1–3 of: halo; $C_{1-4}$ alkyl; $C_{1-4}$ alkoxy; or trifluoromethyl;

iv) —C(O)NR$_b$R$_c$; —N(R$_b$)—C(O)—R$_c$; —NR$_b$R$_c$; where R$_b$ and R$_c$ are defined above; and halo is F, Cl, Br or I.

The term "oxo", as used herein, indicates an oxo radical which can occur in any stable point along the carbon chain resulting in a formyl group, if at the end of the chain, or an acyl or aroyl group at other points along the carbon chain.

As used herein the term "aryl", i.e., $C_{6-10}$ aryl, is intended to mean phenyl or naphthyl, including 1-naphthyl or 2-naphthyl, either unsubstituted or substituted as described below.

The term "heteroaryl" as used herein, is intended to include a 5, 6 or 7 membered heteroaromatic radical containing at least one member selected from the group consisting of: one ring oxygen atom, one ring sulfur atom, 1–4 ring nitrogen atoms, or combinations thereof; in which the heteroaryl ring can also be fused with one benzo or heteroaromatic ring. This category includes the following either unsubstituted or substituted heteroaromatic rings (as described below): pyridyl, furyl, pyrryl, thienyl, isothiazolyl, imidazolyl, benzimidazolyl, tetrazolyl, pyrazinyl, pyrimidyl, quinolyl, quinazolinyl, isoquinolyl, benzofuryl, isobenzofuryl, benzothienyl, pyrazolyl, indolyl, isoindolyl, purinyl, carbazolyl, isoxazolyl, thiazolyl, isothiazolyl, oxazolyl, benzthiazolyl, and benzoxazolyl. The heteroaryl ring may be attached within structural Formula I by a heteroatom, e.g., N, or carbon atom in the ring, which results in the creation of a stable structure. The heteroaryl ring can also be fused to a benzo ring.

The one to three, and more usefully one to two substituents which can be on the $C_{6-10}$ aryl and heteroaryl groups named above are independently selected from:

v) halo; hydroxy; cyano; nitro; mono-, di- or trihalomethyl; mono-, di- or trihalomethoxy; $C_{2-6}$ alkenyl; $C_{3-6}$ cycloalkyl; formyl; hydrosulfonyl; carboxy; ureido;

vi) $C_{1-6}$ alkyl; hydroxy $C_{1-6}$ alkyl; $C_{1-6}$ alkyloxy; $C_{1-6}$ alkyloxy $C_{1-6}$alkyl; $C_{1-6}$ alkylcarbonyl; $C_{1-6}$ alkylsulfonyl; $C_{1-6}$ alkylthio; $C_{1-6}$ alkylsulfinyl; $C_{1-6}$ alkylsulfonamido; $C_{1-6}$ alkylarylsulfonamido; $C_{1-6}$ alkyloxycarbonyl; $C_{1-6}$ alkyloxycarbonyl $C_{1-6}$alkyl; $R_bR_cN$—C(O)—$C_{1-6}$alkyl; $C_{1-6}$ alkanoylamino $C_{1-6}$ alkyl; aroylamino $C_{1-6}$ alkyl; wherein the $C_{1-6}$ alkyl moiety can be substituted with 1-3 of: halo; $C_{1-4}$alkoxy; or trifluoromethyl;

vii) aryl; aryloxy; arylcarbonyl; arylthio; arylsulfonyl; arylsulfinyl; arylsulfonamido; aryloxycarbonyl; wherein the aryl moiety can be substituted with 1-3 of: halo; $C_{1-4}$alkyl; $C_{1-4}$alkoxy; or trifluoromethyl;

viii) —C(O)N$R_bR_c$; —O—C(O)—N$R_bR_c$; —N($R_b$)—C(O)—$R_c$; —N$R_bR_c$; $R_b$—C(O)—N($R_c$)—; where $R_b$ and $R_c$ are defined in (e) above; and —N($R_b$)—C(O)—O$R_c$, wherein this instance $R_c$ is $C_{1-6}$alkyl or aryl; —N($R_b$)—C(O)N$R_cR_d$, wherein $R_d$ is selected from H, $C_{1-6}$ alkyl, and aryl; in which said $C_{1-6}$alkyl and aryl can be substituted as described above in (e) for $R_b$ and $R_c$;

ix) a heterocyclic group, which is a 5, 6 or 7 membered ring, containing at least one member selected from the group consisting of: one ring oxygen atom, one ring sulfur atom, 1-4 ring nitrogen atoms, or combinations thereof; in which the heterocyclic ring can be aromatic, unsaturated, or saturated, and wherein the heterocyclic ring can be fused with a benzo ring, and, wherein said heterocyclic ring can be substituted with one to three substituents, as defined above for v), vi), vii) and viii), excluding ix) a heterocyclic group.

The fused heteroaromatic ring systems include: purine, imidazoimidazole, imidazothiazole, pyridopyrimidine, pyridopyridazine, pyrimidopyrimidine, imidazopyridazine, pyrrolopyridine, imidazopyridine, and the like.

The "heterocyclic" group includes the fully unsaturated heteroaryl rings described above and also their respective dihydro, tetrahydro and hexahydro derivatives resulting in partially unsaturated and fully saturated versions of the ring systems. Examples include: dihydroimidazolyl, dihydrooxazolyl, dihydropyridyl, tetrahydrofuryl, dihydropyrryl, tetrahydrothienyl, dihydroisothiazolyl, 1,2-dihydrobenzimidazolyl, 1,2-dihydrotetrazolyl, 1,2-dihydropyrazinyl, 1,2-dihydropyrimidyl, 1,2-dihydroquinolyl, 1,2,3,4-tetrahydroisoquinolyl, 1,2,3,4-tetrahydrobenzofuryl, 1,2,3,4-tetrahydroisobenzofuryl, 1,2,3,4-tetrahydrobenzothienyl, 1,2,3,4-tetrahydropyrazolyl, 1,2,3,4-tetrahydroindolyl, 1,2,3,4-tetrahydroisoindolyl, 1,2,3,4-tetrahydropurinyl, 1,2,3,4-tetrahydrocarbazolyl, 1,2,3,4-tetrahydroisoxazolyl, 1,2,3,4-tetrahydrothiazolyl, 1,2,3,4-tetrahydrooxazolyl, 1,2,3,4-tetrahydrobenzthiazolyl, and 1,2,3,4-tetrahydrobenzoxazolyl and the like.

The heterocyclic group can be substituted in the same fashion as described above for heteroaryl.

Whenever the terms "alkyl", "alkenyl", "alkyloxy (or alkoxy)", "aryl" or "heteroaryl", or one of their prefix roots, appear in a name of a substituent in Formula I, (e.g., aralkoxyaryloxy) they shall have the same definitions as those described above for "alkyl", "alkenyl", "alkyloxy (or alkoxy)", "aryl" and "heteroaryl", respectively. Designated numbers of carbon atoms (e.g., $C_{1-10}$) shall refer independently to the number of carbon atoms in an alkyl or alkenyl moiety or to the alkyl or alkenyl portion of a larger substituent in which alkyl or alkenyl appears as its prefix root.

Also included within the scope of this invention are pharmaceutically acceptable salts of the compounds of Formula I, where a basic or acidic group is present on the structure. When an acidic substituent is present, e.g., —COOH, there can be formed the ammonium, sodium, potassium, calcium salt, and the like, for use as the dosage form. Where a basic group is present, i.e., amino or a basic heteroaryl radical such as, e.g., 4-pyridyl, an acidic salt, i.e., hydrochloride, hydrobromide, acetate, pamoate, and the like, can be used as the dosage form.

Also, in the case of the —COOH group being present, pharmaceutically acceptable esters can be employed, e.g., $C_{1-5}$ alkyl, pivaloyloxymethyl, and the like, and those esters known in the art for modifying solubility or hydrolysis characteristics for use as sustained release or prodrug formulations.

Representative salts include the following salts: acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoelate, iodide, tosylate, isothionate, triethiodide, lactate, and valerate.

In addition, some of the compounds of the instant invention may form solvates with water or common organic solvents. Such solvates are encompassed within the scope of this invention.

The term "therapeutically effective amount" shall mean that amount of a drug or pharmaceutical agent that will elicit the biological or medical response of a tissue, system, animal or human that is being sought by a researcher, veterinarian, medical doctor or other clinician.

The compounds of the present invention have chiral centers and may occur as racemates, racemic mixtures and as individual enantiomers or diastereomers, with all isomeric forms being included in the present invention as well as mixtures thereof. Furthermore, some of the crystalline forms for compounds of the present invention may exist as polymorphs and as such are intended to be included in the present invention.

Accordingly, the present invention has the objective of providing methods of treating the hyperandrogenic conditions of androgenic alopecia including male pattern baldness, acne vulgaris, seborrhea, and female hirsutism by oral, systemic, parenteral or topical administration of the novel compounds of Formula I either alone or in combination with a 5α-reductase 2 inhibitor, and/or further in combination with: a potassium channel opener, e.g., minoxidil; an anti-androgen, e.g., flutamide; a retinoid, e.g., tretinoin or isotretinoin; an alpha-1 receptor antagonist, e.g., terazocin.

The term "treating androgenic alopecia" is intended to include the arresting and/or reversing of androgenic alopecia, and the promotion of hair growth. The present invention has the further objective of providing methods of treating benign prostatic hyperplasia, prostatitis, and treating and/or preventing prostatic carcinoma by oral, systemic or parenteral administration of the novel compounds of Formula I either alone or in combination with a 5α-reductase 2 inhibitor.

The present invention also has the objective of providing suitable topical, oral, systemic and parenteral pharmaceutical formulations for use in the novel methods of treatment of the present invention. The compositions containing the present compounds as the active ingredient for use in the treatment of the above-noted hyperandrogenic conditions can be administered in a wide variety of therapeutic dosage forms in conventional vehicles for systemic administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts.

The pharmaceutical compositions included herein include those comprising a pharmaceutically acceptable carrier and a therapeutically effective amount of a compound of Formula I of this invention; which can further contain:

(1) a therapeutically effective amount of an inhibitor of 5α-reductase 2, or a pharmaceutically acceptable salt thereof, e.g., finasteride, epristeride or turosteride;

(2) a potassium channel opener, or a pharmaceutically acceptable salt thereof, e.g., minoxidil;

(3) a therapeutically effective amount of a retinoid, or a pharmaceutically acceptable salt thereof, e.g., tretinoin, isotretinoin, (4) a therapeutically effective amount of an anti-androgen, or a pharmaceutically acceptable salt thereof, e.g., flutamide, spironolactone, or casodex.

The daily dosage of the products may be varied over a range from 0.1 to 1,000 mg per adult human/per day. For oral administration, the compositions are preferably provided in the form of scored or unscored tablets containing 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.002 mg/kg to about 50 mg/kg of body weight per day. The range is more particularly from about 0.01 mg/kg to 7 mg/kg of body weight per day.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For the treatment of androgenic alopecia including male pattern baldness, acne vulgaris, seborrhea, and female hirsutism, the compounds of the present invention may be administered in a pharmaceutical composition comprising the active compound in combination with a pharmaceutically acceptable carrier adapted for topical administration. Topical pharmaceutical compositions may be, e.g., in the form of a solution, cream, ointment, gel, lotion, shampoo or aerosol formulation adapted for application to the skin. These topical pharmaceutical compositions containing the compounds of the present invention ordinarily include about 0.001% to 15% by weight of the active compound in admixture with a pharmaceutically acceptable vehicle.

For the treatment of acne vulgaris, androgenic alopecia including male pattern baldness, seborrhea, female hirsutism, benign prostatic hyperplasia, prostatitis and the treatment of prostatic cancer, the compounds of the instant invention can be used alone or can be combined with a therapeutically effective amount of a 5α-reductase 2 inhibitor, such as finasteride, in a single oral, systemic, or parenteral pharmaceutical dosage formulation. Also, for the skin and scalp related disorders of acne vulgaris, androgenic alopecia including male pattern baldness, seborrhea, and female hirsutism, the compounds of the instant invention and a 5α-reductase 2 inhibitor can be formulated for topical administration. Alternatively, a combined therapy can be employed wherein the compound of Formula I and the 5α-reductase 2 inhibitor are administered in separate oral, systemic, parenteral or topical dosage formulations. For example, a compound of Formula I and e.g., finasteride can be administered in a single oral or topical dosage formulation, or each active agent can be administered in a separate dosage formulation, e.g., in separate oral dosage formulations, or an oral dosage formulation of finasteride in combination with a topical dosage formulation of a compound of Formula I. See, e.g., U.S. Pat. Nos. 4,377,584 and 4,760,071 which describe dosages and formulations for 5α-reductase inhibitors. Where the active agents are in separate dosage formulations, they can be administered concomitantly, or they each can be administered at separately staggered times.

Other 5α-reductase type 2 inhibitors useful in the above-described method are also included within the scope of this invention. Examples which are non-limiting are: 17β-(N-tert-butyl-carbamoyl)androsta-3,5-diene-3-carboxylic acid (epristeride, Smith Kline & Beecham, SKF 105657), which is described in WO9113550 which corresponds to U.S. Pat. No. 5,516,768 and WO9319758; and 17β-[N-isopropyl-N-(isopropylcarbamoly)carbamoyl]-4-methyl-4-aza-5α-androstan-3-one, (turosteride, Farmitalia, FCE 26073), which is described in U.S. Pat. No. 5,155,107, and derivatives thereof.

Furthermore, administration of a compound of the present invention in combination with a therapeutically effective amount of a potassium channel opener, such as minoxidil, cromakalin, pinacidil, a compound selected from the classes of S-triazine, thiane-1-oxide, benzopyran, and pyridinopyran derivatives or a pharmaceutically acceptable salt thereof, may be used for the treatment of androgenic alopecia including male pattern baldness. The active agents can be administered in a single topical dosage formulation, or each active agent can be administered in a separate dosage formulation, e.g., in separate topical dosage formulations, or an oral dosage formulation of a compound of Formula I in combination with a topical dosage formulation of, e.g., minoxidil. See, e.g., U.S. Pat. Nos. 4,596,812, 4,139,619 and WO 92/02225, published 20 Feb. 1992, for dosages and formulations of calcium channel openers. Where the active agents are in separate dosage formulations, they can be administered concurrently, or they each can be administered at separately staggered times.

Furthermore, for the treatment of acne vulgaris and/or androgenic alopecia, a combined therapy can be used by administering a therapeutically effective amount of a compound of Formula I, alone or in combination with a 5α-reductase 2 inhibitor, or further in combination with a therapeutically effective amount of a retinoid, e.g., retinoic acid or an ester or amide derivative thereof, such as e.g., tretinoin (RETIN A) or isotretinoin (ACCUTANE, Roche, see U.S. Pat. No. 3,006,939; U.S. Pat. No. 3,746,730; U.S. Pat. No. 4,556,518).

Also, for the treatment of acne vulgaris, androgenic alopecia, seborrhea, female hirsutism, benign prostatic hyperplasia, prostatitis and the treatment of prostatic cancer, a combined therapy can be used by administering a therapeutically effective amount of a compound of Formula I with a therapeutically effective amount of an anti-androgen, such as, e.g., flutamide, spironolactone or casodex.

Also covered in this invention is a method of for treating benign prostatic hyperplasia comprising the step of administering to a mammal in need of such treatment a therapeutically effective amount of a compound of Formula I, or a therapeutically effective amount of a compound of Formula I in combination with an inhibitor of 5α-reductase 2. This method also includes the use of an alpha-1 receptor antagonist, e.g., terazosin (Abbott, see U.S. Pat. Nos. 4,026, 894; 4,251,532).

Also covered is a method of inhibiting the biosynthetic conversion of testosterone to dihydrotesterone in a mammal in need of such treatment comprising the step of administering to said mammal a therapeutically effective amount of a compound of Formula I, or a therapeutically effective amount of a compound of Formula I in combination with an inhibitor of 5α-reductase 2.

Also covered is a method of inhibiting 5α-reductase or the isozymes thereof, in a mammal in need of such treatment, comprising the step of administering to said mammal a therapeutically effective amount of a compound of Formula I, or a therapeutically effective amount of a compound of Formula I in combination with an inhibitor of 5α-reductase 2.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethyl-cellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl celluose, agar, bentonite, xanthan gum and the like.

The liquid forms in suitably flavored suspending or dispersing agents such as the synthetic and natural gums, for example, tragacanth, acacia, methyl-cellulose and the like.

Other dispersing agents which may be employed include glycerin and the like. For parenteral administration, sterile suspensions and solutions are desired. Isotonic preparations which generally contain suitable preservatives are employed when intravenous administration is desired.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations. See, e.g., EP 0 285 382.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinyl-pyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

The compounds Of the present invention can be prepared readily according to the following reaction Schemes and Examples or modifications thereof using readily available starting materials, reagents and conventional synthesis procedures. In these reactions, it is also possible to make use of variants which are themselves known to those of ordinary skill in this art, but are not mentioned in greater detail. Specific definitions of variables in the Schemes (e.g., R=CH$_3$) are illustrative only, and are not intended to limit the procedures described. Some abbreviations used herein are as follows: Ph is phenyl; Ac is an acyl group; t-Bu is tert-butyl; Et is ethyl; Me is methyl; i-Am is iso-amyl; EtOAc is ethyl acetate.

The inhibitors described in Scheme 1 can be prepared as follows. 4-Aza-4-methyl-5α-androstan-3,17-dione (A) is first converted into the isomeric 3,16-dione 1 by the following sequence of reactions: (1) treatment of A with isoamyl nitrite in t-butanol in the presence of potassium t-butoxide to generate the intermediate 16-oximino-17-ketone; (2) reduction of the 17-keto group with hydrazine hydrate and potassium hydroxide in ethylene glycol at elevated temperatures to give 16-oxime B; and (3) cleavage of the 16-oximino group in B either by hydrolysis with aqueous acetic acid at elevated temperatures or with sodium bisulfite followed by treatment with aqueous hydrochloric acid to afford 1. Reduction of the 16-ketone 1 to the 1 61β-alcohol 2 is carried out with a suitable hydride-based reducing agent, such as sodium borohydride in methanol or lithium tri-sec-butylborohydride in tetrahydrofuran (THF). Alcohol 2 is converted into its alkyl ether derivatives 3 and 4, by first generating the alkoxide union with potassium hydride in N,N-dimethylformamide (DMF) or potassium hydroxide in dimethyl sulfoxide (DMSO) followed by addition of the appropriate alkyl bromide or iodide. The 16β-(n-propyloxy) derivative 5 is obtained from the precursor 16β-(allyloxy) derivative 4 by catalytic hydrogenation.

The inhibitors described in Scheme 2 can be prepared as follows. 16-Oxime B is converted into the 16β-amine C by catalytic hydrogenation in the presence of a heterogeneous catalyst such as platinum oxide in aqueous acetic acid. Acylation of C is effected with the appropriate acid anhydride or acid chloride in the presence of an acid acceptor such as pyridine, triethylamine, and 4-dimethylaminopyridine (DMAP). In this fashion are obtained examples 6 and 7. Carbamates, such as 8 depicted in Scheme 3, are made by treatment of alcohol 2 with the appropriate isocyanate in the presence of an organic base, such as triethylamine, pyridine, and 4-dimethylaminopyridine.

The inhibitors described in Scheme 4 can be prepared as follows. The 16β-alcohol 2 is converted into the 16α-alcohol 9 by treatment with 4-nitro-benzoic acid in the presence of diethyl azadicarboxylate (DEAD) and triphenylphosphine to generate the intermediate 16α-(p-nitrobenzoate) ester D followed by hydrolysis in aqueous base in an appropriate alcohol solvent. Alkylation of 9 is carried out in an analogous fashion as described above with alcohol 2 to yield the desired 16α-alkyl ethers, such as the 16α-methoxy derivative (example 10) shown in Scheme 4.

The 7β-methyl inhibitors described in Scheme 5 are prepared in a similar manner as that described above for the examples in Scheme 1, but using instead as starting material, 4-aza-4,7β-dimethyl-5α-androstan-3,17-dione (E).

The 7β-methyl inhibitors described in Scheme 6 are prepared as follows. Compound 20 is prepared by treatment of alcohol 12 with t-butyl trichloroacetimidate in the presence of an organic sulfonic acid, such as trifluoromethanesulfonic acid. The 16β-aryloxy derivatives, such as Examples 21–24, are obtained by first generating the alkoxide anion from alcohol 12 with potassium or sodium hydride in tetrahydrofuran or N,N-dimethylformamide or potassium hydroxide in dimethylsulfoxide and subsequent addition of the appropriately substituted fluorobenzene.

The 7β-methyl inhibitors described in Scheme 7 are prepared in a similar manner as that described above for the examples in Scheme 4, but using instead as starting material the 7β-methyl-16β-ol intermediate 12. Inversion of configuration at the 16-position to form (F) is effected using a Mitsunobu-based transformation as shown in Scheme 7. O-Alkylation to generate 16α-ethers, such as 26, is performed as already described above.

The inhibitors described in Scheme 8 are prepared as follows. Addition of methylmagnesium bromide in tetrahydrofuran to either ketone 1 or 11 affords the corresponding 16α-methyl-16β-alcohol 27 or 28. O-Alkylation or O-arylation is then carried out as described in the previous Schemes to afford the 16β-methyl-16β-ether derivatives, such as Examples 29 and 30.

The inhibitors described in Scheme 9 are prepared by the following reaction routes. The 7β-methyl-16α-alcohol 25 is converted into the 16β-thiol H by treatment with thiolacetic acid in the presence of diisopropyl azodicarboxylate (DIAD) and triphenylphosphine to give the intermediate 16β-thioacetate G, which is then hydrolyzed under basic conditions to yield thiol H. Alkylation is effected by generating the mercaptide anion with sodium hydride or potassium hydride in tetrahydrofuran or N,N-dimethyl-formamide followed by addition of the appropriate alkyl halide. In this fashion are prepared Examples 31–33. The corresponding sulfones, such as Example 34, are obtained by treatment of the precursor thioethers 31–33 with an oxidizing agent, such as organic peracid or potassium peroxymonosulfate (OXONE), the latter in aqueous methanol.

The inhibitors described in Scheme 10 are prepared by the following synthetic pathways. The p-nitrophenoxy derivative 50 is reduced with Pd on carbon at room temperature in a $H_2$ atmosphere to yield the p-amino-phenoxy derivative 51. The amine is then acylated with acetyl chloride in methylene chloride in the presence of pyridine to yield the p-acetylaminophenoxy derivative 52, or likewise treated with benzoyl chloride to yield the corresponding p-benzoylamino analog 53. Alternately, the amino compound 51 is treated with tosyl chloride to yield the p-tosylamino analog 54.

The inhibitors described in Scheme 11 are prepared as follows. The N-2,4-dimethoxybenzyl protected 16-alcohol 55 is treated with p-fluorochlorobenzene and potassium hydride in dimethylformamide to yield the p-chlorophenoxy derivative 56, which is then treated with trifluoroacetic acid in methylene chloride to remove the N-2,4-dimethoxybenzyl protecting group to yield 57. This is treated with hydrogen gas and a palladium on carbon catalyst in methanol to dechlorinate the phenyl ring to yield the phenoxy derivative 58. This compound is treated with methyl iodide and sodium hydride in dimethylformamide to methylate the ring nitrogen to yield 61. Alternately, 58 is treated with DDQ and BSTFA in toluene to introduce a double bond at the 1-position to yield 59. Utilizing the same reduction reaction scheme, the 1,2-dihydro androstane 57 yields the p-chloroandrost-1-ene 60. This is then methylated at the 1-position by treatment with methyl iodide, sodium hydride in dimethylformamide to yield 62.

The inhibitors described in Scheme 12 are prepared via similar reaction pathways as described in Scheme 11. The N-2,4-dimethoxybenzyl protected 16-alcohol 55 is treated with 4-methyl-3-chlorofluorobenzene and potassium hydride in dimethylformamide to yield the 4-methyl-3-chlorophenoxy derivative 63, which is then treated with trifluoroacetic acid in methylene chloride to remove the N-2,4-dimethoxybenzyl protecting group to yield 64. This is treated with hydrogen gas and a palladium on carbon catalyst in methanol to dechlorinate the phenyl ring to yield the p-methylphenoxy derivative 65. This compound is treated with methyl iodide and sodium hydride in dimethylformamide to methylate the ring nitrogen to yield 67. Alternately, 65 is treated with DDQ and BSTFA in toluene to introduce a double bond at the 1-position to yield 66.

The inhibitors in Scheme 13 are prepared as follows. The starting 16-alcohol 25 is treated with methanesulfonic acid in pyridine containing DMAP to yield the mesylate 77. This in turn is treated with an appropriate thiophenol in anhydrous THF containing sodium hydride to yield the thiophenoxy 78, 4-chlorothiophenoxy 79, 4-fluorothiophenoxy 80, 4-methylthiophenoxy 81) and the 4-methoxythiophenoxy 82 derivatives. Treatment of the thiophenoxy 78 derivative with m-chloroperbenzoic acid in methylene chloride at 0° C. for one hour yields the phenylsulfinyl derivative 83. Treatment of the phenylsulfinyl compound 83 under the same reaction conditions prolonged however for three hours, yields the phenylsulfonyl derivative 84.

The inhibitors for Scheme 14 are prepared as follows. The 16-ketone (11) is treated with an appropriate arylmethyl diethylphosphonate under Wittig conditions using sodium hydride in DMF at 80°–100° C. to yield the corresponding 4-chlorobenzylidene 71, benzylidene 72 and 4-methylbenzylidene 73 analogs. These are reduced in ethanol under a hydrogen atmosphere using a 5% rhodium on carbon catalyst to yield the corresponding 4-chlorobenzyl 74 and 4-methylbenzyl 75 derivatives. The 3-pyridyl-methyl 76 analog is made in the same two step manner.
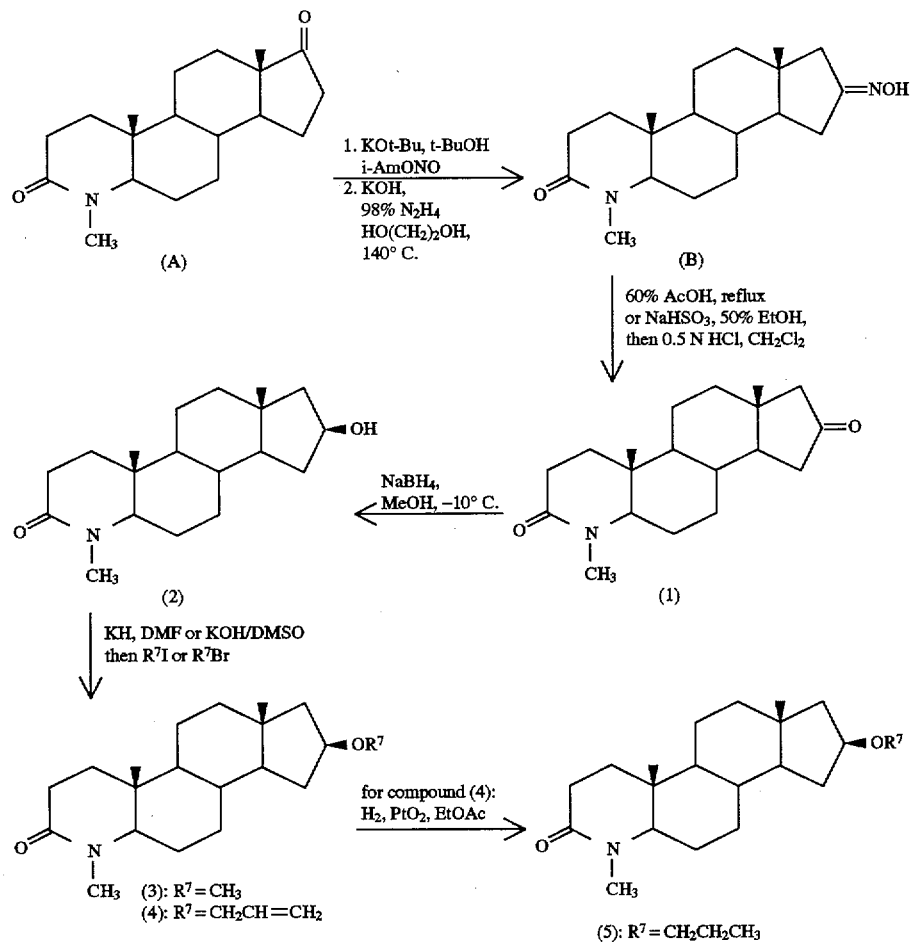
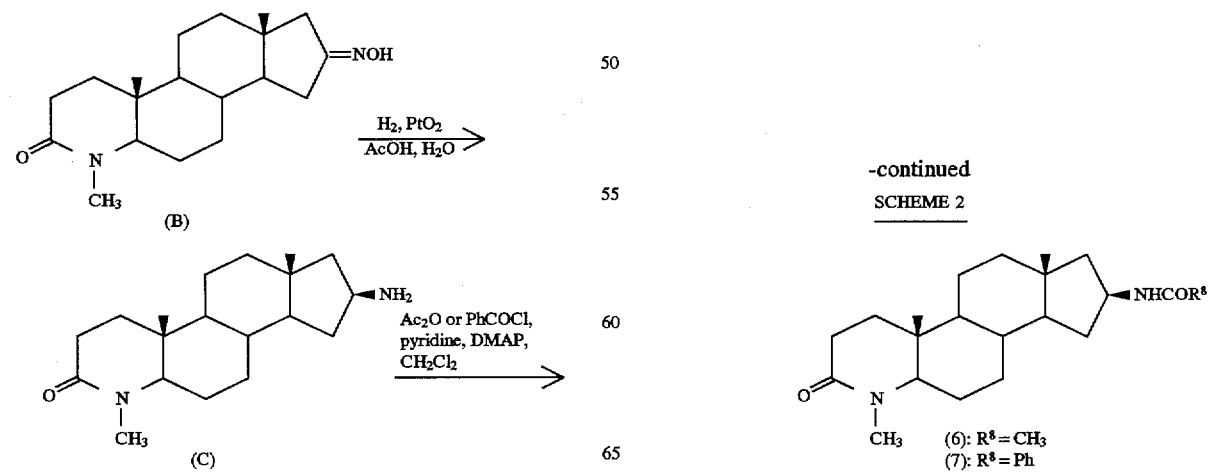
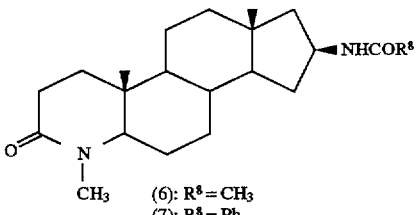

SCHEME 3
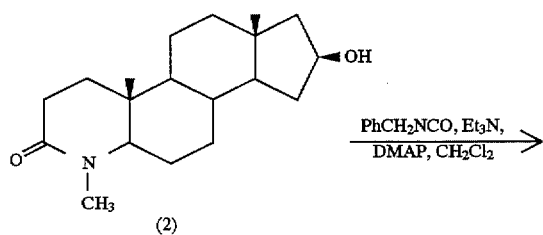
(2)
PhCH₂NCO, Et₃N, DMAP, CH₂Cl₂ →
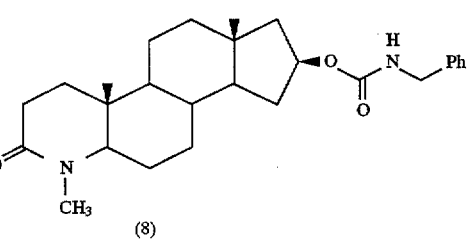
(8)
SCHEME 4
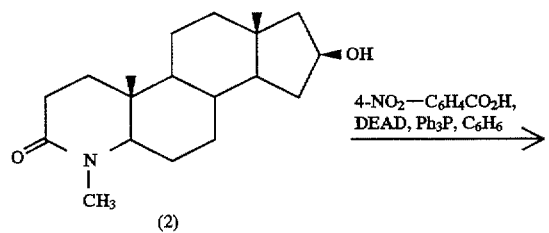
(2)
4-NO₂—C₆H₄CO₂H, DEAD, Ph₃P, C₆H₆ →
-continued
SCHEME 4
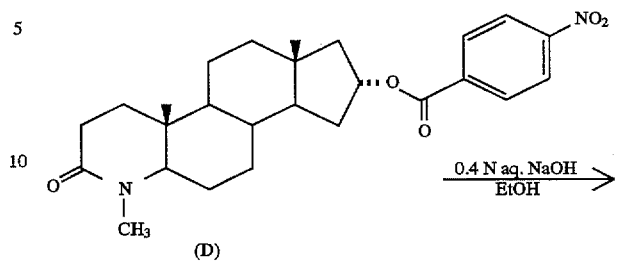
(D)
0.4 N aq. NaOH / EtOH →
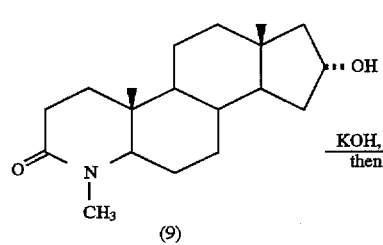
(9)
KOH, DMSO then CH₃I →
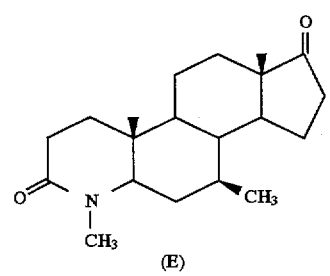
(10)
SCHEME 5
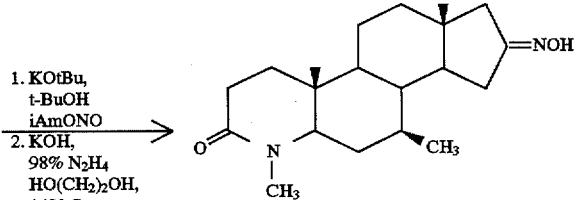
(E)
1. KOtBu, t-BuOH, iAmONO
2. KOH, 98% N₂H₄, HO(CH₂)₂OH, 140° C.
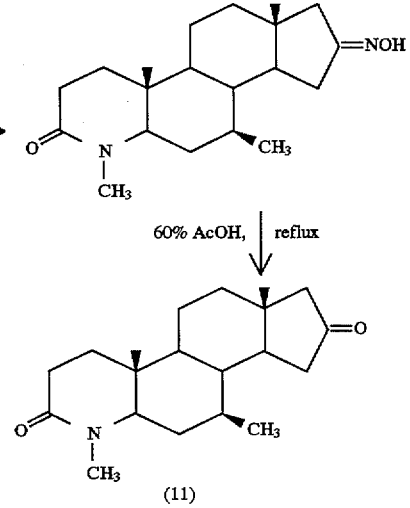
60% AcOH, reflux ↓
(11)
NaBH₄, MeOH, −10° C. ←
(12)
KH/DMF or KOH/DMSO then R⁹I or R⁹Br ↓

-continued
SCHEME 5
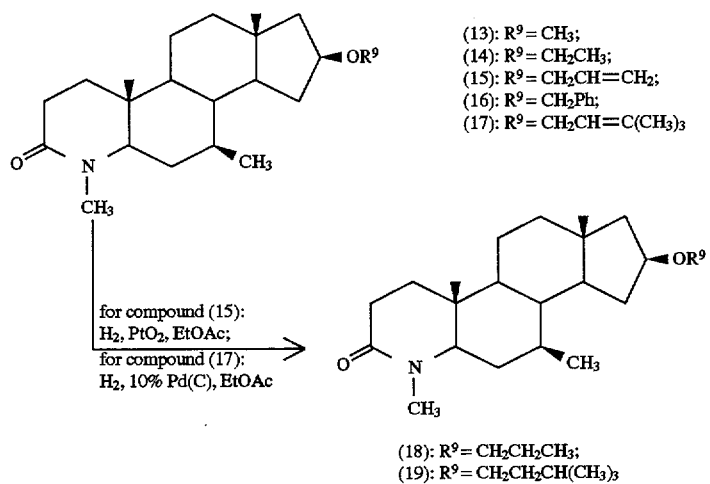
(13): $R^9 = CH_3$;
(14): $R^9 = CH_2CH_3$;
(15): $R^9 = CH_2CH=CH_2$;
(16): $R^9 = CH_2Ph$;
(17): $R^9 = CH_2CH=C(CH_3)_3$
(18): $R^9 = CH_2CH_2CH_3$;
(19): $R^9 = CH_2CH_2CH(CH_3)_3$
SCHEME 6
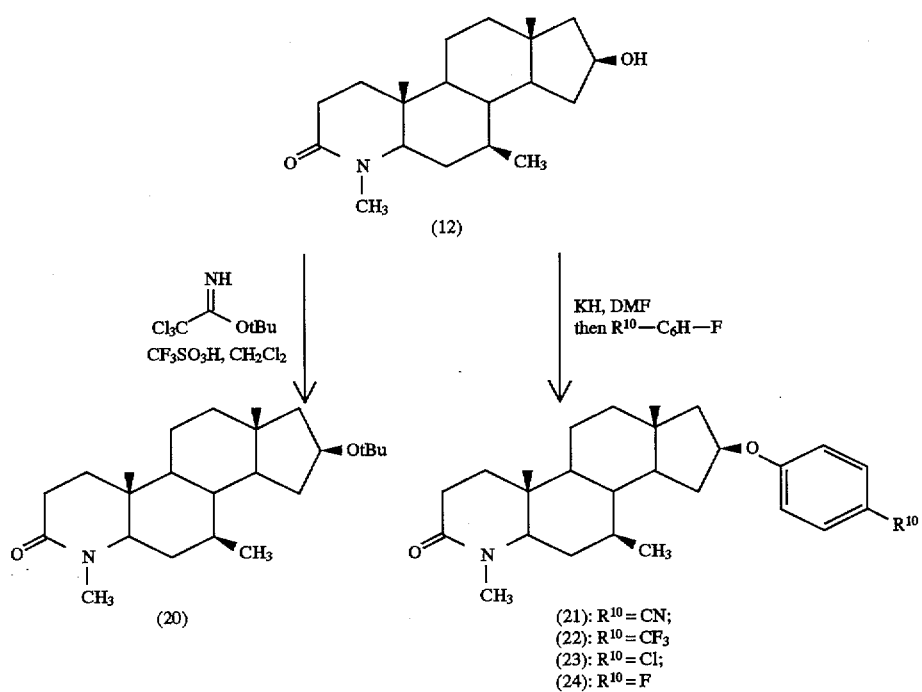
(21): $R^{10} = CN$;
(22): $R^{10} = CF_3$;
(23): $R^{10} = Cl$;
(24): $R^{10} = F$ SCHEME 7
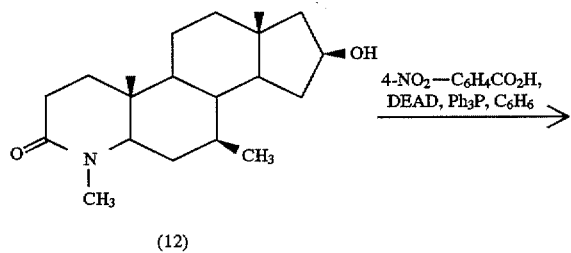
(12)
4-NO₂—C₆H₄CO₂H,
DEAD, Ph₃P, C₆H₆
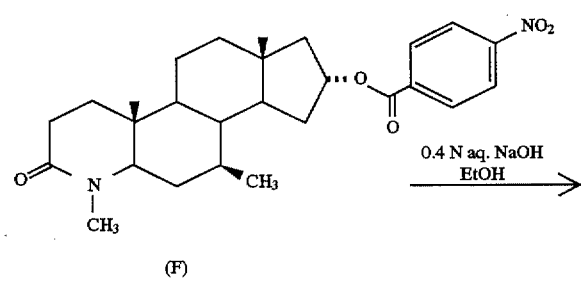
(F)
0.4 N aq. NaOH
EtOH
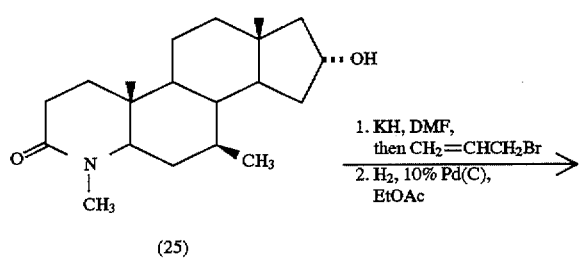
(25)
1. KH, DMF,
   then CH₂=CHCH₂Br
2. H₂, 10% Pd(C),
   EtOAc
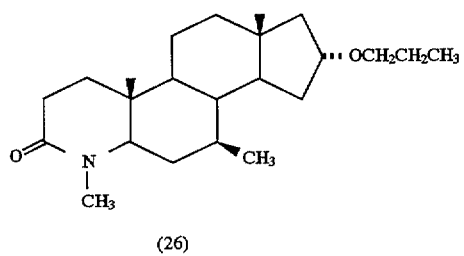
(26)
SCHEME 8
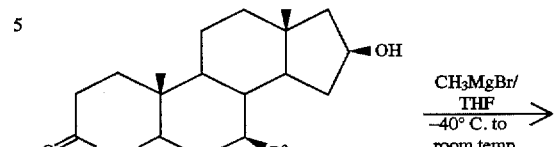
R² = H or CH₃
CH₃MgBr/
THF
−40° C. to
room temp.
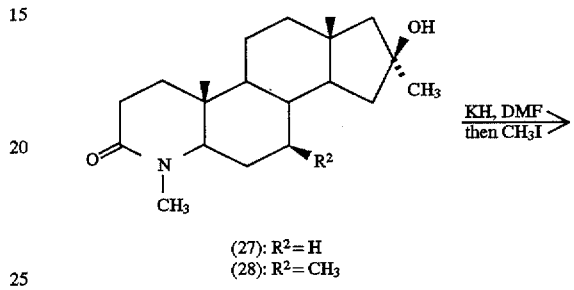
(27): R² = H
(28): R² = CH₃
KH, DMF
then CH₃I
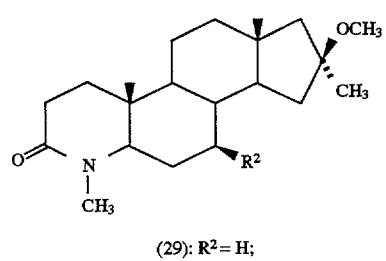
(29): R² = H;
(30): R² = CH₃
SCHEME 9
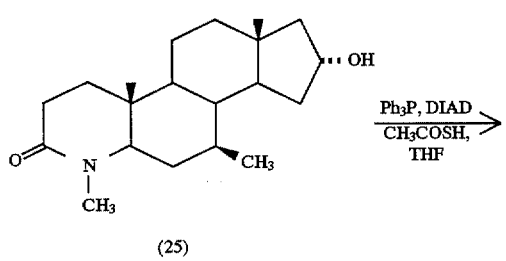
(25)
Ph₃P, DIAD
CH₃COSH,
THF
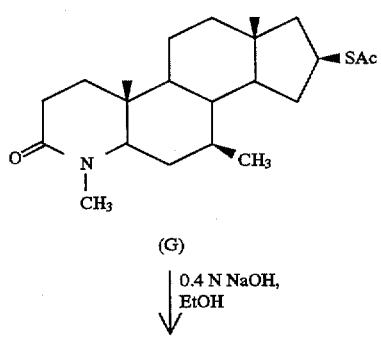
(G)
0.4 N NaOH,
EtOH -continued
SCHEME 9
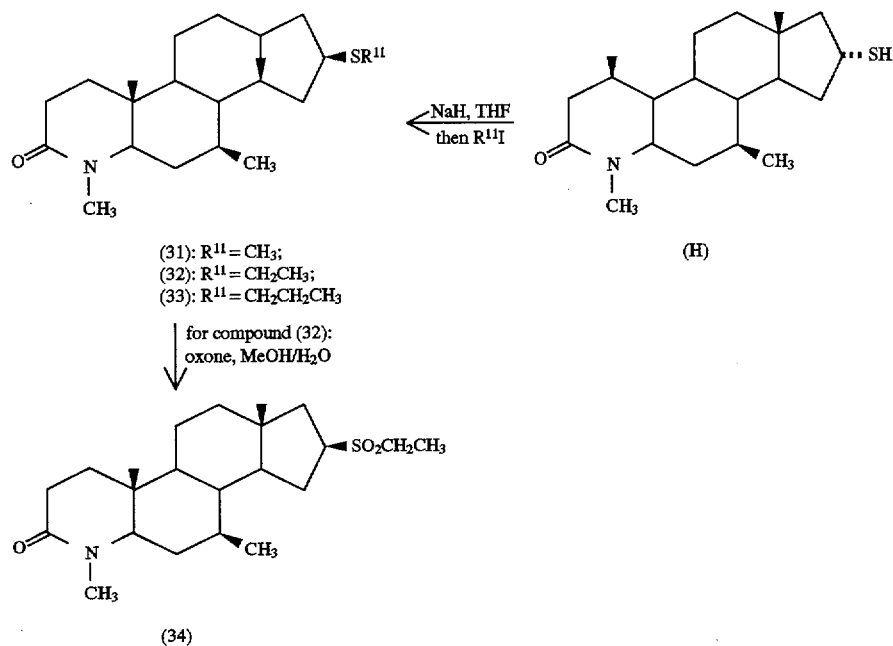
SCHEME 10
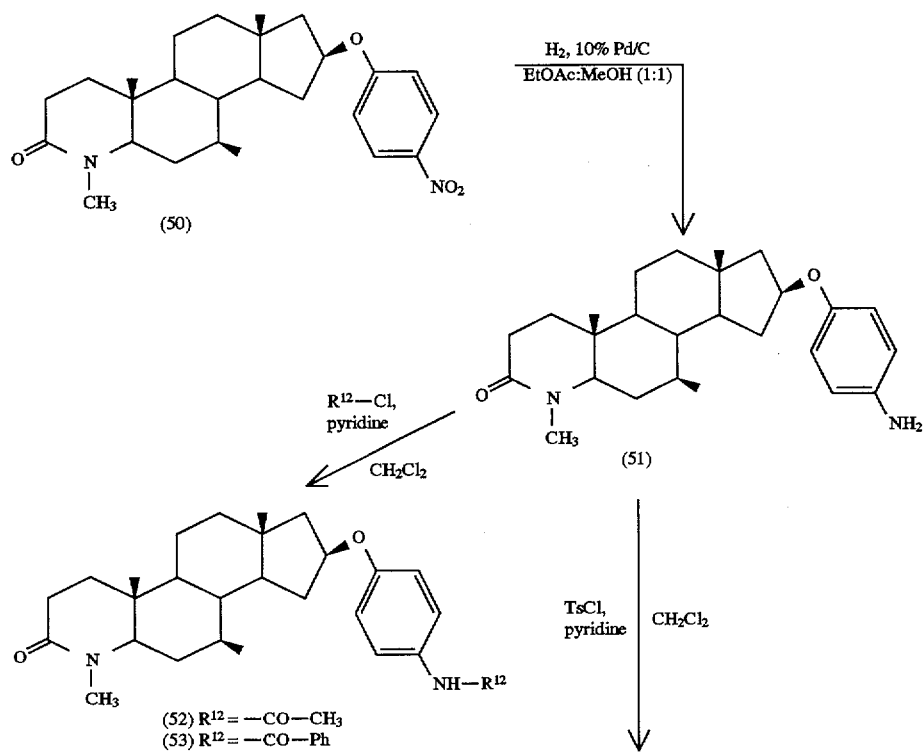

-continued
SCHEME 10
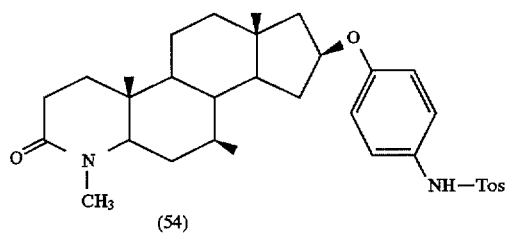
SCHEME 11
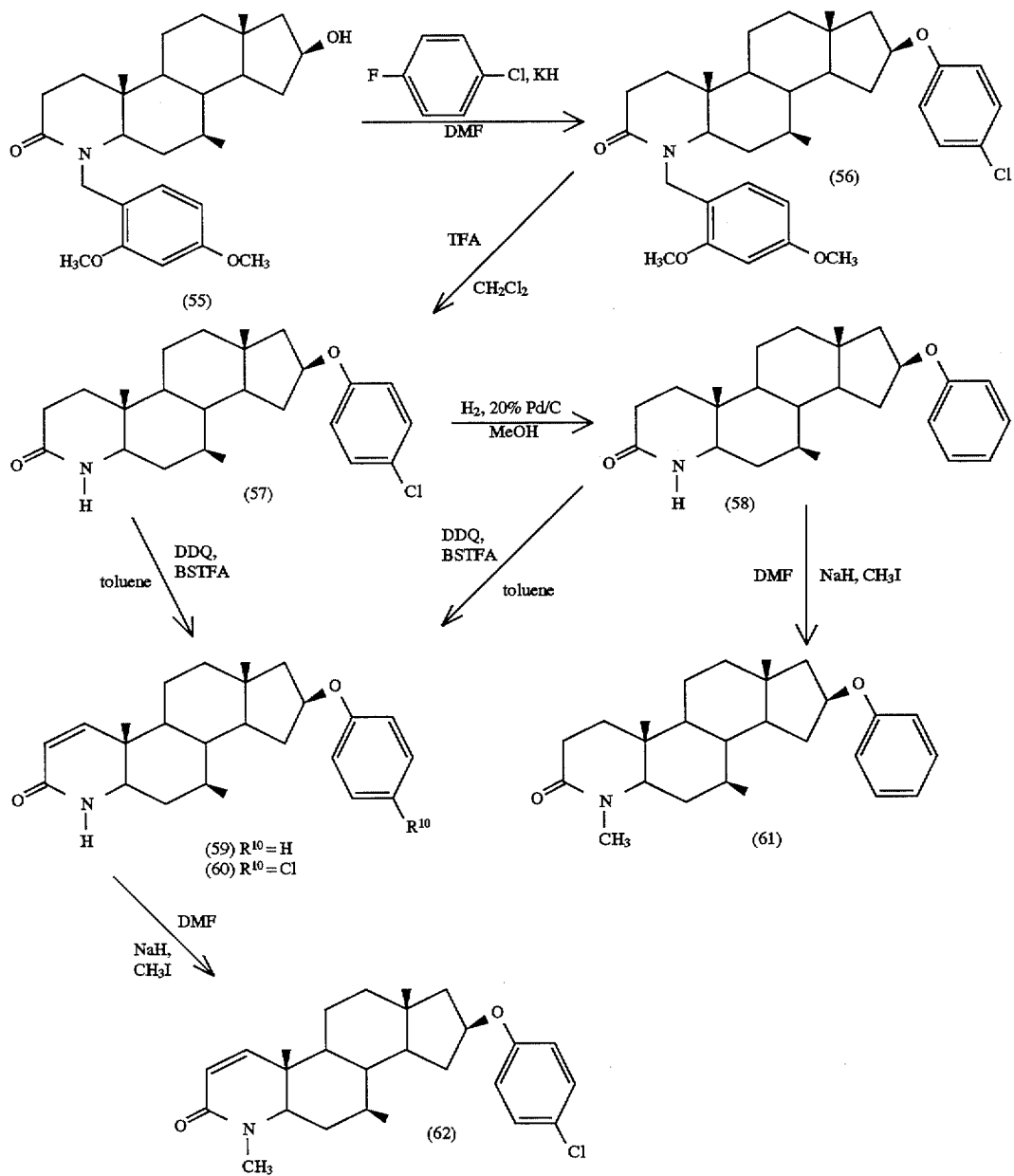

SCHEME 12
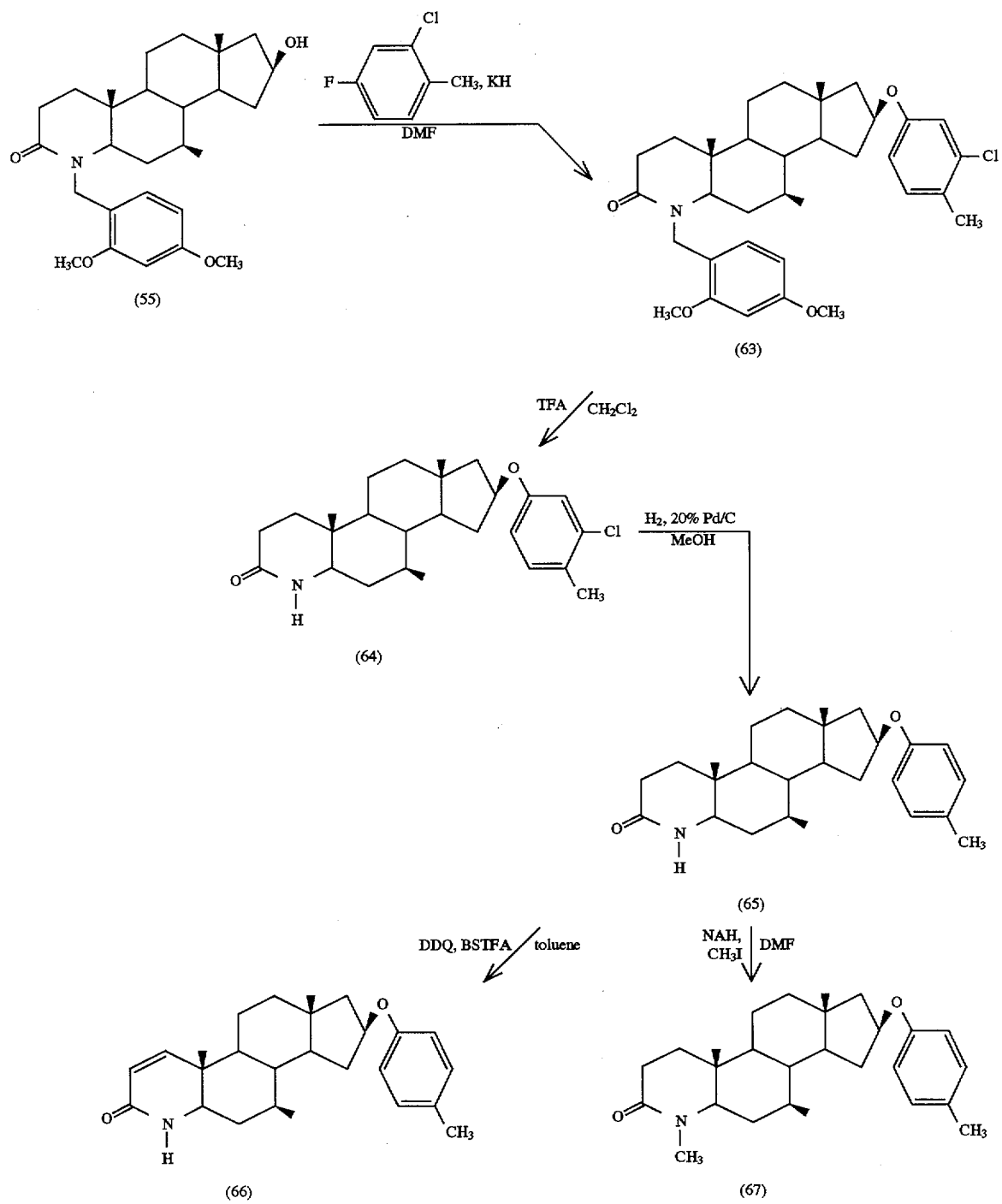

SCHEME 13
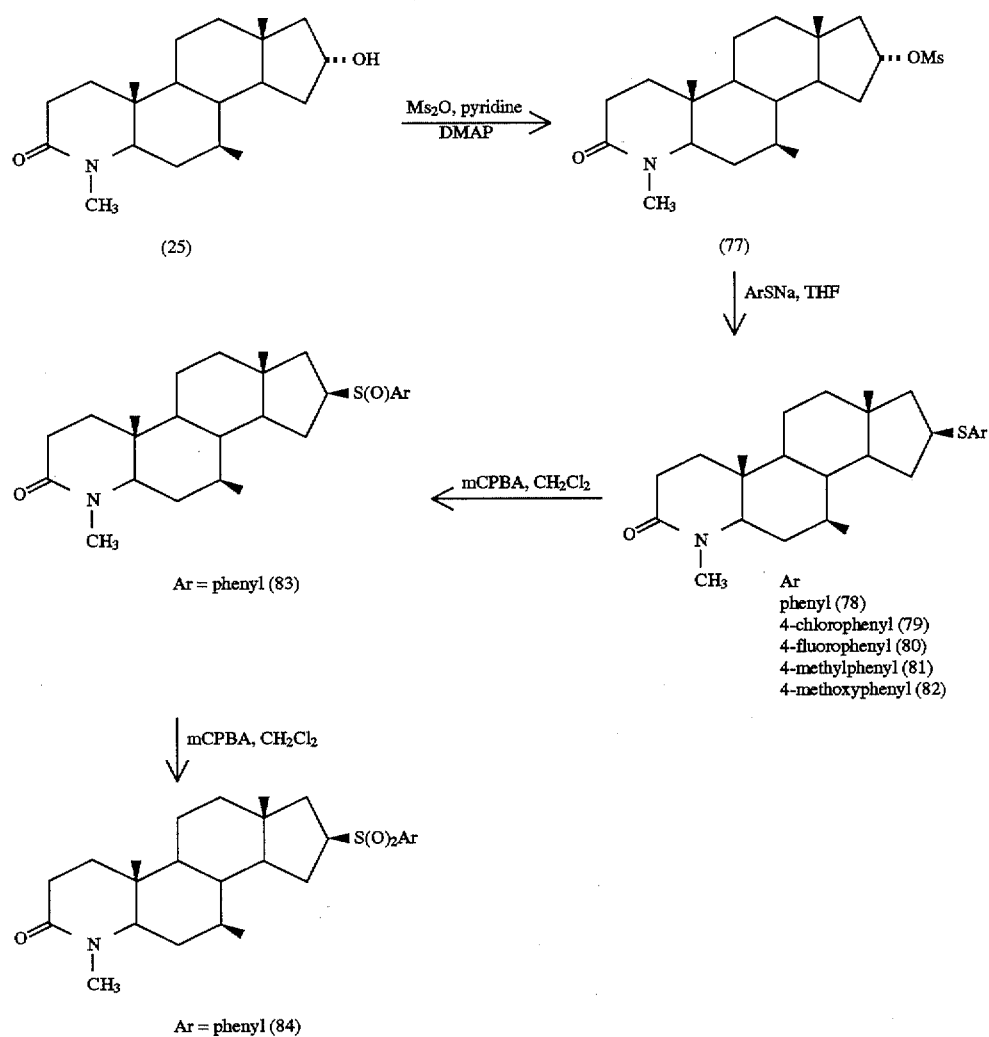
SCHEME 14
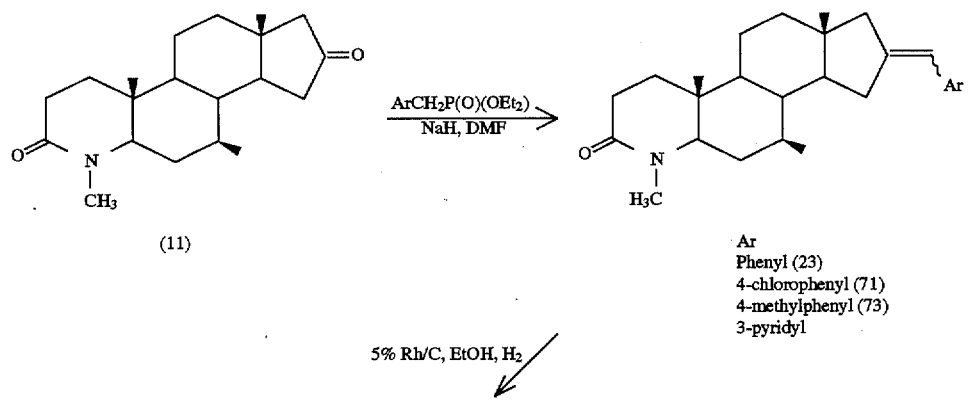

-continued
SCHEME 14

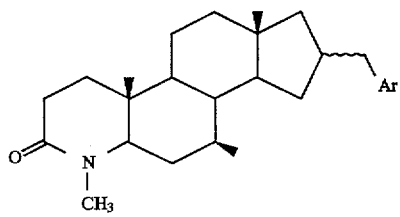

Ar
4-chlorophenyl (74)
2-methylphenyl (75)
3-pyridyl (76)

The following examples are provided to further illustrate details for the preparation of the compounds of the present invention. The examples are not intended to be limitations on the scope of the instant invention in any way, and they should not be so construed. Furthermore, the compounds described in the following examples are not to be construed as forming the only genus that is considered as the invention, and any combination of the compounds or their moieties may itself form a genus. Those skilled in the art will readily understand that known variations of the conditions and processes of the following preparative procedures can be used to prepare these compounds. All temperatures are in degrees Celsius unless noted otherwise.

The starting material 4-aza-4-methyl-5α-androstan-3,17-dione (Compound A in Scheme 1 above) can be made according to the methods described in Rasmusson, et al., *J. Med. Chem.*, 27, p. 1690–1701 (1984). The starting material 4-aza-4,7β-dimethyl-5α-androstan-3,17-dione can be synthesized according to the procedure described in Example 36, below.

EXAMPLE 1

4-Aza-4-methyl-5α-androstan-3,16-dione

Step 1:

4-aza-4-methyl-5α-androstan-3,17-dione-16-oxime

To 2-methyl-2-propanol (14 mL) in a round-bottom flask under a stream of nitrogen gas was added potassium tert-butoxide (740 mg, 6.59 mmol). After complete solution was achieved, 4-aza-4-methyl-5α-androstan-3,17-dione (1.0 g, 3.30 mmol) was added and stirring was continued for 1 hour affording a gold-colored solution. To the reaction mixture was added dropwise with stirring isoamyl nitrite (0.884 mL, 6.58 mmol), and stirring was continued overnight at room temperature affording a deep-orange solution. The mixture was then diluted with an equal volume of water and acidified to pH ~2 with 2N hydrochloric acid. Diethyl ether was added, and the solid that formed was filtered, washed with ether, and dried in vacuo, to yield the title compound.

Step 2:

4-aza-4-methyl-5α-androstan-3-one-16-oxime

To a mixture of 4-aza-4-methyl-5α-androstan-3,17-dione-16-oxime (596 mg, 1.79 mmol) in ethylene glycol (5 mL) were added 98% hydrazine (57 µL, 1.74 mmol) and powdered potassium hydroxide (568 mg, 10.12 mmol). The mixture was heated for 16 h at 140°, cooled, and neutralized with 2N hydrochloric acid. The resulting solid was filtered, washed with water, and dried in vacuo to yield the title compound; mass spectrum: m/z 318(M).

Step 3:

4-aza-4-methyl-5α-androstan-3,16-dione

A mixture of 4-aza-4-methyl-5α-androstan-3-one-16-oxime (218 mg, 0.684 mmol) and sodium bisulfite (249 mg, 23.9 mmol) in 50% aqueous ethanol (10 mL) was heated for 3 h at reflux temperature. Dilute hydrochloric acid (0.5N, 33 mL) and methylene chloride (50 mL) were added, and the mixture was vigorously agitated for several minutes. The organic layer was separated and washed with sodium hydrogencarbonate solution, saturated brine solution, dried ($Na_2SO_4$), and evaporated. The desired product was purified by flash silica gel chromatography using 15% acetone/methylene chloride as eluant to yield the title compound; FAB mass spectrum: m/z 304 (M+1).

400 MHz $^1$H NMR ($CDCl_3$): δ 0.89 (s, 3H); 0.91 (s, 3H); 2.90 (s, 3H); and 3.05 (dd, 1H).

EXAMPLE 2

3-Oxo-4-aza-4-methyl-16β-hydroxy-5α-androstane

A solution of 4-aza-4-methyl-5α-androstan-3,16-dione (100 mg, 0.330 mmol) in methanol (2 mL) was cooled in an ice bath and treated with sodium borohydride (38 mg, 0.989 mmol) for 1 h. The reaction mixture was diluted with water and extracted with methylene chloride (2×20 mL). The combined organic extracts were washed with saturated brine solution, dried ($Na_2SO_4$), and evaporated. The desired product was purified by flash silica gel chromatography using 10% acetone/methylene chloride as eluant to yield the title compound; FAB mass spectrum: m/z 306 (M+1).

400 MHz $^1$H NMR ($CDCl_3$): δ 0.88 (s, 3H); 0.95 (s, 3H); 2.90 (s, 3H); 3.00 (dd, 1H); and 4.39 (m, 1H).

EXAMPLE 3

3-Oxo-4-aza-4-methyl-16β-methoxy-5α-androstane

To a solution of 3-oxo-4-aza-4-methyl-16β-hydroxy-5α-androstane (35 mg, 0.115 mmol) in dimethyl sulfoxide (1.0 mL) was added powdered potassium hydroxide (32 mg, 0.575 mmol). After stirring for 15 min at room temperature under an nitrogen atmosphere, iodomethane (36 µl, 0.575 mmol) was added and stirring was continued for a further 4 hours. The mixture was diluted with diethyl ether (30 mL), which was washed with water, saturated brine solution, dried ($Na_2SO_4$), and evaporated. The desired product was purified by flash silica gel chromatography using 10% acetone/methylene chloride as eluant to yield the title compound; mass spectrum: m/z 391 (M).

400 MHz $^1$H NMR (CDCl$_3$): δ 0.88 (s, 6H); 2.90 (s, 3H); 3.00 (dd, 1H); 3.21 (s, 3H); and 3.83 (m, 1H).

EXAMPLE 4

3-Oxo-4-aza-4-methyl-16β-allyloxy-5α-androstane

This compound was prepared in a similar fashion as Example 3, but substituting allyl bromide in place of iodomethane to yield the title compound; mass spectrum: m/z 345 (M).

400 MHz $^1$H NMR (CDCl$_3$): δ 0.88 (s, 3H); 0.90 (s, 3H); 2.90 (s, 3H); 3.00 (dd, 1H); 3.90 (m, 2H); 3.99 (m, 1H); 5.11–5.27 (m, 2H); and 5.83–5.93 (m, 1H).

EXAMPLE 5

3-Oxo-4-aza-4-methyl-16β-(n-propyloxy)-5α-androstane

A solution of 3-oxo-4-aza-4-methyl-16β-allyloxy-5α-androstane in ethyl acetate (0.85 mL) was hydrogenated at atmospheric pressure in the presence of platinum oxide (4 mg) for 30 min at room temperature. The catalyst was removed by filtration through a Millex-HV 0.45 μm Filter Unit. Purification was achieved by flash silica gel chromatography using 10% acetone/methylene chloride as eluant to yield the title compound; mass spectrum: m/z 348 (M+1).

400 MHz NMR (CDCl$_3$): δ 0.88 (s, 3H); 0.89 (s, 3H); 2.90 (s, 3H); 3.00 (dd, 1H); 3.28 (t, 2H); and 3.92 (m, 1H).

EXAMPLE 6

3-Oxo-4-aza-4-methyl-16β-(acetamido)-5α-androstane

Step 1:

3-Oxo-4-aza-4-methyl-16β-(amino)-5α-androstane

A solution of 4-aza-4-methyl-5α-androstan-3-one-16-oxime (150 mg, 0.471 mmol) in ethanol (15 mL)-acetic acid (7 mL) was hydrogenated at atmospheric pressure in the presence of platinum oxide (50 mg) overnight at room temperature. The catalyst was removed by filtration through a Millex-HV 0.45 μm Filter Unit, and the filtrate was evaporated. The residue was dissolved in methylene chloride (50 mL), and the solution was washed with saturated sodium hydrogencarbonate solution, saturated brine solution, dried (Na$_2$SO$_4$), and evaporated to afford the desired amine.

Step 2:

3-Oxo-4-aza-4-methyl-16β-(acetamido)-5α-androstane

The amine from Step 1 (56 mg, 0.184 mmol) was dissolved in methylene chloride (1.0 mL) and treated with pyridine (0.6 mL), 4-dimethylaminopyridine (5 mg), and acetic anhydride (0.3 mL) for 2 h at room temperature. The mixture was diluted with methylene chloride (50 mL), and the solution was washed with water, 1N hydrochloric acid, saturated sodium hydrogencarbonate solution, saturated brine solution, dried (Na$_2$SO$_4$), and evaporated. The product was purified by flash silica gel chromatography using 2% methanol/methylene chloride as eluant to yield the title compound; mass spectrum: m/z 346 (M).

400 MHz $^1$H NMR (CDCl$_3$): δ 0.82 (s, 3H); 0.87 (s, 3H); 1.93 (s, 3H); 2.90 (s, 3H); 3.00 (dd, 1H); 4.28 (m, 1H); and 5.54 (d, 1H).

EXAMPLE 7

3-Oxo-4-aza-4-methyl-16β-(benzamido)-5α-androstane

This compound was prepared in a similar fashion as Example 6, but substituting benzoyl chloride in place of acetic anhydride to yield the title compound; mass spectrum: m/z 408 (M).

400 MHz $^1$H NMR (CDCl$_3$): δ 0.89 (s, 3H); 0.90 (s, 3H); 2.90 (s, 3H); 3.01 (dd, 1H); 4.48 (m, 1H); and 6.12 (d, 1H).

EXAMPLE 8

3-Oxo-4-aza-4-methyl-16β-(benzylaminocarbonyloxy)-5α-androstane

To a solution of 3-oxo-4-aza-4-methyl-16β-hydroxy-5α-androstane (40 mg, 0.131 mmol) in methylene chloride (2 mL) were added triethylamine (67 μL, 0.481 mmol), 4-dimethylaminopyridine (2 mg), and benzyl isocyanate (50 μL, 0.405 mmol). The reaction mixture was stirred for 48 h at room temperature, evaporated, and then subjected to flash silica gel chromatography using 15% acetone/methylene chloride as eluant to yield the title compound; FAB mass spectrum: m/z 439 (M+1).

400 MHz $^1$H NMR (CDCl$_3$): δ 0.87 (s, 6H); 2.90 (s, 3H); 3.00 (dd, 1H); 4.33 (m, 2H); 4.90 (m, 1H) and 5.11 (m, 1H).

EXAMPLE 9

3-oxo-4-aza-4-methyl-16α-hydroxy-5α-androstane

Step 1:

3-Oxo-4-aza-4-methyl-16β-(4-nitrobenzoyloxy)-5α-androstane

To a solution of 3-oxo-4-aza-4-methyl-16β-hydroxy-5α-androstane (34 mg, 0.0.111 mmol) in dry benzene (1.5 mL) were added triphenylphosphine (35 mg, 0.134 mmol), 4-nitrobenzoic acid (22 mg, 0.134 mmol), and diethyl azodicarboxylate (21 μL, 0.134 mmol). The reaction mixture was heated for one hour at 80° (oil bath temperature) under a nitrogen atmosphere. After removal of the benzene by evaporation under diminished pressure, the crude product mixture was subjected to flash silica gel chromatography using 2% methanol/methylene chloride as eluant to give desired product contaminated with some triphenylphosphine (97 mg) which was saponified as described in Step 2.

Step 2:

3-Oxo-4-aza-4-methyl-16α-hydroxy-5α-androstane

The crude product from Step 1 (97 mg) was suspended in ethanol (0.5 mL) and treated with 0.4N sodium hydroxide (0.36 mL, 0.144 mmol). After stirring 90 min at room temperature, the reaction mixture was neutralized with several drops of glacial acetic acid, extracted with ethyl acetate (2×20 mL), washed with water (20 mL), saturated brine solution, dried (sodium sulfate), and evaporated. The product was obtained pure by flash silica gel chromatography using 20% acetone/methylene chloride as eluant; mass spectrum: m/z 305M.

400 MHz $^1$H NMR (CDCl$_3$): δ 0.70 (s, 3H); 0.85 (s, 3H); 2.90 (s, 3H); 3.02 (dd, 1H); and 4.47 (m, 1H).

EXAMPLE 10

3-Oxo-4-aza-4-methyl-16α-methoxy-5α-androstane

To a solution of 3-oxo-4-aza-4-methyl-16β-hydroxy-5α-androstane (20 mg, 0.065 mmol) in dimethyl sulfoxide (0.6 mL) was added powdered potassium hydroxide (18 mg, 0.325 mmol). After stirring for 15 min at room temperature under an nitrogen atmosphere, iodomethane (20 µl, 0.325 mmol) was added and stirring was continued overnight at room temperature. The mixture was diluted with diethyl ether (25 mL), which was washed with water (2×10 mL), dried ($Na_2SO_4$), and evaporated. The desired product was purified by flash silica gel chromatography using 10% acetone/methylene chloride as eluant to yield the title compound; mass spectrum: m/z 319 (M).

400 MHz $^1$H NMR ($CDCl_3$): δ 0.70 (s, 3H); 0.87 (s, 3H); 2.90 (s, 3H); 3.01 (dd, 1H); 3.22 (s, 3H); and 3.92 (m, 1H).

EXAMPLE 11

4-Aza-4,7β-dimethyl-5α-androstan-3,16-dione

Step 1:

4-aza-4,7β-dimethyl-5α-androstan-3,17-dione-16-oxime

To 2-methyl-2-propanol (28 mL) in a round-bottom flask under a stream of nitrogen gas was added potassium tert-butoxide (1.35 g, 12.1 mmol). After complete solution was achieved, 4-aza-4,7β-dimethyl-5α-androstan-3,17-dione (1.92 g, 6.0 mmol) was added and stirring was continued for 1 hour affording a gold-colored solution. To the reaction mixture was added dropwise with stirring isoamyl nitrite (1.63 mL, 12.1 mmol), and stirring was continued overnight at room temperature affording a deep-orange solution. The mixture was then diluted with an equal volume of water, acidified to pH ~2 with 2N hydrochloric acid, and extracted with diethyl ether (3×50 mL). The combined ether extracts were washed with saturated brine solution, dried (sodium sulfate), and evaporated. The crude product was subjected to flash silica gel chromatography using 5% methanol/methylene chloride as eluant to yield the title compound.

Step 2:

4-aza-4,7β-dimethyl-5α-androstan-3-one-16-oxime

To a mixture of 4-aza-4,7β-dimethyl-5α-androstan-3,17-dione-16-oxime (2.7 g, 7.79 mmol) in ethylene glycol (30 mL) were added 98% hydrazine (0.27 mL, 8.57 mmol) and powdered potassium hydroxide (2.62 g, 46.8 mmol). The mixture was heated for 3 h at 140°, cooled, diluted with water (100 mL), neutralized with concentrated hydrochloric acid to give a tan precipitate that was filtered and dried (1.7 g). Flash silica gel chromatography of this material using initially 2% methanol/methylene chloride and subsequently 5% methanol/methylene chloride as eluant gave pure product.

Step 3:

4-aza-4,7β-dimethyl-5α-androstan-3,16-dione

A mixture of 4-aza-4,7β-dimethyl-5α-androstan-3-one-16-oxime (0.55 g, 1.65 mmol) in 60% acetic acid (20 mL) was heated at reflux temperature for 48 hours. The cooled mixture was diluted with water (25 mL) and extracted with methylene chloride (3×50 mL). The combined extracts were washed with saturated sodium hydrogen-carbonate solution, dried (sodium sulfate), and evaporated. Flash silica gel chromatography using 2% methanol/methylene chloride afforded pure product; mass spectrum: m/z 317 (M).

400 MHz $^1$H NMR ($CDCl_3$): δ 0.88 (s, 3H); 0.89 (s, 3H); 1.00 (d, 3H); 2.90 (s, 3H); and 3.07 (dd, 1H).

EXAMPLE 12

3-Oxo-4-aza-4,7β-dimethyl-16β-hydroxy-5α-androstane

A solution of 4-aza-4,7β-dimethyl-5α-androstan-3,16-dione (390 mg, 1.23 mmol) in methanol (8 mL) was cooled in an ice bath and treated with sodium borohydride (140 mg, 3.68 mmol) for 30 min. The reaction mixture was diluted with water and extracted with methylene chloride (3×50 mL). The combined organic extracts were washed with saturated brine solution, dried ($Na_2SO_4$), and evaporated. The desired product was purified by flash silica gel chromatography using initially 10% acetone/methylene chloride and subsequently 20% acetone/methylene chloride as eluant to yield the title compound; mass spectrum: m/z 391 (M).

400 MHz $^1$H NMR ($CDCl_3$): δ 0.83 (s, 3H); 0.96 (s, 3H); 1.03 (d, 3H); 2.90 (s, 3H); 3.00 (dd, 1H); and 4.36 (m, 1H).

EXAMPLE 13

3-Oxo-4-aza-4,7β-dimethyl-16β-methoxy-5α-androstane

To a solution of 3-oxo-4-aza-4,7β-dimethyl-16β-hydroxy-5α-androstane (20 mg, 0.0.063 mmol) in dimethyl sulfoxide (0.5 mL) was added powdered potassium hydroxide (18 mg, 0.313 mmol). After stirring for 15 min at room temperature under an nitrogen atmosphere, iodomethane (20 µl, 0.313 mmol) was added and stirring was continued overnight at room temperature. The mixture was diluted with diethyl ether (25 mL), which was washed with water, saturated brine solution, dried ($Na_2SO_4$), and evaporated. The desired product was purified by flash silica gel chromatography using 1.5% methanol/methylene chloride as eluant to yield the title compound; mass spectrum: m/z 334 (M+1).

400 MHz $^1$H NMR ($CDCl_3$): δ 0.83 (s, 3H); 0.89 (s, 3H); 1.03 (d, 3H); 2.90 (s, 3H); 3.00 (dd, 1H); 3.24 (s, 3H); and 3.80 (m, 1H).

EXAMPLE 14

3-Oxo-4-aza-4,7β-dimethyl-16β-ethyloxy-5α-androstane

This compound was prepared in a similar fashion as Example 13, but substituting iodoethane in place of iodomethane and potassium hydride in N,N-dimethylformamide in place of potassium hydroxide in dimethyl surf oxide; mass spectrum: m/z 347 (M).

400 MHz $^1$H NMR ($CDCl_3$): δ 0.83 (s, 3H); 0.90 (s, 3H); 1.03 (d, 3H); 1.18 (t, 3H); 2.90 (s, 3H); 3.00 (dd, 1H); 3.39 (m, 2H); and 4.40 (m, 1H).

EXAMPLE 15

3-Oxo-4-aza-4,7β-dimethyl-16β-allyloxy-5α-androstane

This compound was prepared in a similar fashion as Example 13, but substituting allyl bromide in place of iodomethane; mass spectrum: m/z 359 (M).

400 MHz $^1$H NMR ($CDCl_3$): δ 0.83 (s, 3H); 0.91 (s, 3H); 1.04 (d, 3H); 2.90 (s, 3H); 3.00 (dd, 1H); 3.90 (m, 2H); 3.96 (m, 1H); 5.11–5.29 (m, 2H); and 5.85–5.93 (m, 1H).

EXAMPLE 16

3-Oxo-4-aza-4,7β-dimethyl-16β-benzyloxy-5α-androstane

This compound was prepared in a similar fashion as Example 14, but substituting benzyl bromide in place of iodoethane; mass spectrum: m/z 409 (M).

400 MHz $^1$H NMR ($CDCl_3$): δ 0.85 (s, 3H); 0.95 (s, 3H); 1.04 (d, 3H); 2.90 (s, 3H); 3.00 (dd, 1H); 4.01 (m, 1H); 4.43 (q, 2H); and 7.31 (m, 5H).

EXAMPLE 17

3-Oxo-4-aza-4,7β-dimethyl-16β-(3,3-dimethylallyloxy)-5α-androstane

This compound was prepared in a similar fashion as Example 13 but substituting 3,3-dimethylallyl bromide in place of iodomethane;

400 MHz $^1$H NMR (CDCl$_3$): δ 0.82 (s, 3H); 0.90 (s, 3H); 1.02 (d, 3H); 1.67 (s, 3H); 1.71 (s, 3H); 2.90 (s, 3H); 3.00 (dd, 1H); 3.93 (m, 1H); and 5.31 (m, 1H).

EXAMPLE 18

3-Oxo-4-aza-4,7β-dimethyl-16β-(n-propyloxy)-5α-androstane

A solution of 3-oxo-4-aza-4,7β-dimethyl-16β-allyloxy-5α-androstane (13.0 mg, 0.036 mmol) in ethyl acetate (0.5 mL) was hydrogenated at atmospheric pressure in the presence of platinum oxide (4 mg) for 30 min at room temperature. The catalyst was removed by filtration through a Millex-HV 0.45 μm Filter Unit. Purification was achieved by flash silica gel chromatography using 1% methanol/methylene chloride as eluant to yield the title compound; mass spectrum: m/z 361 (M).

400 MHz $^1$H NMR (CDCl$_3$): δ 0.82 (s, 3H); 0.89 (s, 3H); 0.89 (t, 3H); 1.05 (d, 3H); 2.90 (s, 3H); 3.00 (dd, 1H); 3.29 (t, 2H); and 3.89 (m, 1H).

EXAMPLE 19

3-Oxo-4-aza-4,7β-dimethyl-16β-(3-methyl-1-butyloxy)-5α-androstane

A solution of 3-oxo-4-aza-4,7β-dimethyl-16β-(3,3-dimethylallyloxy)-5α-androstane (12 mg) in ethyl acetate (0.5 mL) was hydrogenated at atmospheric pressure in the presence of 10% palladium-on-charcoal (3 mg) for 30 min at room temperature. The catalyst was removed by filtration through a Millex-HV 0.45 μm Filter Unit. Purification was achieved by flash silica gel chromatography using 2% methanol/methylene chloride as eluant to yield the title compound; mass spectrum: m/z 389M.

400 MHz $^1$H NMR (CDCl$_3$): δ 0.82 (s, 3H); 0.88 (s, 3H); 1.03 (d, 3H); 2.90 (s, 3H); 3.00 (dd, 1H); 3.33 (m, 2H); and 3.88 (m, 1H).

EXAMPLE 20

3-Oxo-4-aza-4,7β-dimethyl-16β-(t-butoxy)-5α-androstane

To a solution of 3-oxo-4-aza-4,7β-dimethyl-16β-hydroxy-5α-androstane (20 mg, 0.063 mmol) in methylene chloride (0.5 mL) cooled in an ice-bath were added t-butyl trichloroacetimidate (23 μL, 0.126 mmol) and trifluoromethanesulfonic acid (0.56 μL, 0.0063 mmol). The reaction mixture was allowed to reach room temperature, and after one hour additional amounts of t-butyl trichloroacetimidate (23 μL) and trifluoromethanesulfonic acid (0.56 μL) were added. After one hour, a third addition of each reagent was made, and the reaction mixture was stirred for 5 h at room temperature. The mixture was diluted with diethyl ether (50 mL), washed with 1N aqueous sodium hydroxide (10 mL), 1N hydrochloric acid (10 mL), saturated sodium hydrogencarbonate solution, dried (sodium sulfate), and evaporated. The crude product was purified by flash silica gel chromatography using 10% acetone/methylene chloride as eluant to yield the title compound; mass spectrum: m/z 375 (M).

400 MHz $^1$H NMR (CDCl$_3$): δ 0.82 (s, 3H); 0.90 (s, 3H); 1.03 (d, 3H); 1.11 (s, 9H); 2.90 (s, 3H); 3.00 (dd, 1H); and 4.00 (m, 1H).

EXAMPLE 21

3-Oxo-4-aza-4,7β-dimethyl-16β-(4-cyanophenoxy)-5α-androstane

To a solution of 3-oxo-4-aza-4,7β-dimethyl-16β-hydroxy-5α-androstane (20 mg, 0.063 mmol) in N,N-dimethylformamide (0.5 mL) was added powdered potassium hydride (35 weight %) (15 mg, 0.126 mmol). After stirring for 15 min at room temperature under an nitrogen atmosphere, 4-fluorobenzonitrile (38 mg, 0.315 mmol) was added and stirring was continued for 2 hours at room temperature. The mixture was diluted with methylene chloride (25 mL) and quenched in ice-water. The aqueous layer was extracted with methylene chloride (3×25 mL) and the combined organic layers were washed with saturated brine solution, dried (sodium sulfate) and evaporated. The desired product was purified by flash silica gel chromatography using initially 1.5% methanol/methylene chloride and subsequently 2% methanol/methylene chloride as eluant to yield the title compound; mass spectrum: m/z 420 (M).

400 MHz $^1$H NMR (CDCl$_3$): δ 0.86 (s, 3H); 0.92 (s, 3H); 1.134 (d, 3H); 2.90 (s, 3H); 3.02 (dd, 1H); 4.76 (m, 1H); 6.87 (m, 2H); and 7.53 (m, 2H).

EXAMPLE 22

3-Oxo-4-aza-4,7β-dimethyl-16β-(4-trifluoromethylphenoxy)-5α-androstane

This compound was prepared in a similar fashion as Example 21, but substituting 4-fluorobenzotrifluoride in place of 4-fluorobenzonitrile; mass spectrum: m/z 463 (M).

400 MHz $^1$H NMR (CDCl$_3$): δ 0.85 (s, 3H); 0.93 (s, 3H); 1.04 (d, 3H); 2.90 (s, 3H); 3.02 (dd, 1H); 4.76 (m, 1H); 6.88 (d, 2H); and 7.50 (d, 2H).

EXAMPLE 23

3-Oxo-4-aza-4,7β-dimethyl-16β-(4-chlorophenoxy)-5α-androstane

This compound was prepared in a similar fashion as Example 21, but substituting 1-chloro-4-fluorobenzene in place of 4-fluorobenzonitrile; mass spectrum: m/z 430 (M+1).

400 MHz $^1$H NMR (CDCl$_3$): δ 0.85 (s, 3H); 0.93 (s, 3H); 1.03 (d, 3H); 2.90 (s, 3H); 3.02 (dd, 1H); 5.28 (m, 1H); 6.74 (d, 2H); and 7.19 (d, 2H).

EXAMPLE 24

3-Oxo-4-aza-4,7β-dimethyl-16β-(4-fluorophenoxy)-5α-androstane

This compound was prepared in a similar fashion as Example 21, but substituting 1,4-difluorobenzene in place of 4-fluorobenzonitrile; mass spectrum: m/z 414 (M+1).

400 MHz $^1$H NMR (CDCl$_3$): δ 0.85 (s, 3H); 0.94 (s, 3H); 1.04 (d, 3H); 2.91 (s, 3H); 3.02 (dd, 1H); 4.65 (m, 1H); 6.75 (m, 2H); and 6.92 (m, H).

EXAMPLE 25

3-Oxo-4-aza-4,7β-dimethyl-16α-hydroxy-5α-androstane

Step 1:

3-Oxo-4-aza-4,7β-dimethyl-16α-(4-nitrobenzoyloxy)-5α-androstane

To a solution of 3-oxo-4-aza-4,7β-dimethyl-16β-hydroxy-5α-androstane (178 mg, 0.560 mmol) in dry benzene (10 mL) were added triphenylphosphine (294 mg, 1.12 mmol), 4-nitrobenzoic acid (187 mg, 1.12 mmol), and diethyl azodicarboxylate (176 µL, 1.12 mmol). The reaction mixture was heated for one hour at 80° (oil bath temperature) under a nitrogen atmosphere. After removal of the benzene by evaporation under diminished pressure, the crude product mixture was subjected to flash silica gel chromatography using 2% methanol/methylene chloride as eluant to give desired product contaminated with some triphenylphosphine (404 mg) which was saponified as described in Step 2.

400 MHz $^1$H NMR (CDCl$_3$): δ 0.80 (s, 3H); 0.88 (s, 3H); 1.03 (d, 3H); 2.90 (s, 3H); 3.05 (dd, 1H); and 5.48 (m, 1H).

Step 2:

3-Oxo-4-aza-4,7β-dimethyl-16α-hydroxy-5α-androstane

The crude product from Step 1 (404 mg) was suspended in ethanol (5 mL) and treated with 0.4N sodium hydroxide (1.82 mL, 0.728 mmol). After stirring 90 min at room temperature, the reaction mixture was neutralized with several drops of glacial acetic acid, extracted with ethyl acetate (100 mL), washed with water (2×25 mL), saturated brine solution, dried (sodium sulfate), and evaporated. The product was obtained pure by flash silica gel chromatography using 20% acetone/methylene chloride as eluant; mass spectrum: m/z 319 (M).

400 MHz $^1$H NMR (CDCl$_3$): δ 0.71 (s, 3H); 0.82 (s, 3H); 1.02 (d, 3H); 2.90 (s, 3H); 3.03 (dd, 1H); and 4.42 (m, 1H).

EXAMPLE 26

3-Oxo-4-aza-4,7β-dimethyl-16α-(n-propyloxy)-5α-androstane

To a solution of 3-oxo-4-aza-4,7β-dimethyl-16α-hydroxy-5α-androstane (20 mg, 0.063 mmol) in N,N-dimethylformamide (0.65 mL) was added potassium hydride (35 weight %) (15 mg, 0.126 mmol). After stirring for 15 min at room temperature under a nitrogen atmosphere, allyl bromide (27 µl, 0.315 mmol) was added and stirring was continued for 2 h. Additional amounts of potassium hydride (15 mg) and allyl bromide (27 µL) were added, and stirring was continued overnight. The mixture was diluted with diethyl ether (50 mL) and water (10 mL). The organic layer was washed with 1N hydrochloric acid (10 mL), water (10 mL), saturated brine solution, dried (Na$_2$SO$_4$), and evaporated. The desired product was purified by flash silica gel chromatography using 2% methanol/methylene chloride as eluant. This material was hydrogenated in ethyl acetate (0.5 mL) in the presence of 10% palladium-on-charcoal for 2 hours. The catalyst was removed by filtration through a Millex-HV 0.45 µm Filter Unit. Purification was achieved by flash silica gel chromatography using 10% isopropanol/hexane as eluant to yield the title compound; mass spectrum: m/z 361 (M).

400 MHz $^1$H NMR (CDCl$_3$): δ 0.76 (s, 3H); 0.82 (s, 3H); 0.90 (t, 3H); 1.02 (d, 3H); 2.90 (s, 3H); 3.02 (dd, 1H); 3.29 (t, 2H); and 3.98 (m, 1H).

EXAMPLE 27

3-Oxo-4-aza-4,16α-dimethyl-16β-hydroxy-5α-androstane

To a solution of 4-aza-4-methyl-5α-androstan-3,16-dione (50 mg, 0.165 mmol) cooled to −40° was added dropwise with stirring methylmagnesium bromide (3.0M solution in diethyl ether) (275 µL, 0.825 mmol). The reaction mixture was allowed to reach room temperature and stirred for 2 h under a nitrogen atmosphere. The reaction was quenched with saturated ammonium chloride solution (25 mL) and extracted with methylene chloride (2×50 mL). The combined organic extracts were washed with saturated brine solution, dried (sodium sulfate) and evaporated. The desired product was obtained pure by flash silica gel chromatography using 2% methanol/methylene chloride as eluant; mass spectrum: m/z 319 (M).

400 MHz $^1$H NMR (CDCl$_3$): δ 0.88 (s, 3H); 0.98 (s, 3H); 1.31 (s, 3H); 2.90 (s, 3H); and 3.00 (dd, 1H).

EXAMPLE 28

3-Oxo-4-aza-4,7β,16α-trimethyl-16β-hydroxy-5α-androstane

This compound was prepared in a similar fashion as Example 27, but substituting 4-aza-4,7β-dimethyl-5α-androstan-3,16-dione in place of 4-aza-4-methyl-5α-androstan-3,16-dione as starting material; mass spectrum: m/z 333 (M).

400 MHz $^1$H NMR (CDCl$_3$): δ 0.82 (s, 3H); 0.98 (s, 3H); 1.01 (d, 3H); 1.30 (s, 3H); 2.90 (s, 3H); and 3.00 (dd, 1H).

EXAMPLE 29

3-Oxo-4-aza-4,16α-dimethyl-16β-methoxy-5α-androstane

To a solution of 3-oxo-4-aza-4,16α-dimethyl-16β-hydroxy-5α-androstane (31 mg, 0.097 mmol) in N,N-dimethylformamide (0.5 mL) was added potassium hydride (35 weight %) (23 mg, 0.194 mmol). After stirring for 15 min at room temperature, iodomethane (32 µL, 0.485 mmol) was added, and stirring was continued overnight at room temperature. The reaction mixture was diluted with diethyl ether, washed with 2N hydrochloric acid (10 mL), water (10 mL), saturated brine solution, dried (sodium sulfate), and evaporated. The desired product was obtained pure by flash silica gel chromatography using 2% methanol/methylene chloride as eluant; mass spectrum: m/z 333 (M).

400 MHz $^1$H NMR (CDCl$_3$): δ 0.88 (s, 3H); 0.90 (s, 3H); 1.22 (s, 3H); 2.90 (s, 3H); 3.00 (dd, 1H); and 3.17 (s, 3H).

EXAMPLE 30

3-Oxo-4-aza-4,7β,16α-trimethyl-16β-methoxy-5α-androstane

This compound was prepared in a similar fashion as Example 29, but substituting 3-oxo-4-aza-4,7β,16α-trimethyl-16β-hydroxy-5α-androstane in place of 3-oxo-4-aza-4,16α-dimethyl-1-hydroxy-5α-androstane as starting material; mass spectrum: m/z 347 (M).

400 MHz $^1$H NMR (CDCl$_3$): δ 0.82 (s, 3H); 0.90 (s, 3H); 1.02 (d, 3H); 1.22 (s, 3H); 2.90 (s, 3H); 3.00 (dd, 1H); and 3.18 (s, 3H).

EXAMPLE 31

3-Oxo-4-aza-4,7β-dimethyl-16β-methanethio-5α-androstane

Step 1:

3-Oxo-4-aza-4,7β-dimethyl-16β-(acetylthio)-5α-androstane

A 25-mL round-bottom flask was charged with dry tetrahydrofuran (4 mL) and triphenylphosphine (177 mg, 0.676 mmol) under a nitrogen atmosphere. The flask was cooled in an ice-bath and diisopropyl azodicarboxylate (133 μL, 0.676 mmol) was added, and the mixture was stirred for 30 min at 0°. To the reaction mixture was added a solution of 3-oxo-4-aza-4,7β-dimethyl-16β-hydroxy-5α-androstane (108 mg, 0.338 mmol) and thiolacetic acid (49 μL, 0.676 mmol) in tetrahydrofuran (2.0 mL). The reaction mixture was stirred for 1 h at 0° and then an additional hour at room temperature. The mixture was evaporated and subjected to flash chromatography on silica gel using 10% acetone/methylene chloride as eluant to give the desired product contaminated with some triphenylphosphine. The mixture was used without further purification in Step 2.

400 MHz $^1$H NMR (CDCl$_3$): δ 0.80 (s, 3H); 0.82 (s, 3H); 1.00 (d, 3H); 2.28 (s, 3H); 2.90 (s, 3H); 3.00 (dd, 1H); and 3.80 (m, 1H).

Step 2:

3-Oxo-4-aza-4,7β-dimethyl-16β-(mercapto)-5α-androstane

To a solution of product mixture from Step 1 (208 mg) in ethanol (4.0 mL) was added 0.4N sodium hydroxide (1.8 mL, 0.716 mmol) under a nitrogen atmosphere. The reaction mixture was stirred at room temperature for 1 h, neutralized with several drops of acetic acid, diluted with ethyl acetate (100 mL), washed with water (2×10 mL), saturated brine solution, dried (sodium sulfate), and evaporated. Pure 16-mercaptan was obtained by flash silica gel chromatography using 20% acetone/hexane as eluant.

400 MHz $^1$H NMR (CDCl$_3$): δ 0.82 (s, 3H); 0.93 (s, 3H); 1.02 (d, 3H); 2.90 (s, 3H); 3.00 (dd, 1H); and 3.28 (m, 1H).

Step 3:

3-Oxo-4-aza-4,7β-dimethyl-16β-(methanethio)-5α-androstane

To a solution of 3-oxo-4-aza-4,7β-dimethyl-16β-(mercapto)-5α-androstane (18 mg, 0.054 mmol) in dry tetrahydrofuran (0.5 mL) was added sodium hydride (80% dispersion in mineral oil) (3.2 mg, 0.108 mmol) under a nitrogen atmosphere. After stirring 15 min at room temperature, iodomethane (17 μL, 0.270 mmol) was added, and stirring was continued for 3 h at room temperature. The reaction mixture was diluted with methylene chloride (50 mL), washed with water (10 mL), saturated brine solution, dried (sodium sulfate), and evaporated. Flash silica gel chromatography using 10% isopropanol/hexane as eluant afforded pure desired product; mass spectrum: m/z 349 (M).

400 MHz $^1$H NMR (CDCl$_3$): δ 0.82 (s, 3H); 0.91 (s, 3H); 1.04 (d, 3H); 2.10 (s, 3H); 2.90 (s, 3H); 3.01 (dd, 1H); and 3.08 (m, 1H).

EXAMPLE 32

3-Oxo-4-aza-4,7β-dimethyl-16β-ethanethio-5α-androstane

This compound was prepared in a similar fashion as Example 31, but substituting iodoethane in place of iodomethane in Step 3; mass spectrum: m/z 363 (M).

400 MHz $^1$H NMR (CDCl$_3$): δ 0.82 (s, 3H); 0.91 (s, 3H); 1.03 (d, 3H); 1.24 (t, 3H); 2.57 (q, 2H); 2.90 (s, 3H); 3.00 (dd, 1H); and 3.18 (m, 1H).

EXAMPLE 33

3-Oxo-4-aza-4,7β-dimethyl-16β-(1-propanethio)-5α-androstane

This compound was prepared in a similar fashion as Example 31, but substituting 1-iodopropane in place of iodomethane in Step 3; mass spectrum: m/z 377 (M).

400 MHz $^1$H NMR (CDCl$_3$): δ 0.82 (s, 3H); 0.90 (s, 3H); 0.98 (t, 3H); 1.03 (d, 3H); 2.51 (t, 2H); 2.90 (s, 3H); 3.01 (dd, 1H); and 3.13 (m, 1H).

EXAMPLE 34

3-Oxo-4-aza-4,7β-dimethyl-16β-ethanesulfonyl-5α-androstane

To a solution of 3-oxo-4-aza-4,7β-dimethyl-16β-ethanethio-5α-androstane (17 mg, 0.047 mmol) in methanol (1.0 mL) was added a solution of OXONE, monopersulfate compound (19 mg) in water (1 mL). After stirring 2 h at room temperature, an additional mount of OXONE (19 mg) in water (0.5 mL) was added, and stirring was continued for 10 min. The reaction mixture was diluted with water (25 mL) and extracted with methylene chloride (3×50 mL). The combined organic extracts were washed with saturated brine solution, dried (sodium sulfate), and evaporated. Flash silica gel chromatography using 2% methanol/methylene chloride as eluant afforded pure desired product; mass spectrum: m/z 395 (M).

400 MHz $^1$H NMR (CDCl$_3$): δ 0.85 (s, 3H); 0.92 (s, 3H); 1.03 (d, 3H); 1.39 (t, 3H); 2.91 (s, 3H); 2.99 (q, 2H); 3.00 (dd, 1H); and 3.41 (m, 1H).

EXAMPLE 35

3-Oxo-4-aza-4,7β-dimethyl-16β-fluoro-5α-androstane

To a solution of 3-oxo-4-aza-4,7β-dimethyl-16β-hydroxy-5α-androstane (1 μmg, 0.056 mmol) in methylene chloride (0.5 mL) at room temperature diethylaminosulfur trifluoride (19 μL, 0.144 mmol). After stirring one hour at room temperature, the reaction mixture was diluted with methylene chloride (25 mL), washed with water (25 mL), saturated sodium hydrogencarbonate solution (10 mL), saturated brine solution (10 mL), dried (sodium sulfate), and evaporated. The product was purified by flash silica gel chromatography using 10% acetone/methylene chloride as eluant to yield the title compound; mass spectrum: m/z 321 (M).

400 MHz $^1$H NMR spectrum (CDCl$_3$): δ 0.87 (s, 3H); 0.92 (s, 3H); 1.04 (d, 3H); 2.90 (s, 3H); 3.01 (dd, 1H); and 5.12 (dm, 1H).

EXAMPLE 36

Preparation of 4-aza-4,7β-dimethyl-5α-androstan-3,17-dione (Compound E in Scheme 5 above).

Step 1:

Synthesis of 3-acetoxy-androst-5-en-17-ol

To a solution of 100 mg. (0.303 mmol) of 3-acetoxy-androst-5-en-17-one in 3 ml EtOH at −10° C., was added 22.9 mg (0.606 mmol) of sodium borohydride with stirring.

After the reaction mixture was stirred for one and ½ hours, the mixture was diluted with 10 ml water, the ethanol solvent removed under vacuum, and the residue extracted with ethyl acetate. The organic layer was washed with aqueous $Na_2CO_3$, brine, dried over sodium sulfate and concentrated to leave a residue of crude title compound. Proton NMR confirmed the assigned structure.

Step 2:

Synthesis of 3-acetoxy-androst-5-en-17-ol, 17-t-butyldimethyl-silyl ether

To a solution of the androstan-17-ol, from the previous synthesis being 4.5 g (13.55 mmol) in 50 ml dimethylformamide at 23° C. was added 2.76 g (40–65 mmol) imidazole followed by 3.063 g (20.32 mmol) of t-butyldimethylsilyl chloride. The reaction mixture was stirred and a solid began to precipitate. Twenty additional ml of DMF were added and the mixture further stirred overnight. The mixture was poured into 1 liter water, the solid filtered and washed with water. The solid was dissolved in ethylacetate, the organic layer washed with brine and dried over sodium sulfate, concentrated to yield the silyl protected 17-ol title compound. The proton NMR confirmed the assigned structure.

Step 3:

7-one-17β-ol, 17-t-butyldimethylsilyl ether

To a solution of the TBMS protected 17-ol from the previous synthesis, being 5.6 g (12.55 mmol) in 100 ml acetonitrile at 23° C. was added 90% t-butyl hydrogen peroxide, 3.958 g (43.92 mol), and 138 mg chromium hexacarbonyl. After refluxing the mixture under nitrogen for 24 hours, the reaction mixture was poured into one liter water, solid was filtered, the residue washed with 500 ml water and the residue dissolved in 350 ml methylene chloride. The organic layer was washed with brine, dried over sodium sulfate and concentrated to yield crude material. Thin layer chromatography (3:1 hexane/ethyl acetate on silica gel) showed the presence of starting material. The solid was purified by column chromatography over silica gel by elution with 7% ethyl acetate/hexane to yield the title compound. Proton NMR confirmed the assigned structure.

Step 4:

Synthesis of 3,7-dihydroxy-7-methyl-androst-5-en-17β-ol, 17-t-butyldimethylsilyl ether To a solution of the product from the previous synthesis, being 440 mg (0.956 mmol) in dry tetrahydrofuran at 0° C. was added dropwise methyl magnesium chloride over 5–10 minutes. The reaction mixture was then allowed to stir at room temperature for 24 hours, then poured into saturated aqueous ammonium chloride. The THF solvent was removed under vacuum and the aqueous phase extracted with ethyl acetate. The organic layer was washed with brine, dried, concentrated to yield crude product. Proton NMR confirmed the assigned structure of the title compound which was used in the next step without further purification.

Step 5:

Synthesis of 7-methyl-androst-4,6-dien-3-one-17β-ol, 17-t-butyldimethylsilyl ether The above Grignard product, 3.5 g (7.142 mmol) was dissolved in 50 ml toluene/50 ml cyclohexanone and 20 ml of solvent distilled off under vacuum. To this was added 4.54 g aluminum isopropoxide and the reaction mixture refluxed overnight for 15 hours. The mixture was cooled, diluted with ethyl acetate, washed with sodium potassium tanante, brine, and the organic layer was concentrated under vacuum and the residue steam distilled. The residue was extracted with ethyl acetate, washed with brine, dried and purified by column chromatography on silica gel, eluting with 5% EtOAc/hexane to yield the title compound.

Step 6:

Synthesis of 7β-methyl-androst-5-en-3-one-17β-ol, t-butyldimethylsilyl ether To a solution of 370 mg of the product of the previous synthesis, in 5.5 ml ammonia, 1 ml THF, 1 ml toluene, was added 50 mg of metallic lithium in small pieces. After stirring the blue solution for 2 hours, a solution of 1,2-dibromethane in 2 ml THF was added. After stirring the solution at −78° C. for 10 minutes, 250 mg of ammonium chloride was added and the mixture stirred for 10 minutes. The excess ammonia was removed by evaporation under a nitrogen steam. The reaction mixture was diluted with brine, extracted with ethyl acetate. The organic layer was washed with brine, dried and concentrated to yield crude material which was used as such in the next synthesis.

Steep 7:

Synthesis of 7β-methyl-androst-4-en-3-on-17β-ol, t-butyldimethylsilyl ether

To a solution of the product of the previous synthesis, being 432 mg in 4 ml THF was added 150 microliters DBU (1,8-diazabicyclo[5.4,0]undec-7-ene under nitrogen with stirring. The mixture was refluxed for 1.5 hours, then cooled, diluted with $NH_4Cl$ solution. The solvent THF was removed under vacuum and the residue extracted with ethyl acetate. The organic layer was washed with brine, dried and concentrated under reduced pressure to yield crude material. The titled product was purified by chromatography on silica gel using 10% EtOAc/hexane as eluant.

Step 8:

Synthesis of 17β-(t-butyldimethylsilyloxy)-7β-methyl-5-oxo-A-nor-3,5-secoandrostan-3-oic acid To a solution of 884 mg of the product of the previous synthesis in 15 ml t-butyl alcohol at 80° C. was added 248 mg sodium carbonate in 1.5 ml water followed by a drop-wise addition over 15–20 minutes of a mixture of 2.273 g sodium periodate with 16.8 mg potassium permanganate in 8 ml water. The reaction mixture was heated at 80° C. for 2 hours, cooled, filtered, the residue washed with water, and then the extract L-concentrated under vatcure. The extract was acidified with aqueous HCl, extracted with ethyl acetate and the organic layer washed with aqueous $NaHSO_3$, brine, dried and concentrated to yield crude 9. The proton NMR continued the assigned structure.

Step 9:

Synthesis of 4,7β-dimethyl-4-aza-androst-5-en-3-one-17β-ol, t-butyldimethylsilyl ether To a solution of the product of the previous synthesis, 840 mg in 5 ml ethylene glycol, was added 1.5 g sodium acetate and 737 mg methylamine hydrochloride. After stirring the reaction mixture 4 hours at 180° C., the mixture was cooled, diluted with water, extracted with ethyl acetate, dried and concentrated to afford crude title compound. Proton NMR contained the assigned structure.

Step 10:

Synthesis of 4,7β-dimethyl-4-aza-androst-5-en-3-one-17β-ol

To a solution of 700 mg of the product of the previous example, in 20 ml of acetonitrile at 0° C., was added 500 microliters. aqueous HF. After stirring the reaction mixture for one hour, the HF was neutralized with aqueous sodium carbonate, diluted with water, acetonitrile removed under vacuum, and the residue extracted with ethyl acetate. The organic layer was dried, concentrated to give crude title compound which was further purified by preparative chromatography on silica gel using 3:1 chloroform/acetone.

Step 11:

Synthesis of 4,7β-dimethyl-4-aza-androstan-3-one-17β-ol

To a solution of the product of the previous synthesis, being 350 mg in 10 ml acetic acid was added 100 mg platinum dioxide and the resulting mixture was evacuated and flushed with hydrogen. The reaction was shaken overnight at room temperature under 40 Psig hydrogen pressure. The solution was filtered concentrated. The residue was worked up with ethyl acetate, the organic layer was then concentrated under vacuum, diluted with ethyl acetate, washed with aqueous $NaHCO_3$, brine, dried, concentrated to yield the title compound.

Mass Spec: 320 (M+1).

Step 12:

Synthesis of 4-aza-4,7β-dimethyl-5α-androstan-3,17-dione

The product of the previous synthesis, 1.013 g (3.176 mmol) was placed with 6 ml methylene chloride into a dry flask. Powdered molecular 4 Å sieves, 1.6 g, and 0.558 g (4.76 mmol) of N-methyl-morpholine-N-oxide (NMO) and then tetrapropylammonium perruthanate (TPAP), 55 mg (0.159 mmol) were added. The reaction was stirred for 2 hours, diluted with 150 ml ethyl acetate and filtered. The filtrate was evaporated to dryness to yield crude product which was recrystallized from EtOAc to yield pure product, mp 135°–138° C.

Elemental Analysis Calc'd for $C_{20}H_{31}NO_2$, mw=317.48 Calc'd: C, 75.67; H, 9.84; N, 4.41. Found: C, 75.16; H, 10.22; N, 4.13.

Mass Spec. 318 (M+1).

The following Examples (37 to 49) are prepared in a similar fashion as Example 21, but substituting appropiate 4-fluoro derivatives in place of 4-fluorobenzonitrile.

EXAMPLE 37

3-Oxo-4-aza-4,7β-dimethyl-16β-(4-methylsulfonylphenoxy)-5α-androstane

Mass spectrum: m/z 474 (M+1).

400 MHz $^1$H NMR ($CDCl_3$): δ 0.85 (s, 3H); 0.93 (s, 3H); 1.04 (d, 3H); 2.90 (s, 3H); 3.00 (s, 3H); 4.80 (m,1H); 6.92 (d, 2H); 7.81 (d, 2H).

EXAMPLE 38

3-Oxo-4-aza-4,7β-dimethyl-16β-(3-pyridyloxy)-5α-androstane

Mass spectrum: m/z 397 (M+1).

400 MHz $^1$H NMR ($CDCl_3$): δ 0.85 (s, 3H); 0.94 (s, 3H); 1.04 (d, 3H); 2.91 (s, 3H); 3.02 (dd, 1H); 4.75 (m, 1H); 7.21 (m, 2H); 8.22 (m, 2H).

EXAMPLE 39

3-Oxo-4-aza-4,7β-dimethyl-16β-(4-phenylphenoxy)-5α-androstane

Mass spectrum: m/z 472 (M+1).

400 MHz $^1$H NMR ($CDCl_3$): δ 0.85 (s, 3H); 0.96 (s, 3H); 1.05 (d, 3H); 2.91 (s, 3H); 3.02 (dd, 1H); 4.76 (m, 1H); 6.9 (d, 2H); 7.26 (m, 1H); 7.43 (m, 2H); 7.52 (m, 4H).

EXAMPLE 40

3-Oxo-4-aza-4,7β-dimethyl-16β-(3-chlorophenoxy)-5α-androstane

Mass spectrum: m/z 431(M+1).

400 MHz $^1$H NMR ($CDCl_3$): δ 0.85 (s, 3H); 0.93 (s, 3H); 1.05 (d, 3H); 2.90 (s, 3H); 4.68 (m, 1H); 6.71 (m, 1H); 6.80 (m, 1H); 6.88 (m, 1H); 7.13 (m, 1H).

EXAMPLE 41

3-Oxo-4-aza-4,7β-dimethyl-16β-(4-trifluoromethoxyphenoxy)-5α-androstane

Mass spectrum: m/z 480(M+1).

400 MHz $^1$H NMR ($CDCl_3$): δ 0.85 (s, 3H); 0.94 (s, 3H); 1.04 (d, 3H); 2.91 (s, 3H); 3.02 (dd, 1H); 4.69 (m, 1H); 6.78 (m, 2H); 7.09 (m, 2H).

EXAMPLE 42

3-Oxo-4-aza-4,7β-dimethyl-16β-(2-chlorophenoxy)-5α-androstane

Mass spectrum: m/z 431 (M+1).

400 MHz $^1$H NMR ($CDCl_3$): δ 0.85 (s, 3H); 0.99 (s, 3H); 1.04 (d, 3H); 2.91 (s, 3H); 3.03 (dd, 1H); 4.80 (m, 1H); 6.81 (m, 2H); 7.24 (m, 1H); 7.32 (m, 2H).

EXAMPLE 43

3-Oxo-4-aza-4,7β-dimethyl-16β-(2-pyrazinyloxy)-5α-androstane

Mass spectrum: m/z 398 (M+1).

400 MHz $^1$H NMR ($CDCl_3$): δ 0.85 (s, 3H); 0.95 (s, 3H); 1.04 (d, 3H); 2.90 (s, 3H); 3.02 (dd, 1H); 5.34 (m, 1H); 8.04 (d, 2H); 8.15 (1H).

EXAMPLE 44

3-Oxo-4-aza-4,7β-dimethyl-16β-(2-pyrimidinyloxy)-5α-androstane

Mass spectrum: m/z 398 (M+1).

400 MHz $^1$H NMR ($CDCl_3$): δ 0.85 (s, 3H); 0.95 (s, 3H); 1.04 (d, 3H); 2.90 (s, 3H); 3.02 (dd, 1H); 5.35 (m, 1H); 6.89 (m, 1H); 8.15 (d, 2H).

EXAMPLE 45

3-Oxo-4-aza-4,7β-dimethyl-16β-[4-(1-pyrryl)-phenoxy]-5α-androstane

Mass spectrum: m/z 461 (M+1).

400 MHz $^1$H NMR ($CDCl_3$): δ 0.85 (s, 3H); 0.95 (s, 3H); 1.05 (d, 3H); 2.91 (s, 3H); 4.73 (m, 1H); 6.30 (m, 2H); 6.84 (m, 2H); 6.96 (m, 2H); 7.25 (m, 2H).

EXAMPLE 46

3-Oxo-4-aza-4,7β-dimethyl-16β-(3-cyanophenoxy)-5α-androstane

Mass spectrum: m/z 420 (M).

400 MHz $^1$H NMR (CDCl$_3$): δ 0.85 (s,3H); 0.93 (s, 3H); 1.04 (d, 3H); 2.91 (s, 3H); 3.02 (dd, 1H); 4.71 (m, 1H); 7.05 (m, 2H); 7.22 (m, 1H); 7.32 (m, 1H).

EXAMPLE 47

3-Oxo-4-aza-4,7β-dimethyl-16β-(1-naphthyloxy)-5α-androstane

Mass spectrum: m/z 445 (M).

400 MHz $^1$H NMR (CDCl$_3$): δ 0.86 (s, 3H); 1.03 (s, 3H); 1.07 (d, 3H); 2.92 (s, 3H); 3.02 (dd, 1H); 6.70 (d, 1H); 7.32 (m, 2H); 7.44 (m, 2H); 7.78 (m, 1H); 8.24 (1H).

EXAMPLE 48

3-Oxo-4-aza-4,7β-dimethyl-16β-(3-chloro-4-methylphenoxy)-5α-androstane

Mass spectrum: m/z 445(M+1).

400 MHz $^1$H NMR (CDCl$_3$): δ 0.84 (s, 3H); 0.92 (s, 3H); 1.04 (d, 2H); 2.26 (s, 3H); 2.92 (s, 3H); 4.76 (m, 1H); 6.62 (m, 1H); 6.81 (m, 1H); 7.12 (d, 1H).

EXAMPLE 49

3-Oxo-4-aza-4,7β-dimethyl-16β-[4-(5-oxazolyl)phenoxy]-5α-androstane

Mass spectrum: m/z 463(M+1).

400 MHz $^1$H NMR (CDCl$_3$): δ 0.85 (s, 3H); 0.95 (s, 3H); 1.05 (d, 3H); 2.91 (s, 3H); 4.76 (m, 1H); 6.86 (d, 2H); 7.21 (s, 1H); 7.53 (d, 2H); 7.84 (s, 1H).

EXAMPLE 50

3-oxo-4-aza-4,7β-dimethyl-16β-(4-nitrophenoxy-5α-androstane

This compound was prepared in a similar fashion as Example 21, but substituting 1-fluoro-4-nitrobenzene in place of 4-fluorobenzonitrile; 400 MHz $^1$H NMR (CDCl$_3$): δ 0.85 (s, 3H); 0.94 (s, 3H); 1.05 (d, 3H); 2.92 (s, 3H); 3.03 (dd, 1H); 4.81 (q, 1H); 6.87 (d, 2H); 8.17 (d, 2H).

EXAMPLE 51

3-oxo-4-aza-4,7β-dimethyl-16β-(4-aminophenoxy)-5α-androstane

To a solution of 3-oxo-4-aza-4,7β-dimethyl-16β-(4-aminophenoxy)-5α-androstane (163 mg, 0.36 mmol) in ethylacetate (8 mL) and methanol (8 mL) was added 10% Pd on carbon (25 mg, 0.23 mmol). It was then stirred for four hours under a hydrogen atmosphere at room temperature. It was then filtered through celite and evaporated to afford 148 mg of the title compound. No purification was needed. Mass spectrum: m/z 411 (M+1). 400 MHz $^1$H NMR (CDCl$_3$): δ 0.84 (s, 3H); 0.94 (s, 3H); 1.37 (d, 3H); 2.90 (s, 3H); 3.03 (dd, 1H); 4.64 (q, 1H); 6.70 (d, 2H); 6.78 (d, 2H).

EXAMPLE 52

3-oxo-4-aza-4,7β-dimethyl-16β-(4-acetylaminophenoxy)-5α-androstane

To a solution of 3-oxo-4-aza-4,7β-dimethyl-16β-(4-aminophenoxy)-5α-androstane (48 mq, 0.116 mmol) in methylene chloride (1 mL) and pyridine (0.037 ml, 0.46 mmol) was added acetic anhydride (0.022 mL, 0.23 mmol) and DMAP (5 mg, 0.04 mmol). The reaction was stirred overnight at room temperature under a nitrogen atmosphere. It was then diluted with methylene chloride (50 mL), washed with water (50 mL) and brine (50 mL). The organic phase was then dried over sodium sulfate and evaporated. The crude product was purified by preparative TLC (silica gel, 1000 microns) using 5% methanol/methylene chloride to give 51 mg of the title compound. Mass spectrum: m/z 453 (M+1). 400 MHz 1H NMR (CDCl$_3$): δ 0.84 (s, 3H); 0.93 (s, 3H); 1.04 (d, 3H); 2.13 (s, 3H); 2.92 (s, 3H); 3.03 (dd, 1H); 4.68 (q, 1H); 6.76 (d, 2H); 7.11 (s, 1H); 7.33 (d, 2H).

EXAMPLE 53

3-oxo-4-aza-4,7β-dimethyl-16β-(4-benzoylaminophenoxy)-5α-androstane

This compound was prepared in a similar fashion as Example 52, but substituting benzoyl chloride in place of acetic anhydride, triethylamine in place of pyridine and DMAP was not used; mass spectrum: m/z 515 (M+1). 400 MHz $^1$H NMR (CDCl$_3$): δ 0.84 (s, 3H); 0.94 (s, 3H); 1.05 (d, 3H); 2.92 (s, 3H); 3.04 (dd, 1H); 4.73 (q, 1H); 6.82 (d, 2H); 7.49 (m, 5H); 7.72 (s, 1H); 7.84 (d, 2H).

EXAMPLE 54

3-oxo-4-aza-4,7β-dimethyl-16β-(4-methylsulfonamidophenoxy)-5α-androstane

This compound was prepared in a similar fashion as Example 52, but substituting tosyl chloride in place of acetic anhydride; mass spectrum: m/z 565 (M+1). 400 MHz $^1$H NMR (CDCl$_3$): δ 0.84 (s, 3H); 0.93 (s, 3H); 1.03 (d, 3H); 2.37 (s, 3H); 2.92 (s, 3H); 3.02 (dd, 1H); 4.63 (q, 1H); 6.34 (s, 1H); 6.67 (d, 2H); 6.91 (d, 2H); 7.19 (d, 2H); 7.56 (d, 2H).

EXAMPLE 55

3-oxo-4-aza-4-(2,4-dimethoxybenzyl)-7β-methyl-16β-hydroxy-5α-androstane

The compound 55 was prepared in a similar fashion as compound 12 described in the Scheme 5, except that the corresponding benzyl analog of (Compound E in Scheme 5) was made via similar synthesis of Example 36, in which 2,4-dimethoxy-benzylamine was used in place of methylamine.

EXAMPLE 56

3-oxo-4-aza-4-(2,4-dimethoxybenzyl)-7β-methyl-16β-(4-chlorophenoxy)-5α-androstane This compound was prepared in a similar fashion as Example 23, but substituting 3-oxo-4-aza-4-(2,4-dimethoxy benzyl)-7β-methyl-16β-hydroxy-5α-androstane in place of 3-oxo-4-aza-4,7β-dimethyl-16β-hydroxy-5α-androstane. No purification was done prior to the next reaction.

EXAMPLE 57

3-oxo-4-aza-7β-methyl-16β-(4-chlorophenoxy)-5α-androstane

To a solution of 3-oxo-4-aza-4-(2,4-dimethoxy benzyl)-7β-methyl-16β-(4-chlorophenoxy)-5α-androstane (130 mg, 0.23 mmol) in methylene chloride (1 mL) was added trifluoroacetic acid (1 mL). The reaction was stirred overnight at room temperature. Then the solvent was evaporated and the residue taken up in methylene chloride. The organic phase was washed with saturated sodium bicarbonate and brine. It was then dried over sodium sulfate and evaporated. The crude compound was purified by preparative TLC (silica gel, 1000 microns) using 20% acetone/methylene chloride to yield the title compound. 400 MHz $^1$H NMR (CDCl$_3$): δ 0.86 (s, 3H); 0.93 (s, 3H); 1.01 (d, 3H); 3.07 (dd, 1H); 4.67 (q, 1H); 5.49 (s, 1H); 6.73 (d, 2H); 7.18 (d, 2H).

EXAMPLE 58

3-oxo-4-aza-7β-methyl-16β-phenoxy-5α-androstane

To a solution of 3-oxo-4-aza-7β-methyl-16β-(4-chlorophenoxy)-5α-androstane in methanol was added 20% Pd on carbon. This solution was shaken under a hydrogen atmosphere at 48 psig for one day. It was then filtered through celite and evaporated. The crude compound was then purified by flash silica gel chromatography using 20% acetone/methylene chloride to elute the title compound. 400 MHz $^1$H NMR (CDCl$_3$): δ 0.86 (s, 3H); 0.95 (s, 3H); 1.01 (d, 2H); 3.08 (dd, 1H); 4.71 (q, 1H); 5.48 (s, 1H); 6.81 (d, 2H); 6.89 (t, 1H); 7.24 (t, 2H).

EXAMPLE 59

3-oxo-4-aza-7β-methyl-16β-phenoxy-5α-androst-1-ene

To a solution of 3-oxo-4-aza-7β-methyl-16β-phenoxy-5α-androstane (145 mg, 0.35 mmol) in toluene (3 mL) was added DDQ (95 mg, 0.42 mmol), BSTFA (360 mg, 1.4 mmol) and triflic acid (4.04 mg, 0.027 mmol). This solution was stirred overnight at room temperature under a nitrogen atmosphere. Then methylacetoacetate (4.06 mg, 0.035 mmol) was added and the solution was stirred. After one hour, the reaction was refluxed overnight. It was then poured into water (75 mL) containing sodium carbonate (160 mg) and sodium bisulfite (120 mg). The aqueous phase was then extracted with methylene chloride (40 mL) (3×) and the organic phases were combined. The organic phase was washed with water (50 mL) and brine (50 mL). It was dried over sodium sulfate and evaporated. The crude compound was purified by flash silica gel chromatography using 15% acetone/methylene chloride to elute the title compound. 400 MHz $^1$H NMR (CDCl$_3$): δ 0.92 (s, 3H); 0.96 (s, 3H); 1.02 (d, 3H); 3.34 (dd, 1H); 4.72 (q, 1H); 5.31 (s, 1H); 5.80 (d, 1H); 6.80 (d, 1H); 6.82 (d, 2H); 6.89 (t, 1H); 7.24 (t, 2H).

EXAMPLE 60

3-oxo-4-aza-7β-methyl-16β-(4-chlorophenoxy)-5β-androst-1-ene

This compound was prepared in a similar fashion as Example 59, but substituting 3-oxo-4-aza-7β-methyl-16β-(4-chlorophenoxy)-5α-androstane in place of 3-oxo-4-aza-7β-methyl-16β-phenoxy-5α-androstane. 400 MHz $^1$H NMR (CDCl$_3$): δ 0.92 (s, 3H); 0.95 (s, 3H); 1.02 (d, 2H); 3.34 (dd, 1H); 4.67 (q, 1H); 5.27 (s, 1H); 5.80 (d, 1H); 6.73 (d, 2H); 6.78 (d, 1H); 7.18 (d, 2H).

EXAMPLE 61

3-oxo-4-aza-4,7β-dimethyl-16β-phenoxy-5α-androstane

To a solution of 3-oxo-4-aza-7β-methyl-16β-phenoxy-5α-androstane (60 mg, 0.16 mmol) in N,N-dimethylformamide (1 mL) was added sodium hydride (8 mg, 0.21 mmol), a 60% dispersion in mineral oil. After stirring for 30 min at room temperature under a nitrogen atmosphere, methyl iodide (40 mg, 0.28 mmol) was added. The reaction was stirred overnight. It was diluted with ethylacetate (50 mL) and washed with 1N hydrochloric acid (50 mL), water (50 mL) and brine (50 mL). The organic phase was dried over sodium sulfate and evaporated. The crude product was purified by flash silica gel chromatography using 10% acetone/methylene chloride to elute the title compound. 400 MHz $^1$H NMR (CDCl$_3$): δ 0.85 (s, 3H); 0.95 (s, 3H); 1.05 (d, 3H); 2.91 (s, 3H); 3.02 (dd, 1H); 4.72 (q, 1H); 6.81 (d, 2H); 6.89 (t, 1H); 7.24 (t, 2H).

EXAMPLE 62

3-oxo-4-aza-4,7β-dimethyl-16β-(4-chlorophenoxy)-5α-androst-1-ene

This compound was prepared in a similar fashion as Example 61, but substituting 3-oxo-4-aza-7β-methyl-16β-(4-chlorophenoxy)-5α-androstan-1-ene in place of 3-oxo-4-aza-7β-methyl-16β-phenoxy-5α-androstane. 400 MHz $^1$H NMR (CDCl$_3$): δ 0.87 (s, 3H); 0.95 (s, 3H); 1.07 (d, 2H); 2.93 (s, 1H); 3.34 (dd, 1H); 4.68 (q, 1H); 5.84 (d, 1H); 6.69 (d, 1H); 6.73 (d, 2H); 7.18 (d, 2H).

EXAMPLE 63

3-oxo-4-aza-4-(2,4-dimethoxybenzyl)-7β-methyl-16β-(3-chloro-4-methylphenoxy)-5α-androstane This compound was prepared in a similar fashion as Example 56, but substituting 2-chloro-4-fluorotoluene in place of 1-chloro-4-fluorobenzene. No purification was done prior to the next reaction.

EXAMPLE 64

3-oxo-4-aza-7β-methyl-16β-(3-chloro-4-methylphenoxy)-5α-androstane

This compound was prepared in a similar fashion as Example 57, but substituting 3-oxo-4-aza-4-(2,4-dimethoxybenzyl)-7β-methyl-16β-(3-chloro-4-methylphenoxy)-5α-androstane in place of 3-oxo-4-aza-4-(2,4-dimethoxy benzyl)-7β-methyl-16β-(4-chlorophenoxy)-5α-androstane. 400 MHz $^1$H NMR (CDCl$_3$): δ 0.86 (s, 3H); 0.93 (s, 3H); 1.01 (d, 3H); 2.26 (s, 3H); 3.08 (dd, 1H); 4.66 (q, 1H); 5.59 (s, 1H); 6.62 (m, 1H); 6.81 (d, 1H); 7.06 (d, 1H).

EXAMPLE 65

3-oxo-4-aza-7β-methyl-16β-(4-methylphenoxy)-5α-androstane

This compound was prepared in a similar fashion as Example 58, but substituting 3-oxo-4-aza-7β-methyl-16β-(3-chloro-4-methyl-phenoxy)-5α-androstane in place of 3-oxo-4-aza-7β-methyl-16β-(4-chloro-phenoxy)-5α-androstane. 400 MHz $^1$H NMR (CDCl$_3$): δ 0.86 (s, 3H); 0.94 (s, 3H); 1.03 (d, 3H); 2.25 (s, 3H); 4.69 (q, 1H); 6.71 (d, 2H); 7.03 (d, 2H).

EXAMPLE 66

3-oxo-4-aza-7β-methyl-16β-(4-methylphenoxy)-5α-androst-1-ene

This compound was prepared in a similar fashion as Example 59, but substituting 3-oxo-4-aza-7β-methyl-16β-

(4-methylphenoxy)-5α-androstane in place of 3-oxo-4-aza-7β-methyl-16β-phenoxy-5α-androstane. 400 MHz $^1$H NMR (CDCl$_3$): δ 0.92 (s, 3H); 0.96 (s, 3H); 1.03 (d, 3H); 2.25 (s, 3H); 3.34 (dd, 1H); 4.68 (q, 1H); 5.35 (s, 1H); 5.81 (d, 1H); 6.71 (d, 2H); 6.79 (d, 1H); 7.03 (d, 2H).

EXAMPLE 67

3-oxo-4-aza-7β-methyl-16β-(4-methylphenoxy)-5α-androstane

This compound was prepared in a similar fashion as Example 61, but substituting 3-oxo-4-aza-7β-methyl-16β-(4-methylphenoxy)-5α-androstane in place of 3-oxo-4-aza-7β-methyl-16β-phenoxy-5α-androstane. 400 MHz $^1$H NMR (CDCl$_3$): δ 0.85 (s, 3H); 0.94 (s, 3H); 1.04 (d, 3H); 2.25 (s, 3H); 2.91 (s, 3H); 3.05 (dd, 1H); 4.69 (q, 1H); 6.71 (d, 2H); 7.04 (d, 2H).

EXAMPLE 68

3-Oxo-4-aza-4,7β-dimethyl-16β-fluoro-5α-androstane

This compound was prepared by treatment of intermediate (12) (Scheme 5) with diethylaminosulfur trifluoride in methylene chloride at room temperature followed by chromatography on silica gel; 64% yield; m/z 321 (M); 400 MHz $^1$H NMR spectrum (CDCl$_3$): 0.87 (s, 3H); 0.92 (s, 3H); 1.04 (d, 3H); 2.90 (s, 3H), 5.12 (m, H).

EXAMPLE 69

3-Oxo-4-aza-4,7β-dimethyl-16β-cyano-5α-androstane

This compound is obtained by conversion of intermediate (25) (Scheme 7) to its methansulfonate derivative by treatment with methanesulfonyl chloride or methanesulfonic anhydride in methylene chloride in the presence of an organic base, such as pyridine and triethylamine, and 4-dimethylaminopyridine (DMAP). Displacement of the methanesulfonate group is effected by heating in an appropriate solvent, such as N,N-dimethylformamide or dimethylsulfoxide, in the presence of sodium or potassium cyanide.

EXAMPLE 70

3-Oxo-4-aza-4-methyl-16β-(1-hexyl)-5α-androstane

Step 1:

3-Oxo-4-aza-4-methyl-16β-(1-hexyl)-5α-androstane

To a 50-mL round-bottom flask under nitrogen was added 1-hexyl-triphenylphosphonium bromide (141 mg, 0.33 mmol) followed by freshly distilled tetrahydrofuran (1 mL). The mixture was cooled to 0° C., and bulyllithium (2.5M solution in hexanes, 132 mL, 0.33 mmol) affording a bright orange solution. The solution was stirred at 0° C. for 10 min., and was charged with a solution of 4-aza-4-methyl-5α-androstan-3,16-dione (50 mg, 0.165 mmol) in tetrahydrofuran (0.5 mL). The reaction mixture was allowed to reach room temperature and stirred overnight. The mixture was then partitioned between water (10 mL) and ethyl acetate (20 mL), the organic layer separated, washed with 0.5N hydrochloric acid (2×10 mL), saturated brine solution, dried (Na$_2$SO$_4$), and evaporated. The title compound was purified by flash silica gel chromatography using 1% methanol/methylene chloride as eluant. This material (29.6 mg) was used without further purification in Step 2.

Step 1:

3-Oxo-4-aza-4-methyl-16β-(1-hexyl)-5α-androstane

A solution of the product obtained in Step 1 (22 mg) in ethyl acetate (0.5 mL) was hydrogenated in the presence of platinum oxide (5 mg) under a balloon atmosphere of hydrogen gas for 1 hour at room temperature. The catalyst was removed by filtration through a Millex-HV disposable filter, and the filtrate was evaporated. The title compound was purified by flash silica gel chromatography using 20% acetone/hexane as eluant; yield 5.2 mg. Mass spectrum: m/z 374 (M+1).

400 MHz $^1$H NMR (CDCl$_3$): δ 2.42 (dd, 2H), 2.90 (s, 3H), and 3.00 (dd, 1H).

EXAMPLE 71

4-aza-4,7β-dimethyl-16b-(4-chlorobenzylidene)-5α-androstan-3-one

Following Reaction Scheme 14, solution of 4-aza-4,7β-dimethyl-5α-androstan-3,17-dione (11) (32 mg, 0.1 mmol), sodium hydride (5 mg, 1.02 eq), diethyl 4-chlorobenzylphosphonate (27 mg, 1.02 eq) and DMF (0.5 mL) were heated to 80° C. for 1 hour. The reaction was cooled, diluted with dichloromethane and washed with water (×2), brine, dried over anhydrous magnesium sulfate, filtered and concentrated. The desired product was purified by silica gel chromatography (hexanes:isopropanol 4:1) 1.5:1 mixture of E/Z isomers: m/z=389

$^1$H NMR(500 MHz, CDCl$_3$): 0.75 (s, 3H); 0.82 (s, 3H); 0.90 (d, 3H); 2.96 (s, 3H); 3.08 (dd, 1H); 6.34 (s, 0.4H); 6.41 (s, 0.6H); 7.18–7.38 (m, 5H).

EXAMPLE 72

4-aza-4,7β-dimethyl-16-benzylidene-5α-androstan-3-one

This example was prepared in a similar fashion as 4-aza-4,7β-dimethyl-16-(4-chlorobenzylidene)-5α-androstan-3-one (71) but substituting diethyl benzylphosphonate for diethyl 4-chlorobenzylphosphonate: m/z=390

$^1$H NMR(500 MHz, CDCl$_3$): 0.75 (s, 3H); 0.88 (s, 3H); 1.05 (d, 3H); 2.94 (s, 3H); 3.08 (dd, 1H); 6.28 (s; 0.4H); 6.35 (s, 0.6H); 7.15–7.35(m, 5H).

EXAMPLE 73

4-aza-4,7β-dimethyl-16-(4-methylbenzylidene)-5α-androstan-3-one

This example was prepared in a similar fashion as 4-aza-4,7β-dimethyl-16-(4-chlorobenzylidene)-5α-androstan-3-one (71) but substituting diethyl 4-methylphosphonate for diethyl 4-chlorobenzylphosphonate: m/z=404

$^1$H NMR (500 MHz, CDCl$_3$): 0.78 (s, 3H); 0.85 (s, 3H); 1.1 (d, 3H); 2.32 (s, 3H); 2.94 (s, 3H); 3.08 (dd, 1H); 6.30 (s, 0.4H); 6.38 (s, 0.6H); 7.10–7.24 (m, 5H).

EXAMPLE 74

4-aza-4,7β-dimethyl-16-(4-chlorobenzyl)-5α-androstan-3-one

To a solution of 4-aza-4,7β-dimethyl-16-(4-chlorobenzylidene)-5α-androstan-3-one (71) (33 mg) in ethanol (4 mL) was added 5% Rh/C and the black suspension stirred under a hydrogen balloon. After 2 hours the mixture was filtered to remove catalyst, concentrated and purified on silica gel (hexanes:acetone 3:1) to give the desired product as a 3:1 mixture of isomers: m/z 427

$^1$H NMR (500 MHz, CDCl$_3$): 0.84 (s,3H); 0.86 (s,3H); 1.02 (d, 3H); 2.92 (bs, 2.7H); 2.93 (bs, 1.3H); 2.98 (s, 3H); 3.02 (dd, 1H); 7.10 (d, 2H), 7.25 (d, 2H).

EXAMPLE 75

4-aza-4,7β-dimethyl-16-(4-methylbenzyl)-5α-androstan-3-one

This example was prepared similarly to the procedure used for 4-aza-4,7β-dimethyl-16-(4-chlorobenzyl)-5α-androstan-3-one (74): m/z=408

$^1$H NMR (500 MHz, CDCl$_3$): 0.86(s, 6H); 1.04 (d, 3H); 2.33 (s, 3H); 2.95 (s, 2H); 2.96 (s, 1H); 3.05 (dd, 1H); 7.06–7.11 (m, 4H).

EXAMPLE 76

4-aza-4,7β-dimethyl-16-(3-pyridylmethyl)-5α-androstan-3-one

This example was prepared similarly to the procedure used for 4-aza-4,7β-dimethyl-16-(4-chlorobenzyl)-5α-androstan-3-one (74) except 3-pyridylmethyl-dimethylphosphonate was used: m/z=395

$^1$H NMR (500 MHz, CDCl$_3$): 0.89 (s, 3H); 0.88 (s, 3H); 1.03(d, 3H); 2.93 (bs, 2H); 2.94 (bs, 1H); 2.98 (s, 3H); 3.04 (dd, 1H); 7.10 (d, 2H), 7.25 (d, 2H); 7.58 (s, 1H); 8.55 (s, 2H).

EXAMPLE 77

4-aza-4,7β-dimethyl-16α-methanesulfonyl5α-androstan-3-one

Following Reaction Scheme 13, to a solution of 4-aza-4,7β-dimethyl-16α-hydroxy-5α-androstan-3-one (25) (65 mg, 0.2 mmol) in anhydrous dichloromethane was added a catalytic amount of DMAP followed with methanesulfonic anhydride (45 mg, 1.1 eq). After 15 min, the motion was diluted with dichloromethane, washed with 1M HCl (×3), 1M sodium bicarbonate, water and brine, dried over anhydrous magnesium sulfate filtered and concentrated to yield the desired compound of sufficent purity: m/z=398

$^1$H NMR (500 MHz, CDCl$_3$): 0.78 (s, 3H); 0.85 (s, 3H); 1.02 (d, 3H); 2.95 (s, 3H); 3.1 (dd, 2H); 5.18 (m, 1H).

EXAMPLE 78

4-aza-4,7β-dimethyl-16β-thiophenoxy-5α-androstan-3-one

To a solution of thiophenol (50 μL, 2.5 eq) in anhydrous THF was added sodium hydride (20 mg, 2.6 eq). After stirring 20 min, a THF solution of 4-aza-4,7β-dimethyl-16α-methanesulfonyl-5α-androstan-3-one (77) (65 mg. 0.2 mmol) was added and the mixture stirred 20 hours at ambient temperature. The reaction was quenched with 1M ammonium chloride and diluted with ethyl acetate, washed with water and brine, dried over anhydrous magnesium sulfate filtered and concentrated. The desired compound was purified by silica gel chromatography (hexanes:isopropanol 9:1): m/z=412

$^1$H NMR (500 MHz, CDCl$_3$): 0.86 (s, 3H); 0.96 (s, 3H); 1.06 (d, 3H); 2.94 (s, 3H); 3.06 (dd, 2H); 3.65 (m, 1H); 7.26–7.70 (m, 5H).

EXAMPLE 79

4-aza-4,7β-dimethyl-16β-(4-chlorothiophenoxy)-5α-androstan-3-one

This compound was prepared in a similar fashion as 4-aza-4,7β-dimethyl-16β-thiophenoxy-5α-androstan-3-one (78) but substituting 4-chlorothiophenol in place of thiophenol: m/z=446

$^1$H NMR (500 MHz, CDCl$_3$): 0.85 (s,3H); 0.96 (s, 3H); 1.04 (d, 3H); 2.94 (s, 3H); 3.02 (dd, 2H); 3.61 (m, 1H); 7.22 (d, 2H); 7.32 (d, 2H).

EXAMPLE 80

4-aza-4,7β-dimethyl-16β-(4-fluorothiophenoxy)-5α-androstan-3-one

This compound was prepared in a similar fashion as 4-aza-4,7β-dimethyl-16β-thiophenoxy-5α-androstan-3-one (78) but substituting 4-fluorothiophenol in place of thiophenol: m/z=431

$^1$H NMR (500 MHz, CDCl$_3$): 0.85 (s, 3H); 0.96 (s, 3H); 1.05 (d, 3H); 2.92 (s, 3H); 3.03 (dd, 2H); 3.51 (m, 1H); 6.99 (d, 2H); 7.35 (d, 2H).

EXAMPLE 81

4-aza-4,7β-dimethyl-16β-(4-methylthiophenoxy)-5α-androstan-3-one

This compound was prepared in a similar fashion as 4-aza-4,7β-dimethyl-16β-thiophenoxy-5α-androstan-3-one (78) but substituting 4-methylthiophenol in place of thiophenol: m/z=426

$^1$H NMR(500 MHz, CDCl$_3$): 0.75 (s, 3H); 0.95 (s, 3H); 1.1 (d, 3H); 2.31 (s, 3H); 2.94 (s, 3H); 3.02 (dd, 2H); 3.59 (m, 1H); 7.09 (d, 2H); 7.22 (d, 2H).

EXAMPLE 82

4-aza-4,7β-dimethyl-16β-(4-methoxythiophenoxy)-5α-androstan-3-one

This compound was prepared in a similar fashion as 4-aza-4,7β-dimethyl-16β-thiophenoxy-5α-androstan-3-one (78) but substituting 4-methoxythiophenol in place of thiophenol: m/z=443

$^1$H NMR (500 MHz, CDCl$_3$): 0.81 (s,3H); 0.93 (s,3H); 1.18 (d,3H); 2.93 (s,3H); 3.02 (dd,2H); 3.50 (m,1H); 3.81 (s,3H); 7.45 (d,2H); 7.67 (d,2H).

EXAMPLE 83

4-aza-4,7β-dimethyl-16β-phenylsulfinyl-5α-androstan-3-one

To a solution of 4-aza-4,7β-dimethyl-16β-thiophenoxy-5α-androstan-3-one (78) (20 mg, 0.05 mmol) in dicloromethane at 0° C. was added mCPBA (11 mg, 1 eq) and the solution stirred 1 hour. The reaction was diluted with dichloromethane and washed with 1M sodium bicarbonate, water, brine and dried over anhydrous sodium sulfate. The desired compound was purified by silica gel chromatography to yield a 4.6:1 mixture of diastereomers: m/z=428

$^1$H NMR(500 MHz, CDCl$_3$): 0.83 (s, 3H); 0.92 (s, 3H); 1.01 (d, 3H); 2.92 (s, 3H); 3.01 (dd, 2H); 3.19 (m, 0.85H); 3.55 (m, 0.15H); 7.5–7.70 (m, 5H).

EXAMPLE 84

4-aza-4,7β-dimethyl-16β-phenylsulfonyl-5α-androstan-3-one

A solution of 4-aza-4,7β-dimethyl-16β-phenylsulfinyl-5α-androstan-3-one (83) 912 mg, 0.03 mmol) in dichloromethane was treated with mCPBA (9 mg, 1.5 eq) for 3 hours. The reaction was diluted with dichloromethane and washed with 1M sodium bicarbonate, water, brine and dried over anhydrous sodium sulfate. The desired compound was purified by silica gel chromatography (hexanes:isopropanol 7:3): m/z=444

$^1$H NMR (500 MHz, CDCl$_3$): 0.85 (s, 3H); 0.91 (s, 3H); 1.0 (d, 3H); 2.95 (s, 3H); 3.05 (dd, 2H); 3.55 (m, 0.15H); 7.41 (t, 1H); 7.55 (t, 2H); 7.90 (d, 1H), 7.90 (d, 1H).

EXAMPLE 85

3-Oxo-4-aza-4,16β-dimethyl-5α-androstane

This compound is made by converting the readily available 4-aza-4,16β-dimethyl-androstan-3,17-dione to the 17-triflate. Reduction of the triflate through conventional methods yields the titled 16βmethyl analog.

Mass spectrum: m/z 304 (M+1)

400 MHz NMR (CDCl$_3$): δ 0.76 (s, 3H); 0.85 (s, 3H); 1.04 (d, 3H); 2.90 (s, 3H); 3.01 (dd, 1H).

BIOLOGICAL ASSAYS

Preparation of Human prostatic and scalp 5α-reductases

Samples of human tissue were pulverized using a freezer mill and homogenized in 40 mM potassium phosphate, pH 6.5, 5 mM magnesium sulfate, 25 mM potassium chloride, 1 mM phenylmethylsulfonyl fluoride, 1 mM dithiothreitol (DTT) containing 0.25M sucrose using a Potter-Elvehjem homogenizer. A crude nuclear pellet was prepared by centrifugation of the homogenate at 1,500×g for 15 min. The crude nuclear pellet was washed two times and resuspended in two volumes of buffer. Glycerol was added to the resuspended pellet to a final concentration of 20%. The enzyme suspension was frozen in aliquots at −80° C. The prostatic and scalp reductases were stable for at least 4 months when stored under these conditions.

Cloned enzyme protocol:

For IC$_{50}$ determinations, the test 5α-reductase 1 and 2 inhibitors were dissolved in ethanol and serially diluted to the appropriate concentration. The baculovirus-expressed recombinant type 1 5α-reductase was preincubated with inhibitor (0.1–1,000 nM) in 40 mM sodium phosphate, pH 7.0, 500 µM NADPH, 1 mM DTT and 1 mg/ml BSA for 18 h at 4° C. The reaction was initiated by the addition of [7-$^3$H]T (NEN, 20 Ci/mmol) and NADPH to a final concentration of 0.3 µM and NADPH and incubated at 37° C. for 90 min. Similarly, baculovirus-expressed type 2 5α-reductase was preincubated with inhibitor (1–10,000 nM) in 40 mM sodium citrate, pH 5.5, 500 µM NADPH, 1 mM DTT and 1 mg/ml BSA for 18 h at 4° C. The reaction was initiated by the addition of [7-$^3$H]T (NEN, 20 Ci/mmol) and NADPH to a final concentration of 0.3 µM and 500 µM, respectively. The conversion of T to DHT was monitored using a radioflow detector following separation by reverse phase HPLC (Whatman RACII C18 column, 1 ml/min 0.1% TFA in water:methanol (42:58); retention times T, 6.3 min, DHT, 9.7 min).

5α-reductase assay

The reaction mixture for the type 1 5α-reductase contained 40 mM potassium phosphate, pH 6.5, 5 µM [7-$^3$H]-testosterone, 1 mM dithiothreitol and 500 µM NADPH in a final volume of 100 µl. The reaction mixture for the type 2 5α-reductase contained 40 mM sodium citrate, pH 5.5, 0.3 µM [7-$^3$H]-testosterone, 1 mM dithiothreitol and 500 µM NADPH in a final volume of 100 µl. Typically, the assay was initiated by the addition of 50–100 µg prostatic homogenate or 75–200 µg scalp homogenate and incubated at 37° C. After 10–50 min the reaction was quenched by extraction with 250 µl of a mixture of 70% cyclohexane: 30% ethyl acetate containing 10 µg each DHT and T. The aqueous and organic layers were separated by centrifugation at 14,000 rpm in an Eppendorf microfuge. The organic layer was subjected to normal phase HPLC (10 cm Whatman partisil 5 silica column equilibrated in 1 ml/min 70% cyclohexane: 30% ethyl acetate; retention times: DHT, 6.8–7.2 min; androstanediol, 7.6–8.0 min; T, 9.1–9.7 min). The HPLC system consisted of a Waters Model 680 Gradient System equipped with a Hitachi Model 655A autosampler, Applied Biosystems Model 757 variable UV detector, and a Radiomatic Model A120 radioactivity analyzer. The conversion of T to DHT was monitored using the radioactivity flow detector by mixing the HPLC effluent with one volume of Flo Scint 1 (Radiomatic). Under the conditions described, the production of DHT was linear for at least 25 min. The only steroids observed with the human prostate and scalp preparations were T, DHT and androstanediol.

Inhibition studies

Compounds were dissolved in 100% ethanol. IC$_{50}$ values represent the concentration of inhibitor required to decrease enzyme activity to 50% of the control. IC$_{50}$ values were determined using a 6 point titration where the concentration of the inhibitor was varied from 0.1 to 1000 nM.

Representative compounds of this invention were tested in the above described assay for 5α-reductase type 1 and type 2 inhibition. For the inhibition of 5α-reductase type 1, the compounds have IC$_{50}$ values lower than 600 nM, with the majority of compounds having IC$_{50}$ values ranging from about 0.3 nM to about 200 nM. For the inhibition of 5α-reductase type 2, the same compounds have IC$_{50}$ values greater than about 155 nM, with the majority of compounds having IC$_{50}$ values greater than 1000 nM. Each compound tested has at least a 2-fold greater selectivity for inhibition of 5α-reductase type 1 over type 2, with the majority of the compounds having a 10-fold or greater selectivity for inhibition of 5α-reductase type 1 over type 2. These results demonstrate the utility of the compounds of the instant invention for the treatment of androgenetic conditions.

A compound referred to herein as a 5α-reductase 2 inhibitor is a compound that shows inhibition of the 5α-reductase 2 isozyme in the above-described assay; likewise, a compound referrred to herein as a 5α-reductase 1 inhibitor is a compound that shows inhibition of the 5α-reductase 1 isozyme in the above-described assay.

Human Dermal Papilla Cell Assay

The dermal papilla is a small group of cells at the base of each hair follicle, and it is presently thought that these cells are stem cells that form the basis for hair growth. These cells have been shown to have 5 alpha reductase activity, and it is therefore possible to test inhibitors of 5 alpha reductase in these cell culture systems.

Isolated and cultured dermal papilla cells are prepared according to the methods of Messenger, A. G., *The Culture of Dermal Papilla Cells From Human Hair Follicles*, Br. J. Dermatol. 110:685–689, 1984 and Itami, S. et al., *5α-Reductase Activity In Cultured Human Dermal Papilla Cells From Beard Compared With Reticular Dermal Fibroblasts*, J. Invest. Dermatol. 94:150–152, 1990. Beard dermal papilla cells and occipital scalp hair of two different individuals are used throughout the study. All experiments are performed at confluency after the fourth to sixth subculture. Confluent monolayers are rinsed twice with phosphate-buffered saline, scraped from dishes by rubber policemen, and collected into a centrifuge tube. The cell suspensions are centrifuged at 1,500 rpm for 10 min at 4° C. The pellets are resuspended in 20 mM Tris-HCl buffer, pH 7.5, at 4° C., containing 250 mM sucrose, 1 mM $MgCl_2$, and 2 mM $CaCl_2$, by vortexing and 10 passes through a 25-gauge needle. The crude homogenate is further homogenized by a teflon-glass homogenizer, and is used as the cell homogenate. For the study of subcellular localization of 5α-reductase, the cell homogenate is centrifuged at 800×g for 10 min to yield a crude nuclear pellet. The resultant supernatant is centrifuged at 10,000×g for 15 min to produce a crude mitochondrial pellet. The supernatant is centrifuged at 100,000×g for 60 min to yield a miccrosomal pellet and cytosol. Each particulate fraction is washed twice and resuspended in the buffer.

A standard incubation mixture will consist of 50 nM [$^3$H]-testosterone, 1 mM NADPH, 100 mM sodium citrate, pH 5.5 or 100 mM Tris-HCl, pH 7.5, and 50 μl of the cell homogenate, in a final volume of 100 μl. Each tube contains 50–100 μg of cellular protein. Incubation is carried out at 37° C. for 30 min. During this incubation, the reaction is proportional to the time. For the study of optimum pH, citrate buffer is used at pH 4.5–6.5, and the Tris HCl buffer at pH 7.0–9.0. The protein content is determined by the method of Lowry, et al., *Protein Measurement With The Folin Phenol Reagent* J. Biol. Chem. 193:265–275, 1951.

After incubation, the reaction is stopped by adding 4 times volume of chloroform-methanol (2/1:V/V) containing 110 μg each of carrier steroids. The extracted steroids are analyzed by thin-layer chromatography as previously described by Gomez, et al., *In Vitro Metabolism Of Testosterone-4-$^{14}$C and Δ-androstene-3, 17-dione-4-$^{14}$C In Human Skin.* Biochem. 7:24–32, 1968, and the purity of each steroid is determined by the recrystallization method. The activity of 5α-reductase is expressed by the sum of dihydrotestosterone, androstanediol and androstanedione formed. [1,2-$^3$H]-testosterone (55.2 Ci/mmol) is obtainable from New England Nuclear Corporation (Boston, Mass.) and unlabeled steroids can be purchased from Sigma Chemical Company (St. Louis, Mo.). Fetal calf serum is obtainable from Hazleton (Lenaxa, Kans.). All other chemicals are of reagent grade.

Fuzzy Rat Acne Model

Adult fuzzy rats are a variety of rat that has stunted hair growth, brown colored seborrhea covering their entire back skin and abnormally increased serum production after puberty that has been demonstrated to be due to circulating androgens. 0.1, 0.05 and 0.025% solutions of a selected 5α-reductase inhibitor of interest are prepared in a vehicle of propylene glycol, isopropanol, isopropyl myristate and water (50/30/2/18%), and is topically applied onto the backs of adult male fuzzy rats, 0.2 ml per animal daily for 4 weeks. Controls receive the vehicle alone and 5 of them are castrated. After 2 weeks seborrhea will be dose-dependently depleted and after 4 weeks bromodeoxyuridine (BrdU, 200 mg/kg) is intraperitoneally injected 2 hours before sacrifice. The skin tissues are incubated with EDTA (20 mM) in phosphate buffer, 1.5 hours at 37° C. The pilo-sebaceous unit attached to the epidermis is striped from the dermis and fixed with formalin for immuno-staining of BrdU. DNA synthesis cells showing a BrdU-positive nucleus are located in the outer glandular border. The number of S-phase cells per lobe is determined with a micro-image apparatus. Using formalin feed skin, frozen serial sections are stained with 1% osmium and the size of the lobes is measured. A positive inhibitor of skin 5α-reductrase will induce suppression of serum production by inhibiting the rate of glandular cell turnover, and showing reduced lobular size.

The following describes an example methodology that can be used for detection of hair growth.

MACROPHOTOGRAPHY AND GLOBAL PHOTOGRAPHY PROCEDURE FOR DETECTION OF HAIR GROWTH

A. Macrophotographic Procedure
Location:
  ID card
  Haircount target area
Equipment:
  Film: Kodak-T-max 24 exposure each of same emulsion lot number
  Camera:
  Nikon N-6000
  Lens: Nikkor 60 mm f2.8
  Flashes: Nikon SB-21B Macroflash
  Device: registration device
Photographic Procedure:

In these clinical photographs, the only variable allowed is the haircount. Film emulsion, lighting, framing, exposure, and reproduction ratios are held constant.

1. The haircount area on the patient is prepared as follows: A small (~1 mm) dot tattoo is placed at the beginning of the study at the leading edge of the bald area directly interior to the center of the vertex bald spot, using a commercial tattooing machine or manually (needle and ink). An area approximately one square inch in size, centered at the tattoo at the leading edge of the balding area, is clipped short (~2 mm). Cut hairs are removed from the area to be photographed, using tape. Compressed air and/or ethanol wipes may also be used to facilitate removal of cut hairs.

2. Magnification: Each lens supplied has a fixed reproduction ratio of 1:1.2.
  Aperture: Every photograph is taken at f/22.
  Film: T-Max 100 (24 exposure) is used.

3. Patient's haircount target area. Three exposures (−⅔, 0, and +⅔ f-stop).

A trained technician places a transparency over the photograph and, using a felt tip pen, places a black dot over each visible hair. The dot map transparency is then counted using image analysis with computer assistance.

Photographs are coded with a random number corresponding to study site, visit number and patient allocation number to insure blinding to time. At Month 6, baseline and Month 6 photographs are counted and data analyzed for interim analysis. At Month 12, baseline, Month 6 and Month 12 photographs are counted and data analyzed for the primary endpoint.

Methodology for detection of hair growth is also described in Olsen, E. A. and Delong, E., *J. American Academy of Dermatology*, Vol. 23, p. 470 (1990).

B. Global Photographic Procedure
Locations:
  Color card/patient Id
  Global photograph
Equipment:
  Film: Kodachrome KR-64 24 exposure each of same emulsion lot number
  Camera: Nikon N-6000
  Lens: Nikkor 60 mm f2.8
  Flashes: Nikon SB-23
  Color card/patient Id Photographic Procedure In these clinical photographs, the only variable allowed is the global area's appearance. Anything extraneous to the area (clothing, furniture, walls, etc.) is eliminated from the fields to be photographed.

1. Patients will have global photographs taken prior to hair clipping with the head in a fixed position (determined by the supplied stereotactic device). Hair on the patient's head is positioned consistently so as to not obscure the bald area.

2. Magnification: Each lens supplied has a fixed reproduction ratio of 1:6.
   Aperture: Every photograph will be taken at f/11.
   Film: Kodachrome (24 exposure) is used.

3. Patient's global photographs. Three exposures at zero compensation.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the Formula I

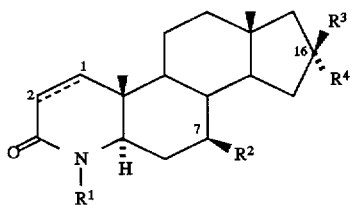

or a pharmaceutically acceptable salt thereof wherein:
the C1–C2 carbon-carbon bond may be a single bond, or a double bond as indicated by the dashed line;
$R^1$ is selected from the group consisting of hydrogen and $C_{1-10}$ alkyl;
$R^2$ is selected from the group consisting of hydrogen and $C_{1-10}$ alkyl;
one of $R^3$ and $R^4$ is selected from the group consisting of hydrogen and methyl, and the other is selected from the group consisting of:
  (a) amino;
  (b) cyano;
  (c) fluoro,
  (d) methyl;
  (e) OH;
  (f) —C(O)NR$_b$R$_c$, where R$_b$ and R$_c$ are independently H, $C_{1-6}$ alkyl, aryl, or aryl$C_{1-6}$alkyl; wherein the alkyl moiety is unsubstituted or substituted with 1–3 of: halo; $C_{1-4}$alkoxy; or trifluoromethyl; and the aryl moiety is unsubstituted or substituted with 1–3 of: halo; $C_{1-4}$alkyl; $C_{1-4}$ alkoxy; or trifluoromethyl;
  (g) $C_{1-10}$ alkyl-X—;
  (h) $C_{2-10}$ alkenyl-X—;
wherein the $C_{1-10}$ alkyl in (g) and $C_{2-10}$ alkenyl in (h) is unsubstituted or substituted with one to three of:
  i) halo; hydroxy; cyano; nitro; mono-, di- or trihalomethyl; oxo; hydroxysulfonyl; carboxy;
  ii) hydroxy$C_{1-6}$alkyl; $C_{1-6}$alkyloxy; $C_{1-6}$ alkylthio; $C_{1-6}$alkylsulfonyl; $C_{1-6}$ alkyloxycarbonyl; in which the $C_{1-6}$ alkyl moiety is unsubstituted or further substituted with 1–3 of: halo; $C_{1-4}$ alkoxy; or trifluoromethyl;
  iii) arylthio; aryl; aryloxy; arylsulfonyl; aryloxycarbonyl; in which the aryl moiety, is unsubstituted or can be further substituted with 1–3 of: halo; $C_{1-4}$ alkyl; $C_{1-4}$ alkoxy; or trifluoromethyl;
  iv) —C(O)NR$_b$R$_c$; —N(R$_b$)—C(O)—R$_c$; —NR$_b$R$_c$; where R$_b$ and R$_c$ are defined above;
  (i) aryl-X—;
  (j) heteroaryl-X—;
wherein the aryl in (i) and heteroaryl in (j) are unsubstituted or substituted with one to three of:
  v) halo; hydroxy; cyano; nitro; mono-, di- or trihalomethyl; mono-, di- or trihalomethoxy; $C_{2-6}$ alkenyl; $C_{3-6}$ cycloalkyl; formyl; hydrosulfonyl; carboxy; ureido;
  vi) $C_{1-6}$ alkyl; hydroxy $C_{1-6}$ alkyl; $C_{1-6}$ alkyloxy; $C_{1-6}$ alkyloxy $C_{1-6}$alkyl; $C_{1-6}$ alkylcarbonyl; $C_{1-6}$ alkylsulfonyl; $C_{1-6}$ alkylthio; $C_{1-6}$ alkylsulfinyl; $C_{1-6}$ alkylsulfonamido; $C_{1-6}$ alkylarylsulfonamido; $C_{1-6}$ alkyloxy-carbonyl; $C_{1-6}$ alkyloxycarbonyl $C_{1-6}$alkyl; R$_b$R$_c$N—C(O)—$C_{1-6}$alkyl; $C_{1-6}$ alkanoylamino $C_{1-6}$ alkyl; aroylamino $C_{1-6}$ alkyl; wherein the $C_{1-6}$ alkyl moiety is unsubstituted or substituted with 1–3 of: halo; $C_{1-4}$alkoxy; or trifluoromethyl;
  vii) aryl; aryloxy; arylcarbonyl; arylthio; arylsulfonyl; arylsulfinyl; arylsulfonamido; aryloxycarbonyl; wherein the aryl moiety is unsubstituted or substituted with 1–3 of: halo; $C_{1-4}$alkyl; $C_{1-4}$alkoxy; or trifluoromethyl;
  viii) —C(O)NR$_b$R$_c$; —O—C(O)—NR$_b$R$_c$; —N(R$_b$)—C(O)—R$_c$; —NR$_b$R$_c$; R$_b$—C(O)—N(R$_c$)—; where R$_b$ and R$_c$ are defined in (f) above; and —N(R$_b$)—C(O)—OR$_g$, wherein R$_g$ is $C_{1-6}$alkyl or aryl, in which the alkyl moiety is unsubstituted or substituted with 1–3 of: halo; $C_{1-4}$alkoxy; or trifluoromethyl, and the aryl moiety is unsubstituted or substituted with 1–3 of: halo; $C_{1-4}$alkyl; $C_{1-4}$ alkoxy, or trifluoromethyl; —N(R$_b$)—C(O) NR$_c$R$_d$, wherein R$_d$ is selected from H, $C_{1-6}$ alkyl, and aryl; in which said $C_{1-6}$alkyl and aryl is unsubstituted or substituted as described above in (f) for R$_b$ and R$_c$;
  (k) $R^3$ and $R^4$ taken together are carbonyl oxygen;
  (l) $R^3$ and $R^4$ taken together are =CH—R$_g$, wherein R$_g$ is defined in viii); and wherein:
X is selected from the group consisting of:
  —O—; —S(O)$_n$—; —C(O)—; —CH(R$_e$)—; —C(O)—O—*; —C(O)—N(R$_e$)—*; —N(R$_e$)—C(O)—O—*; —O—C(O)—N(R$_e$)—*; —N(R$_e$)C(O)—N(R$_e$)—; —O—CH(R$_e$)—*; —N(R$_e$)—; wherein R$_e$ is H, $C_{1-3}$ alkyl, aryl, aryl-$C_{1-3}$ alkyl, or unsubstituted or substituted heteroaryl, as defined above in (j);
wherein the asterisk (*) denotes the bond which is attached to the 16-position in Structure I; and n is zero, 1 or 2;

aryl is independently selected at each occurrence from phenyl and naphthyl, and heteroaryl is independently selected from pyridyl, oxazolyl and pyrrolyl.

2. The compound of claim 1 wherein $R^1$ is hydrogen or methyl and $R^2$ is hydrogen or methyl.

3. The compound of claim 1 wherein said heteroaryl is substituted with one to two substituents.

4. The compound of claim 2 wherein:

one of $R^3$ and $R^4$ is selected from the group consisting of hydrogen and methyl, and the other is selected from the group consisting of:

(b) cyano;
(c) fluoro;
(e) OH;
(g) $C_{1-10}$ alkyl-X—, where alkyl is unsubstituted or substituted with aryl, and wherein aryl in turn is unsubstituted or substituted with 1–2 of halo or $C_{1-6}$alkyl;
(h) $C_{2-10}$ alkenyl-X—;
(i) aryl-X—;
(j) heteroaryl-X—;

wherein the aryl in (i) and heteroaryl in (j) are unsubstituted or substituted with one to two of:

x) halo; cyano; nitro; trihalomethyl; trihalomethoxy; $C_{1-6}$ alkyl; aryl; $C_{1-6}$ alkylsulfonyl; $C_{1-6}$ alkyl-arylsulfonamino;

xi) —$NR_bR_c$; $R_b$—C(O)—N($R_c$)—; wherein $R_b$ and $R_c$ are independently H, $C_{1-6}$ alkyl, aryl, or aryl$C_{1-6}$alkyl; wherein the alkyl moiety is unsubstituted or substituted with 1–3 of: halo; $C_{1-4}$alkoxy; or trifluoromethyl; and the aryl moiety is unsubstituted or substituted with 1–3 of: halo; $C_{1-4}$alkyl; $C_{1-4}$ alkoxy; or trifluoromethyl; and wherein:

X is selected from the group consisting of:

—O—; —S(O)$_n$—; —CH($R_e$)—; —C(O)—N($R_e$)—*; —O—C(O)—N($R_e$)—*;

wherein $R_e$ is H, $C_{1-3}$ alkyl, aryl, aryl $C_{1-3}$ alkyl;

wherein the asterisk (*) denotes the bond which is attached to the 16-position in Structure I; and n is zero or 2.

5. The compound of claim 4 wherein the $C_1$-$C_2$ carbon-carbon bond is a single bond, $R^1$ is methyl, $R^2$ is methyl, $R^3$ is selected from unsubstituted or substituted aryloxy, and $R^4$ is hydrogen.

6. The compound 3-oxo-4-aza-4,7β-dimethyl-16β-(4-chlorophenoxy)-5α-androstane, or a pharmaceutically acceptable salt thereof.

7. A method for treating the condition of acne vulgaris consisting essentially of administering to a mammal in need of such treatment a therapeutically effective amount of a compound of claim 1 or a therapeutically effective amount of a compound of claim 1 in combination with an inhibitor of 5α-reductase 2 selected from finasteride, epristeride and turosteride.

8. A method for treating the condition of acne vulgaris consisting essentially of administering to a mammal in need of such treatment a therapeutically effective amount of a compound of claim 1, or a therapeutically effective amount of a compound of claim 1 in combination with an inhibitor of 5α-reductase 2, wherein said compound of claim 1 is 3-oxo-4-aza-4,7β-dimethyl-16β-(4-chlorophenoxy)-5α-androstane, or a pharmaceutically acceptable salt thereof, and the inhibitor of 5α-reductase 2 is selected from finasteride, epristeride and turosteride.

9. A pharmaceutical composition consisting essentially of a pharmaceutically acceptable carrier and a therapeutically effective amount of a compound of claim 1.

10. The pharmaceutical composition of claim 9 further consisting of a therapeutically effective amount of an inhibitor of 5α-reductase 2 selected from finasteride, epristeride and turosteride.

11. A pharmaceutical composition consisting essentially of a pharmaceutically acceptable carrier and a therapeutically effective amount of a compound of claim 1, wherein said compound of claim 1 is 3-oxo-4-aza-4,7β-dimethyl-16β-(4-chlorophenoxy)-5α-androstane, or a pharmaceutically acceptable salt thereof.

12. The pharmaceutical composition of claim 9 wherein the pharmaceutically acceptable carrier is adapted for topical administration.

13. The compound according to claim 1 selected from:

3-oxo-4-aza-7β-methyl-16β-(4-methylphenoxy)-5α-androst-1-ene, and 3-oxo-4-aza-4,7β-dimethyl-16β-phenoxy-5α-androstane.

14. A method for treating the condition of acne vulgaris consisting essentially of administering to a mammal in need of such treatment a therapeutically effective amount of a compound of claim 1, or a therapeutically effective amount of a compound of claim 1 in combination with an inhibitor of 5α-reductase 2, wherein the compound of claim 1 is selected from:

3-oxo-4-aza-7β-methyl-16β-(4-methylphenoxy)-5α-androst-1-ene, and 3-oxo-4-aza-4,7β-dimethyl-16β-phenoxy-5α-androstane
and wherein the inhibitor of 5α-reductase 2 is selected from finasteride, epristeride and turosteride.

15. The method of claim 14 wherein the inhibitor of 5α-reductase 2 is finasteride.

16. A pharmaceutical composition consisting essentially of a pharmaceutically acceptable carrier and a therapeutically effective amount of a compound of claim 1, wherein the compound of claim 1 is selected from 3-oxo-4-aza-7β-methyl-16β-(4-methylphenoxy)-5α-androst-1-ene, and 3-oxo-4-aza-4,7β-dimethyl-16β-phenoxy-5α-androstane
or a pharmaceutically acceptable salt thereof.

17. The compound of claim 1 selected from the group consisting of:

4-aza-4,7β-dimethyl-5α-androstane-3,16-dione;
4-aza-4-methyl-5α-androstan-3,16-dione;
3-oxo-4-aza-4-methyl-16β-hydroxy-5α-androstane;
3-oxo-4-aza-4-methyl-16β-(benzylaminocarbonyloxy)-5α-androstane;
3-oxo-4-aza-4-methyl-16β-benzoylamino-5α-androstane;
3-oxo-4-aza-4-methyl-16β-methoxy-5α-androstane;
3-oxo-4-aza-4-methyl-16β-allyloxy-5α-androstane;
3-oxo-4-aza-4-methyl-16β-(n-propyloxy)-5α-androstane;
3-oxo-4-aza-4-methyl-16α-hydroxy-5α-androstane;
3-oxo-4-aza-4-methyl-16β-(phenoxy)-5α-androstane;
3-oxo-4-aza-7β-methyl-16β-(phenoxy)-5α-androst-1-ene;
3-oxo-4-aza-4-methyl-16α-methoxy-5α-androstane;
3-oxo-4-aza-4-methyl-16β-(4-chlorophenoxy)-5α-androstane;
3-oxo-4-aza-7β-methyl-16β-(4-chlorophenoxy)-5α-androst-1-ene;

3-oxo-4-aza-7β-methyl-16β-(4-chlorophenoxy)-5α-androstane;
3-oxo-4-aza-7β-methyl-16β-(3-chloro-4-methylphenoxy)-5α-androstane;
3-oxo-4-aza-7β-methyl-16β-(4-methylphenoxy)-5α-androstane;
3-oxo-4-aza-7β-methyl-16β-(4-methylphenoxy)-5α-androst-1-ene;
3-oxo-4-aza-7β-methyl-16β-[4-(1-pyrrolyl)phenoxy]-5α-androst-1-ene;
3-oxo-4-aza-4,7β-dimethyl-16β-hydroxy-5α-androstane;
3-oxo-4-aza-4,7β-dimethyl-16β-methoxy-5α-androstane;
3-oxo-4-aza-4,7β-dimethyl-16β-allyloxy-5α-androstane;
3-oxo-4-aza-4,7β-dimethyl-16β-(3,3-dimethylallyloxy)-5α-androstane;
3-oxo-4-aza-4,7β-dimethyl-16β-(n-propyloxy)-5α-androstane;
3-oxo-4-aza-4,7β-dimethyl-16β-(iso-pentoxy)-5α-androstane;
3-oxo-4-aza-4,16α-dimethyl-16β-hydroxy-5α-androstane;
3-oxo-4-aza-4,7β-dimethyl-16β-ethyloxy-5α-androstane;
3-oxo-4-aza-4,7β-dimethyl-16β-benzyloxy-5α-androstane;
3-oxo-4-aza-4,7β-dimethyl-16α-hydroxy-5α-androstane;
3-oxo-4-aza-4,7β-dimethyl-16β-methylthio-5α-androstane;
3-oxo-4-aza-4,7β-dimethyl-16β-(n-propylthio)-5α-androstane;
3-oxo-4-aza-4,7β-dimethyl-16β-fluoro-5α-androstane;
3-oxo-4-aza-4,7β-dimethyl-16β-cyano-5α-androstane;
3-oxo-4-aza-4,7β-dimethyl-16β-(1-hexyl)-5α-androstane;
3-oxo-4-aza-4,7β-dimethyl-16β-(n-propyl)-5α-androstane;
3-oxo-4-aza-4,7β-dimethyl-16β-benzyl-5α-androstane;
3-oxo-4-aza-4,7β-dimethyl-16β-(4-chlorobenzyl)-5α-androstane;
3-oxo-4-aza-4,16α-dimethyl-16β-methoxy-5α-androstane;
3-oxo-4-aza-4,7β-dimethyl-16β-(4-cyanophenoxy)-5α-androstane;
3-oxo-4-aza-4,7β-dimethyl-16β-(3-cyanophenoxy)-5α-androstane;
3-oxo-4-aza-4,7β-dimethyl-16β-(4-nitrophenoxy)-5α-androstane;
3-oxo-4-aza-4,7β-dimethyl-16β-(1-naphthyloxy)-5α-androstane;
3-oxo-4-aza-4,7β-dimethyl-16β-(3-chloro-4-methylphenoxy)-5α-androstane;
3-oxo-4-aza-4,7β-dimethyl-16β-(4-methylphenoxy)-5α-androstane;
3-oxo-4-aza-4,7β-dimethyl-16β-(tert-butyloxy)-5α-androstane;
3-oxo-4-aza-4,7β-dimethyl-16β-(3-methyl-1-butyloxy)-5α-androstane;
3-oxo-4-aza-4,7β-dimethyl-16α-(n-propyloxy)-5α-androstane;
3-oxo-4-aza-4,7β-dimethyl-16β-(4-trifluoromethylphenoxy)-5α-androstane;
3-oxo-4-aza-4,7β-dimethyl-16β-(4-trifluoromethoxyphenoxy)-5α-androstane;
3-oxo-4-aza-4,7β-dimethyl-16β-ethylthio-5α-androstane;
3-oxo-4-aza-4,7β-dimethyl-16β-ethylsulfonyl-5α-androstane;
3-oxo-4-aza-4,7β-dimethyl-16β-(4-methylsulfonylphenoxy)-5α-androstane;
3-oxo-4-aza-4,7β-dimethyl-16β-(4-(4-tolylsulfonylamino)phenoxy)-5α-androstane;
3-oxo-4-aza-4,7β-dimethyl-16β-(3-pyridyloxy)-5α-androstane;
3-oxo-4-aza-4,7β-dimethyl-16β-((4-phenyl)phenoxy)-5α-androstane;
3-oxo-4-aza-4,7β-dimethyl-16β-(4-fluorophenoxy)-5α-androstane;
3-oxo-4-aza-4,7β-dimethyl-16β-[4-(5-oxazolyl)phenoxy]-5α-androstane;
3-oxo-4-aza-4,7β-dimethyl-16β-[4-(1-pyrrolyl)phenoxy]-5α-androstane;
3-oxo-4-aza-4,7β-dimethyl-16β-(4-aminophenoxy)-5α-androstane;
3-oxo-4-aza-4,7β-dimethyl-16β-(4-acetylaminophenoxy)-5α-androstane;
3-oxo-4-aza-4,7β-dimethyl-16β-(4-benzoylaminophenoxy)-5α-androstane;
3-oxo-4-aza-4,7β-dimethyl-16β-(4-chlorophenoxy)-5α-androstane;
3-oxo-4-aza-4,7β-dimethyl-16β-(phenoxy)-5α-androstane;
3-oxo-4-aza-4,7β-dimethyl-16β-(2-chlorophenoxy)-5α-androstane;
3-oxo-4-aza-4,7β-dimethyl-16β-(3-chlorophenoxy)-5α-androstane;
3-oxo-4-aza-4,7β-dimethyl-16β-(4-chlorophenoxy)-5α-androst-1-ene;
3-oxo-4-aza-4,7β-dimethyl-16-(4-chlorobenzylidene)-5α-androstane;
3-oxo-4-aza-4,7β-dimethyl-16-benzylidene-5α-androstane;
3-oxo-4-aza-4,7β-dimethyl-16-(4-methylbenzylidene)-5α-androstane;
3-oxo-4-aza-4,7β-dimethyl-16-(4-chlorobenzyl)-5α-androstane;
3-oxo-4-aza-4,7β-dimethyl-16-(4-methylbenzyl)-5α-androstane;
3-oxo-4-aza-4,7β-dimethyl-16-(3-pyridylmethyl)-5α-androstane;
3-oxo-4-aza-4,7β-dimethyl-16α-methanesulfonyl-5α-androstane;
3-oxo-4-aza-4,7β-dimethyl-16β-thiophenoxy-5α-androstane;
3-oxo-4-aza-4,7β-dimethyl-16β-(4-chlorothiophenoxy)-5α-androstane;
3-oxo-4-aza-4,7β-dimethyl-16β-(4-fluorothiophenoxy)-5α-androstane;
3-oxo-4-aza-4,7β-dimethyl-16β-(4-methylthiophenoxy)-5α-androstane;
3-oxo-4-aza-4,7β-dimethyl-16β-(4-methoxythiophenoxy)-5α-androstane;
3-oxo-4-aza-4,7β-dimethyl-16β-phenylsulfinyl-5α-androstane;
3-oxo-4-aza-4,7β-dimethyl-16β-phenylsulfonyl-5α-androstane;
3-oxo-4-aza-4,7β,16α-trimethyl-16β-(4-trifluoromethylphenoxy)-5α-androstane,
3-oxo-4-aza-4,7β,16α-trimethyl-16β-hydroxy-5α-androstane;
3-oxo-4-aza-4,7β,16α-trimethyl-16β-methoxy-5α-androstane;
and pharmaceutically acceptable salts thereof.

18. The compound of claim 1 selected from the group consisting of:

3-oxo-4-aza-4,7β-dimethyl-16β-(4-cyanophenoxy)-5α-androstane;
3-oxo-4-aza-4,7β-dimethyl-16β-(3-cyanophenoxy)-5α-androstane;
3-oxo-4-aza-4,7β-dimethyl-16β-(4-nitrophenoxy)-5α-androstane;
3-oxo-4-aza-4,7β-dimethyl-16β-(1-naphthyloxy)-5α-androstane;
3-oxo-4-aza-4,7β-dimethyl-16β-(3-chloro-4-methylphenoxy)-5α-androstane;

3-oxo-4-aza-4,7β-dimethyl-16β-(4-methylphenoxy)-5α-androstane;
3-oxo-4-aza-4,7β-dimethyl-16β-(4-trifluoromethylphenoxy)-5α-androstane;
3-oxo-4-aza-4,7β-dimethyl-16β-(4-trifluoromethoxyphenoxy)-5α-androstane;
3-oxo-4-aza-4,7β-dimethyl-16β-(4-methylsulfonylphenoxy)-5α-androstane;
3-oxo-4-aza-4,7β-dimethyl-16β-(4-(4-tolylsulfonylamino)phenoxy)-5α-androstane;
3-oxo-4-aza-4,7β-dimethyl-16β-(4-phenyl)phenoxy)-5α-androstane;
3-oxo-4-aza-4,7β-dimethyl-16β-(4-fluorophenoxy)-5α-androstane;
3-oxo-4-aza-4,7β-dimethyl-16β-(4-(5-oxazolyl)phenoxy)-5α-androstane;
3-oxo-4-aza-4,7β-dimethyl-16β-(4-(1-pyrrolyl)phenoxy)-5α-androstane;
3-oxo-4-aza-4,7β-dimethyl-16β-(4-aminophenoxy)-5α-androstane;
3-oxo-4-aza-4,7β-dimethyl-16β-(4-acetylaminophenoxy)-5α-androstane;
3-oxo-4-aza-4,7β-dimethyl-16β-(4-benzoylaminophenoxy)-5α-androstane;
3-oxo-4-aza-4,7β-dimethyl-16β-(4-chlorophenoxy)-5α-androstane;
3-oxo-4-aza-4,7β-dimethyl-16β-(phenoxy)-5α-androstane;
3-oxo-4-aza-4,7β-dimethyl-16β-(2-chlorophenoxy)-5α-androstane;
3-oxo-4-aza-4,7β-dimethyl-16β-(3-chlorophenoxy)-5α-androstane;
and the pharmaceutically acceptable salts thereof.

19. The compound of claim 2 wherein:
$R^4$ is selected from the group consisting of hydrogen and methyl, and $R^3$ is selected from the group consisting of:
(b) cyano;
(c) fluoro;
(e) OH;
(g) $C_{1-10}$ alkyl-X—, where alkyl is unsubstituted or substituted with aryl, and wherein aryl in turn is unsubstituted or substituted with 1–2 of halo or $C_{1-6}$alkyl;
(h) $C_{2-10}$ alkenyl-X—;
(i) aryl-X—;
(j) heteroaryl-X—;
wherein the aryl in (i) and heteroaryl in (j) are unsubstituted or substituted with one to two of:
x) halo; cyano; nitro; trihalomethyl; trihalomethoxy; $C_{1-6}$ alkyl; aryl; $C_{1-6}$ alkylsulfonyl; $C_{1-6}$ alkyl-arylsulfonamino;
xi) —$NR_bR_c$; $R_b$—C(O)—N($R_c$)—; wherein $R_b$ and $R_c$ are independently H, $C_{1-6}$ alkyl, aryl, or aryl$C_{1-6}$alkyl; wherein the alkyl moiety is unsubstituted or substituted with 1–3 of: halo; $C_{1-4}$alkoxy; or trifluoromethyl; and the aryl moiety is unsubstituted or substituted with 1–3 of: halo; $C_{1-4}$alkyl; $C_{1-4}$ alkoxy; or trifluoromethyl; and wherein:
X is selected from the group consisting of:
—O—; —S(O)$_n$—; —CH($R_e$)—; —C(O)—N($R_e$)—*; —O—C(O)—N($R_e$)—*;
wherein $R_e$ is H, $C_{1-3}$ alkyl, aryl, aryl $C_{1-3}$ alkyl;
wherein the asterisk (*) denotes the bond which is attached to the 16-position in Structure I; and n is zero or 2.

20. The compound of claim 2 wherein:
$R^4$ is hydrogen, and $R^3$ is selected from the group consisting of:
(b) cyano;
(c) fluoro;
(e) OH;
(g) $C_{1-10}$ alkyl-X—, where alkyl is unsubstituted or substituted with aryl, and wherein aryl in turn is unsubstituted or substituted with 1–2 of halo or $C_{1-6}$alkyl;
(h) $C_{2-10}$ alkenyl-X—;
(i) aryl-X—;
(j) heteroaryl-X—;
wherein the aryl in (i) and heteroaryl in (j) are unsubstituted or substituted with one to two of:
x) halo; cyano; nitro; trihalomethyl; trihalomethoxy; $C_{1-6}$ alkyl; aryl; $C_{1-6}$ alkylsulfonyl; $C_{1-6}$ alkyl-arylsulfonamino;
xi) —$NR_bR_c$; $R_b$—C(O)—N($R_c$)—; wherein $R_b$ and $R_c$ are independently H, $C_{1-6}$ alkyl, aryl, or aryl$C_{1-6}$alkyl; wherein the alkyl moiety is unsubstituted or substituted with 1–3 of: halo; $C_{1-4}$alkoxy; or trifluoromethyl; and the aryl moiety is unsubstituted or substituted with 1–3 of: halo; $C_{1-4}$alkyl; $C_{1-4}$ alkoxy; or trifluoromethyl; and wherein:
X is selected from the group consisting of:
—O—; —S(O)$_n$—; —CH($R_e$)—; —C(O)—N($R_e$)—*; —O—C(O)—N($R_e$)—*;
wherein $R_e$ is H, $C_{1-3}$ alkyl, aryl, aryl $C_{1-3}$ alkyl;
wherein the asterisk (*) denotes the bond which is attached to the 16-position in Structure I; and n is zero or 2.

21. The compound of claim 2 wherein:
$R^4$ is hydrogen, and $R^3$ is selected from the group consisting of:
(g) $C_{1-10}$ alkyl-X—, where alkyl is unsubstituted or substituted with aryl, and wherein aryl in turn is unsubstituted or substituted with 1–2 of halo or $C_{1-6}$alkyl;
(h) $C_{2-10}$ alkenyl-X—;
(i) aryl-X—;
(j) heteroaryl-X—;
wherein the aryl in (i) and heteroaryl in (j) are unsubstituted or substituted with one to two of:
x) halo; cyano; nitro; trihalomethyl; trihalomethoxy; $C_{1-6}$ alkyl; aryl; $C_{1-6}$ alkylsulfonyl; $C_{1-6}$ alkyl-arylsulfonamino;
xi) —$NR_bR_c$; $R_b$—C(O)—N($R_c$)—; wherein $R_b$ and $R_c$ are independently H, $C_{1-6}$ alkyl, aryl, or aryl$C_{1-6}$alkyl; wherein the alkyl moiety is unsubstituted or substituted with 1–3 of: halo; $C_{1-4}$alkoxy; or trifluoromethyl; and the aryl moiety is unsubstituted or substituted with 1–3 of: halo; $C_{1-4}$alkyl; $C_{1-4}$ alkoxy; or trifluoromethyl; and wherein:
X is —O—.

22. A method for treating the condition of acne vulgaris consisting essentially of administering to a mammal in need of such treatment a therapeutically effective amount of a compound of claim 21.

23. A pharmaceutical composition consisting essentially of a pharmaceutically acceptable carrier and a therapeutically effective amount of a compound of claim 21.

* * * * *